US007981599B1

(12) United States Patent
Taneja

(10) Patent No.: US 7,981,599 B1
(45) Date of Patent: Jul. 19, 2011

(54) NON-NUCLEIC ACID PROBES, PROBE SETS, METHODS AND KITS PERTAINING TO THE DETECTION OF INDIVIDUAL HUMAN CHROMOSOMES X, Y, 1, 2, 3, 4, 6, 7, 8, 9, 10, 11, 12, 16, 17, 18 AND 20 AS 13/21 AS A PAIR

(75) Inventor: Krishan L. Taneja, Northboro, MA (US)

(73) Assignee: Boston Probes, Inc., Bedford, MA (US)

( * ) Notice: Subject to any disclaimer, the term of this patent is extended or adjusted under 35 U.S.C. 154(b) by 2522 days.

(21) Appl. No.: 09/627,796

(22) Filed: Jul. 28, 2000

Related U.S. Application Data

(63) Continuation-in-part of application No. 09/520,760, filed on Mar. 7, 2000, which is a continuation-in-part of application No. 09/363,632, filed on Jul. 29, 1999, now abandoned.

(60) Provisional application No. 60/094,874, filed on Jul. 31, 1998, provisional application No. 60/109,313, filed on Nov. 20, 1998, provisional application No. 60/120,827, filed on Feb. 19, 1999, provisional application No. 60/137,636, filed on Jun. 4, 1999.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ......... 435/6; 435/91.1; 536/23.1; 536/24.3
(58) Field of Classification Search ............. 435/6, 91.1; 536/23.1, 24.3, 25.32
See application file for complete search history.

(56) References Cited

U.S. PATENT DOCUMENTS

| 5,434,047 | A | 7/1995 | Arnold | |
| 5,447,841 | A | 9/1995 | Gray | |
| 5,472,842 | A | 12/1995 | Stokke et al. | 435/6 |
| 5,527,675 | A | 6/1996 | Coull et al. | 435/6 |
| 5,539,082 | A | 7/1996 | Nielsen | |
| 5,623,049 | A | 4/1997 | Löbberding et al. | 530/300 |
| 5,629,147 | A | 5/1997 | Asgari et al. | 435/5 |
| 5,714,331 | A | 2/1998 | Buchardt et al. | 435/6 |
| 5,736,336 | A | 4/1998 | Buchardt et al. | 435/6 |
| 5,741,677 | A | 4/1998 | Kozlowski et al. | 435/91.2 |
| 5,759,781 | A | 6/1998 | Ward | |
| 5,773,571 | A | 6/1998 | Nielsen et al. | 530/300 |
| 5,776,688 | A | 7/1998 | Bittner | |
| 5,786,461 | A | 7/1998 | Buchardt et al. | 536/18.7 |
| 5,792,610 | A | 8/1998 | Witney | |
| 5,817,462 | A | 10/1998 | Garini | |
| 5,830,645 | A | 11/1998 | Pinkel | |
| 5,834,193 | A | 11/1998 | Kozlowski et al. | 435/6 |
| 5,837,459 | A | 11/1998 | Berg et al. | 435/6 |
| 5,840,482 | A | 11/1998 | Gray | |
| 5,888,730 | A | 3/1999 | Gray | |
| 5,888,734 | A | 3/1999 | Cremer et al. | 435/6 |
| 5,891,625 | A | 4/1999 | Buchardt et al. | 435/6 |
| 5,972,610 | A | 10/1999 | Buchardt et al. | 435/6 |
| 5,985,563 | A * | 11/1999 | Hyldig-Nielsen et al. | 435/6 |
| 5,986,053 | A | 11/1999 | Ecker et al. | 530/350 |
| 6,015,710 | A | 1/2000 | Shay | |

FOREIGN PATENT DOCUMENTS

| EP | 0878552 A1 | 11/1998 |
| WO | WO95/32305 | 11/1995 |
| WO | WO 95/32305 | * 11/1995 |
| WO | WO97/14026 | 4/1997 |
| WO | WO97/18325 | 5/1997 |
| WO | WO98/24933 | 6/1998 |

OTHER PUBLICATIONS

Petersen et al., Bioorganic & Medicinal Chemistry Letters, vol. 5, pp. 1119-1124, 1995.*
Capasso et al., Tetrahedron, vol. 57, pp. 9481-9486, 2001.*
Von Wintzingerode et al; FEMS Microbiology Ecology, vol. 24, pp. 201-209, 1997; abstract and sequence information provided.*
D'Aiuto, L. et al, Cloning and comparative mapping of a human chromosome 4-specific alpha satellite DNA sequence. Genomics 18, 230-0235 (1993).
Greig, G.M. et al, Organization and evolution of an alpha satellite DNA subset shared by human chromosomes 13 and 21. J. Mol. Evol. 37, 464-475 (1993).
Ikeno, M. et al, Distribution of CENP-B boxes reflected In CREST centromere antigenic sites on long-range -satellite DNA arrays of human chromosome 21. Hum. Mol. Gen. 3, 1245-1257 (1994).
Mashkova, T.D. et al, Genomic organization, sequence and polymorphism of the human chromosome 4-specific -satellite DNA. Gene 140, 211-217 (1994).

(Continued)

*Primary Examiner* — Jehanne S Sitton

(57) ABSTRACT

This invention is related to novel non-nucleic acid probes, probe sets, methods and kits pertaining to the detection, identification or quantitation of human chromosomes X, Y, 1, 2, 3, 4, 6, 7, 8, 9, 10, 11, 12, 13, 16, 17, 18, 20 and/or 21. The non-nucleic acid probes, probe sets, methods and kits of this invention are particularly well suited for use in multiplex ISH and FISH assays wherein each of chromosomes X, Y, 1, 2, 3, 4, 6, 7, 8, 9, 10, 11, 12, 16, 17, 18 and/or 20, as well as 13/21 as a pair, in a sample or cell can be individually detected, identified or quantitated in the same assay. Multiplex ISH and FISH assays are possible because two or more of the probes used in the assay are labeled with one or more independently detectable labels. Preferably, the independently detectable labels are independently detectable fluorophores. In preferred embodiments, one or more of the probes comprise two or more linked independently detectable moieties wherein the combination of the two or more independently detectable moieties is used to detect, identify or quantitate a particular probe/target sequence hybrid. The methods, kits, probes and probe sets of this invention are particularly well suited for automated analysis, including a slide scanner based system, microscope and CCD camera or a flow cytometer. Furthermore, this invention is particularly useful for detection and identifying chromosome abnormalities such as aneuploidy and polyploidy karyotypes and particularly for preimplantation diagnosis, for prenatal screening and for clinical diagnostic applications.

28 Claims, 6 Drawing Sheets

OTHER PUBLICATIONS

Rocchi, M. et al, A human chromosome 9-specific alphoid DNA repeat spatially resolvable from satellite 3 DNA by fluorescent In situ hybridization. Genomics 9, 517-523 (1991).

Waye, J.S. et al, Genomic organization of alpha satellite DNA on human chromosome 7: evidence for two distinct alphoid domains on a single chromosome. Mol. and Cell. Biology 7, 349-356 (1987).

Alexandrov, I.A. et al, Chromosome-specific alpha satellites: two distinct families on human chromosome 18. Genomics 11, 15-23 (1991).

Bergmann, F. et al, Solid phase synthesis of directly linked PNA-DNA-hybrids. Tet. Lett. 36, 6823-6826 (1995).

Chevret, E. et al, Increased incidence of hyperhaploid 24,XY spermatozoa detected by three-colour FISH in a 46,WY/47,XXY male. Hum. Genet. 97, 171-175 (1996).

Chong, S.S. et al, Preimplantation prevention of X-linked disease: reliable and rapid sex determination of single human cells by restriction analysis of simultaneously amplified ZFX and ZFY sequences. Human Mol. Gen. 2, 1187-1191 (1993).

Cooke, H.J. et al, Characterisation of a human Y chromosome repeated sequence and related sequences in higher primates. Chromosoma 87, 491-502 (1982).

Coonen, E. et al, Optimal preparation of preimplantation embryo interphase nucelic for analysis by fluorescene in-situ hybridization. Human Repro. 9, 533-537 (1994).

Cozzi, J. et al, Achievement of meiosis in XXY germ cells: study of 543 sperm karyotypes from an XY/XXY mosaic patient. Hum. Genet. 93, 32-34 (1994).

Delhanty, J.D.A. et al, Detection of aneuplooidy and chromosomal mosaicism in human embryos during preimplantation sex determination by fluorescent in situ hybridization, (FISH). Human Mol. Genet. 2, 1183-1185 (1993).

Delhanty, J.D.A., Preimplantation diagnosis. Prenatal Diagnosis 14, 1217-1227 (1994).

Dewald, G. et al, A multicenter investigation with interphase fluorescence in situ hybridization using X and Y-chromosome probes. Am. J. Med. Genet. 76, 318-326 (1998).

Dewald, G.W. et al, Fluorescence in situ hybridization with X and Y chromosome probes for cytogenetic studies on bone marrow cells after opposite sex transplantation. Bone Marrow Transplan. 12, 149-154 (1993).

Divane, A. et al, Rapid prenatal diagnosis of aneuploidy from uncultured amniotic fluid cells using five-colour fluorescence in situ hybridization. Prenatal Diagnosis 14, 1061-1069 (1994).

Egholm, M. et al, PNA hybridizes to complementary oligonucleotides obeying the Watson-Crick hydrogen-bonding rules. Nature 365, 566-568 (1993).

Estop, A.M. et al, Meiotic products of a Klinefelter 47,XXY male as determined by sperm fluorescence in-situ hybridization analysis. Human Repro. 13, 124-127 (1998).

Frommer, M. et al, Human satellite I sequences include a male specific 2.47 kb tandemly repeated unit containing one Alu family member per repeat. Nucl. Acids Res. 12, 2887-2900 (1984).

Gersen, S.L. et al, Rapid prenatal diagnosis of 14 cases of triploidy using FISH with multiple probes. Prenatal Diagnosis 15, 1-5 (1995).

Good, L. et al, Review: Progress in developing PNA as a gene-targeted drug. Antisense & Nucl. Acid Drug Dev. 7, 431-437 (1997).

Greig, G.M. et al, Chromosome-specific alpha satellite DNA from the centromere of human chromosom 16. Am. J. Hum. Genet. 45, 862-872 (1989).

Griffin, D.K. et al, Dual fluorescent in situ hybridization for simultaneous detection of X and Y chromosome-specific probes for the sexing of human preimplantation embryonic nuclei. Hum. Genet. 89, 18-22 (1992).

Griffin, D.K. et al, Diagnosis of sex in preimplantation embryos by fluorescent in situ hybridisation. Brit. J. Medicine 306, 1382 (1993).

Grifo, J.A. et al, Preembryo biopsy and analysis of blastomeres by in situ hybridization. Am. J. Obstet. Gynecol. 163, 2013-2019 (1990).

Haaf, T. et al, Organization, polymorphism, and molecular cytogenetics of chromosome-specific ∝-satellite DNA from the centromere of chromosome 2. Genomics 13, 122-128 (1992).

Haaima, G. et al, Peptide Nucleic Acids (PNAs) containing thymine monomers derived from chiral amin acids: hybridization and solubility properties of D-lysine PNA. Angew. Chem. Int. Ed. Engl. 35, 1939-1942 (1996).

Han, T.L. et al, Simultaneous detection of X- and Y-bearing human sperm by double fluorescence in situ hybridization. Molecular Repro. and Dev. 34, 308-313 (1993).

Handyside, A.H. et al, Biopsy of human preimplantation embryos and sexing by DNA amplification. The Lancet Feb. 18, 347-349 (1989).

Handyside, A.H. et al, Pregnancies from biopsied human preimplantation embryos sexed by Y-specific DNA amplification. Nature 344, 768-770 (1990).

Harper, J.C. et al, Identification of the sex of human preimplantation embryos in two hours using an improved spreading method and fluorescent in-situ hybridization (FISH) using directly labelled probes. Human Repro. 9, 721-724 (1994).

Harper, J.C., Preimplantation diagnosis of inherited disease by embryo biopsy: an update of the world figures. J. Assisted Repr. and Genetics 13, 90-95 (1996).

Harris, C. et al, Potential use of buccal smears for rapid diagnosis of autosomal trisomy or chromosomal sex in newborn infants using DNA probes. Amer. J. Med. Genetics 53, 355-358 (1994).

Howe, J.R. et al, Development of a sequence-tagged site for the centromere of chromosome 10: its use in cytogenetic and physical mapping. Hum. Genet. 91, 199-204 (1993).

Jabs, E.W. et al, Characterization of Human Centromeric Regions of Specific Chromosomes by Means of Alphoid DNA Sequences. Am. J. Hum. Genet. 41, 374-390 (1987).

Jacobs, P.A., Epidemiloology of chromosome abnormalities in man. Amer. J. Epidemiology. 105, 180-191 (1977).

Jenkins, R.B. et al, Fluorescence in situ hybridization: a sensitive method for trisomy 8 detection in bone marrow specimens. Blood 79, 3307-3315 (1992).

Johnson, L.A. et al, Gender preselection in humans? Flow cytometric separation of X and Y spermatozoa for the prevention of X-linked diseases. Human Repro. 8, 1733-1739 (1993).

Kihana, T. et al, Allelic loss of chromosome 16q in endometrial cancer: correlation with poor prognosi of patients and less differentiated histology. Jpn. J. Cancer Res. 87, 1184-1190 (1996).

Kontogianni, E.H. et al, Co-amplification of X- and Y-specific sequences for sexing preimplantation human embryos. Preimplantation Genetics (ed. Verlinsky and Kuliev) 139-145 (1991).

Lansdorp, P.M. et al, Heterogeneity in telomere length of human chromosomes. Human Mol. Genet. 5, 685-691 (1996).

Lesnik, E. et al, Triplex formation between DNA and mixed purine-pyrimidine PNA analog with lysines in backbone. Nucleosides & Nucleotides 16, 1775-1779 (1997).

Liu, J. et al, Amplification of X- and Y-chromosome-specific regions from single human blastomeres by polymerase chain reaction for sexing of preimplantation embryos. Human Repro. 9, 716-720 (1994).

Lu, P.Y. et al, Dual color fluorescence in situ hybridization to investigate aneuploidy in sperm from 33 normal males and a man with a t(2;4;8)(q23;q27;p21). Fertility and Sterility 62, 394-399 (1994).

Lubs, H.A. et al, Chromosomal abnormalities in the human population: estimation of rates based on New Haven newborn study. Science 169, 495-497 (1970).

Martini, E. et al, Constitution of semen samples from XYY and XXY males as analysed by in situ hybridization. Human Repro. 11, 1638-43 (1996).

Matera, A.G. et al, An oligonucleotide probe specific to the centromeric region of human chromosome 5 Genomics 18, 729-731 (1993).

Meyne, J. et al, In situ hybridization using synthetic oligomers as probes for centromere and telomere repeats. Methods in Mol. Biol. 33, 63-74 (1994).

Munne, S. et al, Chromosome abnormalities in human arrested preimplantation embryos: a multiple-probe FISH study. Am. J. Hum. Genet. 55, 150-159 (1994).

Munne, S. et al, Diagnosis of major chromosome aneuploidies in human preimplantation embryos. Human Repro. 8, 2185-2191 (1993).

Nath, J. et al, Fluorescence in situ hybridization (FISH): DNA probe production and hybridization criteria. Biotechnic & Histochem. 73, 6-22 (1998).

Nielsen, P.E. et al, Peptide nucleic acids (PNAs): potential anti-sense and anti-gene agents. Anti-Cancer Drug Design 8, 53-63 (1993).

Rao, P. N. et al, Rapid detection of aneuploidy in uncultured chorionic villus cells using fluorescence in situ hybridization. Prenatal Diagnosis 13, 233-238 (1993).

Schad, C.R. et al, Application of fluorescent in situ hybridization with X and Y chromosome specific probes to buccal smear analysis. Am. J. Medical Genet. 66, 187-192 (1996).

Schrurs, B.M. et al, Preimplantation diagnosis of aneuploidy using fluorescent in-situ hybridization: evaluation using a chromosome 18-specific probe. Human Repro. 8, 296-301 (1993).

Stallings, R.L. et al, Chromosome 16-specific repetitive DNA sequences that map to chromosomal regions known to undergo breakage/rearrangement in leukemia cells. Genomics 13, 332-338 (1992).

Strom, C.M. et al, Reliability of gender determination using the polymerase chain reaction (PCR) for single cells. J. of in Vitro Fertil. and Embryo Transfer 8, 225-229 (1991).

Taneja, K.L., Localization of trinucleotide repeat sequences in myotonic dystrophy cells using a single fluorochrome-labeled PNA probe. BioTech. 24, 472-476 (1998).

Tomac, S. et al, Ionic effects on the stability and conformation of peptide nucleic acid complexes. J. Am. Chem. Soc. 118, 5544-5552 (1996).

van Tol, M.J.D. et al, Simultaneous detection of X and Y chromosomes by two-colour fluorescence in situ hybridization in combinant with immunophenotyping of single cells to document chimaerism after sex-mismatched bone marrow transplantation. Bone Marrow Transplan. 21, 497-503 (1998).

Vidal, F. et al, Efficiency of microsort flow cytometry for producing sperm populations enriched in X- or Y-chromosome haplotypes: a blind trial assessed by double and triple colour fluorescent in-situ hybridization. Human Repro. 13, 308-312 (1998).

Waye, J.S. et al, Chromosome-specific alpha satellite DNA: nucleotide sequence analysis of the 2.0 kilobasepair repeat from the human X chromosome. Nucl. Acids Res. 13, 2731-2743 (1985).

Waye, J.S. et al, Molecular analysis of a deletion polymorphism in alpha satellite of human chromosome 17: evidence for homologous unequal crossing-over and subsequent fixation. Nucl. Acids Res. 14, 6915-6927 (1986).

Waye, J.S. et al, Structure, organization, and sequence of alpha satellite DNA from human chromosome 17: evidence for evolution by unequal crossing-over and an ancestral pentamer repeat shared with the human X chromosome. Molecular and Cell. Bio. 6, 3156-3165 (1986).

Weiler, J. et al, Hybridisation based DNA screening on peptide nucleic acid (PNA) oligomer arrays. Nucl. Acids Res. 25, 2792-2799 (1997).

Baldini, A. GeneBank accession #X58269.

Baldini A. et al. GeneBank accession #X56450.

Bates, G. et al. "Trinucleotide Repeat Expansions And Human Genetic Disease". BioEssays 4, 277-284 (1994).

Betts, L. et al. "A Nucleic Acid Triple Helix Formed By A Peptide Nucleic Acid". DNA Complex 270, 1838-1841 (1995).

Boffa, L. et al. "Isolation Of Active Genes Containing CAG Repeats By DNA Strand Invasion By A Peptide Nucleic Acid". Proc. Natl. Acad. Sci. USA 92, 1901-1905 (1995).

Böhler, C. et al. "Template Switching Between PNA And RNA Oligonucleotides". Nature 376, 578-581 (1995).

Bonham, M. et al. "An Assessment Of The Antisense Properties Of RNase H-Competent And Steric-Blocking Oligomers". Nucleic Acids Research 23, 1197-1203 (1995).

Brook, J. et al. "Molecular Basis Of Myotonic Dystrophy: Expansion Of A Trinucleotide (CTG) Repeat At The 3' End Of A Transcript Encoding A Protein Kinase Family Member". Cell 68, 799-808 (1992).

Buxton, J. et al. "Detection Of An Unstable Fragment Of DNA Specific To Individuals With Mytonic Dystrophy". Nature 355, 547-551 (1992).

Caskey, C. et al. "Triplet Repeat Mutations In Human Disease". Science 256, 784-789 (1992).

Cherny, D. et al. "DNA Unwinding Upon Strand-Displacement Binding Of A Thymine-Substituted Polyamide To Double-Stranded DNA". Proc. Natl. Acad. Sci. USA 90, 1667-1670 (1993).

Davies, K. "Triplet Repeats On The Rise". Nature 364, 88 (1993).

Demers, D. et al. "Enhanced PCR Amplification Of VNTR Locus D1S80 Using Peptide Nucleic Acid". Nucleic Acids Research 23, 3050-3055 (1995).

Demidov, V. et al. "Electron Microscopy Mapping Of Oligopurine Tracts In Duplex DNA By Peptide Nucleic Acid Targeting". Nucleic Acids Research 22, 5218-5222 (1994).

Demidov, V. et al. "Kinetics And Mechanism Of Polyamide ("Peptide") Nucleic Acid Binding To Duplex DNA". Proc. Natl. Acad. Sci. USA 92, 2637-2641 (1995).

Demidov, V. et al. "Sequence Selective Double Strand DNA Cleavage by Peptide Nucleic Acid (PNA) Targeting Using Nuclease S1". Nucleic Acids Research 9, 2103-2107 (1993).

Egholm, M. et al. "Efficient pH-Independent Sequence-Specific DNA Binding by Pseudoisocytosine-Containing Bis-PNA". Nucleic Acids Research 23, 217-222 (1995).

Egholm, M. et al. "Peptide Nucleic Acid (PNA) And Its Use As An Analytical Molecular Biology Tool". Perseptive Biosystems Technical Newsletter 4, 1-4 (1996).

Eichler, E. et al. "Fine Structure Of The Human FMR1 Gene". Human Molecular Genetics 8, 1147-1153 (1993).

Fischbeck, K. et al. "The Mechanism Of Myotonic Dystrophy". Annals Of Neurology 3, 255-256 (1994).

Fu, Y. et al. "An Unstable Triplet Repeat IN a Gene Related to Myotonic Dystrophy". Science 255, 1256-1258 (1992).

Fu, Y. et al. "Decreased Expression Of Myotonin-Protein Kinase Messenger RNA And Protein In Adult Form Of Myotonic Dystrophy". Science 260, 235-237 (1993).

Harley, H. et al. "Unstable DNA Sequence In Myotonic Dystrophy". The Lancet 8802, 1125-1128 (1992).

Hanvey, J. et al. "Antisense And Antigene Properties Of Peptide Nucleic Acids". Science 258, 1481-1485.

Houseman, D. "Gain Of Glutamines, Gain Of Function?". Nature Genetics 10, 3-4 (1995).

Hummerich, H. et al. "Trinucleotide Repeat Expansion And Human Disease". Electrophoresis 16, 1698-1704 (1995).

Iyer, M. et al. "Accelerated Hybridization Of Oligonucleotides To Duplex DNA". Journal Of Biological Chemistry 24, 14712-14717 (1995).

Jasper, A. et al. "Myotonic Dystrophy: Correlation Of Clinical Symptoms With The Size Of The CTG Trinucleotide Repeat". J. Neurol 242, 99-104 (1995).

Johnson, D. et al. "Microdissection Of A Human Marker Chromosome Reveals Its Origin And A New Family Of Centromeric Repetitve DNA". Hum. Mol. Genet. 1, 741-747, 1992.

Kamenetskii, F. et al. "Stability Of Peptide Nucleic Acids In Human Serum And Cellular Extracts". Biochemical Phar. 6. 1310-1313 (1994).

Kinoshita, M. et al. "$(CTG)_n$ Expansions In Various Tissues From A Myotonic Dystophy Patient". Muscle and Nerve 19, 240-242 (1996).

Knudsen, H. et al. "Antisense Properties Of Duplex- And Triplex-Forming PNAs". Nucleic Acids Research 24, 494-500 (1996).

Larsen, H. et al. "Transcription-Mediated Binding Of Peptide Nucleic Acid (PNA) To Double-Stranded DNA: Sequence-Specific Suicide Transcription". Nucleic Acids Research 24, 458-463 (1996).

La Spada, A. et al. "Trinucleotide Repeat Expansion In Neurological Disease". Neurological Progress 6, 814-822 (1994).

Leijon, M. et al. "Structural Characterization Of PNA-DNA Duplexes By NMR. Evidence For DNA In A B-Like Conformation". Biochemistry 33, 9820-9825 (1994).

Maddox, J. "Triplet Repeat Genes Raise Questions". Nature 368, 685 (1994).

Mahadevan, M. et al. "Myotonic Dystrophy Mutation: An Unstable CTG Repeat in the 3' Untranslated Region Of The Gene". Science 255, 1253-1255 (1992).

Mandel, J. "Trinucleotide Diseases On The Rise". Nature Genetics 7, 453-455 (1994).

Møllegaard, N. et al. "Peptide Nucleic Acid DNA Strand Displacement Loops As Artificial Transcription Promoters". Proc. Natl. Acad. Sci. USA 91, 3892-3895 (1994).

Morell, V. "The Puzzle Of The Triple Repeats". Science 260, 1422-1423 (193).

Nielsen, P. et al. "Sequence Specific Inhibition Of DNA Restriction Enzyme Cleavage By PNA". Nucleic Acids Research 2, 197-200 (1993).

Nielsen, P. et al. "Sequence-Specific Transcription Arrest By peptide Nucleic Acid Bound To The DNA Template Strand". Gene 149, 139-145 (1994).

Nielsen, P. et al. "Sequence-Selective Recognition Of DNA By Strand Displacement With A Thymine-Substituted Polyamide". Science 254, 1497-1500 (1991).

Ørum H. et al. "Sequence-Specific Purification Of Nucleic Acids By PNA-Controlled Hybrid Selection". BioTechniques 19, 472-480 (1995).

Ørum H. et al. "Single Base Pair Mutation Analysis By PNA Directed PCR Clamping". Nucleic Acids Research 21, 5332-5336 (1993).

Pardridge, W. et al. "Vector-Mediated Delivery Of A Polyamide ("Peptide") Nucleic Acid Analogue Through The Blood-Brain Barrier in vivo". Proc. Natl. Acad. Sci. USA 92, 5592-5596 (1995).

Peffer, N. et al. "Strand-Invasion Of Duplex DNA By Peptide Nucleic Acid Oligomers". Proc. Natl. Acad. Sci. USA 90, 10648-10652 (1993).

Plassart, E. et al. "Genes With Triplet Repeats: A New Class Of Mutations Causing Neurological Diseases". Biomed & Pharmacother 48, 191-197 (1994).

Richards, R. et al. "Simple Repeat DNA Is Not Replicated Simply". Nature Genetics 6, 114-116 (1994).

Rose, D. "Characterization Of Antisense Binding Properties Of Peptide Nucleic Acids By Capillary Gel Electrophoresis". Anal. Chem. 65, 3545-3549 (1993).

Taneja, K. et al. "Foci Of Trinucleotide Repeat Transcripts In Nuclei Of Myotonic Dystrophy Cells And Tissues". The Journal Of Cell Biology 128, 995-1002 (1995).

Thiede, C. et al. "Simple And Sensitive Detection Of Mutations In The Ras Proto-Oncogenes Using PNA-Mediated PCR Clamping". Nucleic Acids Research 5, 983-984 (1996).

Thompson, A. et al. "Congenital Myotonic Dystophy". Elsevier Science Inc. (1995).

Thornton, C. et al. "Myotonic Dystrophy Patients Have Larger CTG Expansions In Skeletal Muscle Thank in Leukocytes". Annals Of Neurology 35, 104-107.

Torres, R. et al. "Interresidue Hydrogen Bonding In A Peptide Nucleic Acid RNA Heteroduplex". Proc. Natl. Acad. Sci. USA 93, 649-653 (1996).

Veselkov, A. et al. "A New Class Of Genome Rare Cutters". Nucleic Acids Research 24, 2483-2487 (1996).

Wang, Y. et al. "Expanded CTG Triplet Blocks From The Myotonic Dystrophy Gene Crete The Strongest Known Natural Nucleosome Positioning Elements". Genomics 25, 570-573 (1995).

Warren, S. et al. "Trinucleotide Repeat Expansions In Neurological Disease". Current Opinion In Neurology 3, 752-759 (1993).

Wieringa, B. et al. "Commentary: Myotonic Dystrophy Reviewed: Back To The Future?" Human Molecular Genetics 3, 1-7 (1994).

Williams, P. "Dynamic Mutations Hit Double Figures". Nature Genetics 8, 213-215 (1994).

Wittung, P. et al. "DNA-Like Double Helix Formed By Peptide Nucleic Acid". Nature 368, 561-563 (1994).

Wittung, P. et al. "Phospholipid membrane Permeability Of Peptide Nucleic Acid". FEBS Letters 365, 27-29 (1995).

Wong, L. et al. "Somatic Heterogeneity Of The CTG Repeat In Myotonic Dystrophy Is Age And Size Dependent". Am. J. Hum. Genet. 56, 114-122 (1995).

Hunter, Craig P., "Evidence from mosaic analysis of the masculinizing gene her-1 for cell interactions in *C. elegans* sex determination", Nature, vol. 355, Feb. 6, 1992, pp. 551-555.

* cited by examiner

Detection of X (orange), Y (green) and 1 (red) chromosomes in human cells

SEQUENCE LISTING

```
<160> NUMBER OF SEQ ID NOS: 159

<210> SEQ ID NO 1
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 1
cttcaaagag gtccacga                                                 18

<210> SEQ ID NO 2
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 2
agggttcaac tgtgtgac                                                 18

<210> SEQ ID NO 3
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 3
gaaacttctg agtgatga                                                 18
```

```
<210> SEQ ID NO 4
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 4
cagtcatcgc agaaaact                                                 18

<210> SEQ ID NO 5
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 5
agatttcact ggaaacgg                                                 18

<210> SEQ ID NO 6
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 6
gttatgggaa ggtgatcc                                                 18

<210> SEQ ID NO 7
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 7
tcgagccgca gagtttaa                                                 18

<210> SEQ ID NO 8
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 8
ctatttagcg ggcttgga                                                 18
```

```
<210> SEQ ID NO 9
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 9
tacaagggtg ttgcaaac                                                 18

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 10
ccatatgcag ttataagtag g                                             21

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 11
tattgtacca agcagagtac c                                             21

<210> SEQ ID NO 12
<211> LENGTH: 23
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 12
ggtatatata agatgacaca gga                                           23

<210> SEQ ID NO 13
<211> LENGTH: 23
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 13
gttagttata ttgggtgata tgt                                           23
```

```
<210> SEQ ID NO 14
<211> LENGTH: 20
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 14
tcacataata gacaacatac                                                   20

<210> SEQ ID NO 15
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 15
cagaagagat tgaacctt                                                     18

<210> SEQ ID NO 16
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 16
ggcatagcac ataacatg                                                     18

<210> SEQ ID NO 17
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 17
aatcgtcatc gaatgaat                                                     18

<210> SEQ ID NO 18
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 18
cattgaacag aattgaat                                                     18
```

```
<210> SEQ ID NO 19
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 19
gttttcaggg gaagatat                                                 18

<210> SEQ ID NO 20
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 20
tgtgcgccct caactaac                                                 18

<210> SEQ ID NO 21
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 21
gaagcttcat tgggatgt                                                 18

<210> SEQ ID NO 22
<211> LENGTH: 19
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 22
ccaataaaag ctacataga                                                19

<210> SEQ ID NO 23
<211> LENGTH: 20
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 23
gaaaagtttt ctgacattgc                                               20
```

```
<210> SEQ ID NO 24
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 24
tagttgaagg gcacatca                                                 18

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 25
cacaaataag attctaagaa t                                             21

<210> SEQ ID NO 26
<211> LENGTH: 20
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 26
tcaaaagaat gcttcaacac                                               20

<210> SEQ ID NO 27
<211> LENGTH: 19
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 27
ataattagac cggaatcat                                                19

<210> SEQ ID NO 28
<211> LENGTH: 19
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 28
gctgttttct aaaggaaag                                                19
```

```
<210> SEQ ID NO 29
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 29
aagacttcaa agaggtcc                                                 18

<210> SEQ ID NO 30
<211> LENGTH: 21
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 30
tttgtcaaga attataagaa g                                             21

<210> SEQ ID NO 31
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 31
caagattgct tttaatgg                                                 18

<210> SEQ ID NO 32
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 32
tgtgtatcaa ctcacgga                                                 18

<210> SEQ ID NO 33
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 33
cctcacaaag tagaaact                                                 18
```

```
<210> SEQ ID NO 34
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 34
gaaaaagcag ttactgag                                                 18

<210> SEQ ID NO 35
<211> LENGTH: 20
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 35
taataattag acggaatcat                                               20

<210> SEQ ID NO 36
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 36
ttacagggca ttgaagcc                                                 18

<210> SEQ ID NO 37
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 37
cagttatgaa gcagtctc                                                 18

<210> SEQ ID NO 38
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 38
cacaccagaa aaagcagt                                                 18
```

```
<210> SEQ ID NO 39
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 39
aagggtaaac actgtgag                                                 18

<210> SEQ ID NO 40
<211> LENGTH: 21
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 40
agacaacgaa atatcttcat g                                             21

<210> SEQ ID NO 41
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 41
ctagcagtat gaggtcaa                                                 18

<210> SEQ ID NO 42
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 42
gcagacttca gaaacaga                                                 18

<210> SEQ ID NO 43
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 43
ggcctcaaag acgtttaa                                                 18
```

```
<210> SEQ ID NO 44
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 44
gtgaaagttc caagtgaa                                                 18

<210> SEQ ID NO 45
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 45
gagtgctttg aagcctac                                                 18

<210> SEQ ID NO 46
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 46
gaaacagcag agttgaaa                                                 18

<210> SEQ ID NO 47
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 47
tgcagagatc acaacgtg                                                 18

<210> SEQ ID NO 48
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 48
acaaagaatc attcgcag                                                 18
```

```
<210> SEQ ID NO 49
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 49
agtgttagaa aactgctc                                                 18

<210> SEQ ID NO 50
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 50
ctgttcagag taacatga                                                 18

<210> SEQ ID NO 51
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 51
ccgcttggaa atactaca                                                 18

<210> SEQ ID NO 52
<211> LENGTH: 19
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 52
gaaatggaaa tatctcccc                                                19

<210> SEQ ID NO 53
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 53
tctaggaggt ccaattat                                                 18
```

```
<210> SEQ ID NO 54
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 54
gaattcccaa gtggatat                                                 18

<210> SEQ ID NO 55
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 55
ctgtaggttt agatgaag                                                 18

<210> SEQ ID NO 56
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 56
aaggagtgtt tcccaact                                                 18

<210> SEQ ID NO 57
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 57
ggcttcaagg cgctctaa                                                 18

<210> SEQ ID NO 58
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 58
gcagagactt caaagtgc                                                 18
```

```
<210> SEQ ID NO 59
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 59
cacacacacg gtggacca                                                   18

<210> SEQ ID NO 60
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 60
caaagggaat gttccatt                                                   18

<210> SEQ ID NO 61
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 61
cacatagcag tgtttgag                                                   18

<210> SEQ ID NO 62
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 62
ctcaaggcgg tccaatta                                                   18

<210> SEQ ID NO 63
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 63
gagtcgaaat gcacacat                                                   18
```

```
<210> SEQ ID NO 64
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase sequence
<220> FEATURE:
<223> OTHER INFORMATION: Description of Artificial Sequence:Probing
      Nucleobase Sequence Of Non-nucleic Acid Probe

<400> SEQUENCE: 64
taccaagagg aatgttgc                                                 18

<210> SEQ ID NO 65
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 65
acgggatgca atataaaa                                                 18

<210> SEQ ID NO 66
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 66
tgaagattct gcatacgg                                                 18

<210> SEQ ID NO 67
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 67
aaggtttgta ctgacaga                                                 18

<210> SEQ ID NO 68
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 68
ctgaactatg gtgaaaaa                                                 18
```

```
-continued

<210> SEQ ID NO 69
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 69
actaactgtg ctgaacat                                                18

<210> SEQ ID NO 70
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 70
cccatgaatg cgagatag                                                18

<210> SEQ ID NO 71
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 71
aactgaacgc acagatga                                                18

<210> SEQ ID NO 72
<211> LENGTH: 21
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 72
ggctaatctt tgaaattgaa a                                            21

<210> SEQ ID NO 73
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 73
aggtggataa ttggccct                                                18
```

```
<210> SEQ ID NO 74
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 74
tgaagtccaa aaaagcac                                                  18

<210> SEQ ID NO 75
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 75
cttagacatg gaaatatc                                                  18

<210> SEQ ID NO 76
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 76
aaggggtcta actaatca                                                  18

<210> SEQ ID NO 77
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 77
gtagttgttg agaatgat                                                  18

<210> SEQ ID NO 78
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 78
aacttcccag aactacac                                                  18
```

```
<210> SEQ ID NO 79
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 79
attcttgaaa tggaacac                                                 18

<210> SEQ ID NO 80
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 80
ctgtgattgc tgatttgg                                                 18

<210> SEQ ID NO 81
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 81
gtcatcacag gaaacatt                                                 18

<210> SEQ ID NO 82
<211> LENGTH: 19
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 82
gaaatttcct gttgacaga                                                19

<210> SEQ ID NO 83
<211> LENGTH: 19
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 83
gtttgaaagc tgaactatg                                                19
```

```
<210> SEQ ID NO 84
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 84
tcctgtaatg ttcgacag                                                 18

<210> SEQ ID NO 85
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 85
tcatagaacg ctagaaag                                                 18

<210> SEQ ID NO 86
<211> LENGTH: 20
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 86
acctttcttt tgatgaagga                                               20

<210> SEQ ID NO 87
<211> LENGTH: 20
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 87
caaatatcac aaaaagaggg                                               20

<210> SEQ ID NO 88
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 88
gagttgaata gaggcaac                                                 18
```

```
<210> SEQ ID NO 89
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 89
ggccaaatgt agaaaagg                                                  18

<210> SEQ ID NO 90
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 90
gcgttcaact caaggtgt                                                  18

<210> SEQ ID NO 91
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 91
tgtcctttag acagagca                                                  18

<210> SEQ ID NO 92
<211> LENGTH: 20
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 92
tgagaccaaa tgtacaaaag                                                20

<210> SEQ ID NO 93
<211> LENGTH: 21
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 93
gaatactgag taagttcttt g                                              21
```

```
<210> SEQ ID NO 94
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 94
aactgcacaa atagggtg                                                  18

<210> SEQ ID NO 95
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 95
tggagacact gtgtttgt                                                  18

<210> SEQ ID NO 96
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 96
ccagttggag atttcaat                                                  18

<210> SEQ ID NO 97
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 97
gaagcctgcc agtggata                                                  18

<210> SEQ ID NO 98
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 98
tacagcattc tggaaacc                                                  18
```

```
<210> SEQ ID NO 99
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 99
ccagacactg cgtagtga                                                 18

<210> SEQ ID NO 100
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 100
atataatgct agagggag                                                 18

<210> SEQ ID NO 101
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 101
aaaaacaaga caaactcg                                                 18

<210> SEQ ID NO 102
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 102
atttcagctg actaaaca                                                 18

<210> SEQ ID NO 103
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 103
aacgaattat ggtcacat                                                 18
```

```
<210> SEQ ID NO 104
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 104
ggtgacgact gagtttaa                                                    18

<210> SEQ ID NO 105
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 105
tttggaccac tctgtggc                                                    18

<210> SEQ ID NO 106
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 106
aacgggataa ctgcacct                                                    18

<210> SEQ ID NO 107
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 107
tttgtggttt gtggtgga                                                    18

<210> SEQ ID NO 108
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 108
agggaatagc ttcataga                                                    18
```

```
<210> SEQ ID NO 109
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 109
atcacgaaga aggttctg                                                 18

<210> SEQ ID NO 110
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 110
ccgaagatgt ctttggaa                                                 18

<210> SEQ ID NO 111
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 111
aaagaggtct acatgtcc                                                 18

<210> SEQ ID NO 112
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 112
ttcccgtaac aactatgc                                                 18

<210> SEQ ID NO 113
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 113
tcccgtaaca actaggca                                                 18
```

```
<210> SEQ ID NO 114
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 114
aaaaggagtg atccaacc                                                 18

<210> SEQ ID NO 115
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 115
tccctttggt agagcagg                                                 18

<210> SEQ ID NO 116
<211> LENGTH: 20
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 116
atttgagatg tgtgtactca                                               20

<210> SEQ ID NO 117
<211> LENGTH: 17
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 117
gcacttaccg gcctaag                                                  17

<210> SEQ ID NO 118
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 118
ctcagaaact tactcgtg                                                 18
```

```
<210> SEQ ID NO 119
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 119
acacgatttt ggaaacac                                                 18

<210> SEQ ID NO 120
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 120
cgaaacatca ctgagagt                                                 18

<210> SEQ ID NO 121
<211> LENGTH: 20
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 121
ggatgacata taataactag                                               20

<210> SEQ ID NO 122
<211> LENGTH: 20
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 122
gaattgaaca ttcactttga                                               20

<210> SEQ ID NO 123
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 123
tagctctgaa gatttcgt                                                 18
```

```
<210> SEQ ID NO 124
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 124
gagatgtttc cgagaatg                                                    18

<210> SEQ ID NO 125
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 125
gtgtattcaa ctaccaga                                                    18

<210> SEQ ID NO 126
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 126
acatttctgt tacagagc                                                    18

<210> SEQ ID NO 127
<211> LENGTH: 20
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 127
atgacgtata aaatctagag                                                  20

<210> SEQ ID NO 128
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 128
acgaacacag ttgaacct                                                    18
```

-continued

```
<210> SEQ ID NO 129
<211> LENGTH: 20
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 129
ctcataaaaa ccagaaagag                                              20

<210> SEQ ID NO 130
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 130
cagttcatat gtgcagtg                                                18

<210> SEQ ID NO 131
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 131
ggaatatcgt cacctaaa                                                18

<210> SEQ ID NO 132
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 132
tggagcaaat tgaagcct                                                18

<210> SEQ ID NO 133
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 133
tggagcacat ttatgcct                                                18
```

```
<210> SEQ ID NO 134
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 134
tgcattctac tcccatag                                                   18

<210> SEQ ID NO 135
<211> LENGTH: 20
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 135
acactctgtt tctaaaatct                                                 20

<210> SEQ ID NO 136
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 136
gcaggcggat atttagta                                                   18

<210> SEQ ID NO 137
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 137
agcgatttga tgccaaca                                                   18

<210> SEQ ID NO 138
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 138
ttgcaaacgg ggtttctt                                                   18
```

-continued

```
<210> SEQ ID NO 139
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 139
ctttcatgct agacagaa                                                 18

<210> SEQ ID NO 140
<211> LENGTH: 19
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 140
caaaaaagtt actgagaac                                                19

<210> SEQ ID NO 141
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 141
aaaatgccac agcaagag                                                 18

<210> SEQ ID NO 142
<211> LENGTH: 20
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 142
gtttgaaaac acactgtttg                                               20

<210> SEQ ID NO 143
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 143
atatggacct gtttgagg                                                 18
```

<210> SEQ ID NO 144
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 144
cattgaatgc tagacgga                                                 18

<210> SEQ ID NO 145
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 145
atgatgaaaa aggtaata                                                 18

<210> SEQ ID NO 146
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 146
cattctcaga actgtttg                                                 18

<210> SEQ ID NO 147
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 147
acagaactaa accatcgt                                                 18

<210> SEQ ID NO 148
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 148
taggccagct tggaggat                                                 18

```
<210> SEQ ID NO 149
<211> LENGTH: 16
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 149
ctagctggga ggattt                                                        16

<210> SEQ ID NO 150
<211> LENGTH: 16
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 150
tgtgcctcaa ctgaca                                                        16

<210> SEQ ID NO 151
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 151
tgctttggga tgtttcaa                                                      18

<210> SEQ ID NO 152
<211> LENGTH: 20
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 152
gcaatgtcag aactttttc                                                     20

<210> SEQ ID NO 153
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 153
ccgaaagaaa tttgtggg                                                      18
```

```
<210> SEQ ID NO 154
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 154
gaacatggcc tttcatag                                                 18

<210> SEQ ID NO 155
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 155
tcaaggcgat cgaaatgt                                                 18

<210> SEQ ID NO 156
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 156
gagacacata tcaccaac                                                 18

<210> SEQ ID NO 157
<211> LENGTH: 19
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 157
cagaaatttc tttcggata                                                19

<210> SEQ ID NO 158
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 158
gaacatggcc tttcatag                                                 18
```

```
<210> SEQ ID NO 159
<211> LENGTH: 18
<212> TYPE: DNA
<213> ORGANISM: Artificial Sequence
<220> FEATURE:
<223> OTHER INFORMATION: Description of Combined DNA/RNA
      Molecule:Probing Nucleobase Sequence
<220> FEATURE:
<223> OTHER INFORMATION: Description of Artificial Sequence:Probing
      Nucleobase Sequence Of Non-nucleic Acid Probe

<400> SEQUENCE: 159
agccaaagga gttgaaca                                                    18
```

US 7,981,599 B1

NON-NUCLEIC ACID PROBES, PROBE SETS, METHODS AND KITS PERTAINING TO THE DETECTION OF INDIVIDUAL HUMAN CHROMOSOMES X, Y, 1, 2, 3, 4, 6, 7, 8, 9, 10, 11, 12, 16, 17, 18 AND 20 AS 13/21 AS A PAIR

CROSS REFERENCE TO RELATED APPLICATIONS

This application claims the benefit of U.S. Provisional Application No. 60/094,874 filed on Jul. 31, 1998, U.S. Provisional Application No. 60/109,313 filed on Nov. 20, 1998; U.S. Provisional Application No. 60/120,827 filed on Feb. 19, 1999; U.S. Provisional Application No. 60/137,636 filed on Jun. 4, 1999. This application is a continuation-in-part (CIP) of U.S. patent application Ser. No. 09/520,760, filed on Mar. 7, 2000 (pending) which a continuation-in-part of U.S. patent application Ser. No. 09/363,632 filed on Jul. 29, 1999 (now abandoned).

BACKGROUND OF THE INVENTION

1. Field of the Invention

This invention is related to the field of probe-based detection, analysis and quantitation of individual human chromosomes X, Y, 1, 2, 3, 4, 6, 7, 8, 9, 10, 11, 12, 16, 17, 18 and 20 as well as 13/21 as a pair using detectable non-nucleic acid probes.

2. Description of the Related Art

Nucleic acid hybridization is a fundamental process in molecular biology. Probe-based assays are useful in the detection, identification, analysis and quantitation of nucleic acids. Nucleic acid probes have long been used to analyze samples for the presence of nucleic acid from bacteria, eucarya, fungi, virus or other organisms and they are also useful in examining samples for genetically-based disease states or clinical conditions of interest.

Chromosome disorders comprise a significant number of genetic diseases. For example, approximately 16 percent of recessive disorders are the result of X-linked genetic defects for which no specific diagnostic procedure is presently available (See: Delhanty et al. *Human Mol. Genetics.* 2: 1183-1185 (1993)). It has been estimated that detectable chromosomal abnormalities occur with a frequency of one in every 250 births (See: Epstein, The consequency of chromosome imbalance: principle, mechanism and models, Cambridge University Press, 1986; Lubs et al., *Science,* 169: 495-497 (1970); and Jacobs, *Am. J. Epidemiol.* 105: 180-191 (1970)). Abnormalities that involve the deletion or addition of chromosomal materials after the genetic balance of an organism has been determined can lead to serious mental or physical disease and even death. With the arrival, acceptance and rapid proliferation of in-vitro fertilization (IVF), research into methods and compositions suitable for the examination of the chromosomes of ova, spermatozoa, embryo and blastomeres have become commonplace. For example, recent reports have shown increased incidence of hyperhaploid (24/XY) spermatozoa in males with 46 XY/47 XXY karyotypes (See: Cozzi et al, *Hum. Genet.,* 93: 32-34 (1994); Chevret et al. *Hum. Genet.* 97: 171-175 (1996); Martini et al., *Human Reproduction,* 11: 1638-1643 (1996) and Estop et al., *Human Reproduction,* 13: 124-127 (1998)). For families affected by sex linked disorders, preimplantation diagnosis (PID) is essential to insure that the fetus is not affected. Thus, the examination of blastomeres for sex determination and chromosome disorder prior to implantation has become a routine part of the IVF processes since implantation of chromosomally defective embryos will result in either miscarriage or in the birth of an infant having a genetic defect (See: Harper, *Journal of Assisted Reproduction and Genetics,* 13: 90-95 (1996).

Pioneering work directed to preimplantation and prenatal sex determination was performed by Handyside and his colleagues (See: Handyside et al., *The Lancet,* 347-349 (February, 1989) and Handyside et al., *Nature,* 344: 768-770 (1990)). Handyside et al. used PCR to amplify repetitive satellite sequences of the Y-chromosome. This method was at first very attractive since results could be rapidly obtained (approximately 3 hours). Speed is a critical factor in preimplantation diagnosis since implantation can only occur within a short time when the female uterus is suitable to impregnation. Because only the Y-chromosome was detected, the PCR method developed by Handyside et al. predicted a male child when amplification occurred and a female child when no amplification occurred. However, this method had a rather high incidence of misdiagnosis of prenatal and preimplantation sex determination (See: Kontogianni et al., *Preimplantation Genetics,* Plenum Press, New York, pp. 139-145).

Though improvements were made to the PCR technique to allow for the simultaneous and more accurate detection of X and Y chromosomes (See: Chong et al., *Hum. Mol. Genetics,* 2: 1187-1191: (1993) and Strom et al., *J. of in Vitro Fertilization and Embryo Transfer,* 8: 225-229 (1991)), chromosomal disorders such as aneuploidy (including XXY and XYY karyotypes) and polyploidy were not detectable by improved PCR methods since the methods could not quantitate X and Y chromosomes but merely determine their presence or absence. Furthermore, PCR techniques are highly susceptible to misdiagnosis caused by small amounts of foreign (contaminating) DNA (See: Harper et al., *Hum. Reproduction,* 9: 721-724 (1994)).

Given the limitations of PCR, particularly with regard to misdiagnosis or non-diagnosis of aneuploidy and polyploidy conditions, in-situ hybridization (ISH), and particularly fluorescence in-situ hybridization (FISH), has become another used and often preferred method for the analysis of cells, tissues (including bone marrow), spermatozoa, ova, blastomeres, oocysts, buccal cells and chorinic ville. ISH and FISH can be used to examine both metaphase chromosome spreads and interphase nuclei. Because intracelluar chromosomes are routinely visualized (examined) within the nuclei or metaphase condition, the exact number of chromosomes per cell can be quantitated. Therefore, abnormal conditions such as aneuploidy and polyploidy are easily diagnosed. While FISH techniques have become established in clinical and medical applications utilizing nucleic acid probes, typically its Achilles Heal has been that the procedure is often slow to yield results as compared with PCR techniques.

Long arrays of tandemly repeated satellite DNAs are known to exist in the human genome and can generally be organized into distinct classes (See: Greig et al., *Am. J. Hum. Genet.,* 45: 862-872 (1989). However, subsets of the satellite DNA classes appear to have evolved such that they are largely specific to the chromosome of origin. Thus, alpha satellite DNAs provide chromosome specific markers that can be used as a basis of individual chromosome identification. However, there is a possibility that these markers exist in low abundance on other chromosomes and this can lead to detectable cross reactions. (See: Greig et al., *Am. J. Hum. Genet.,* 45: 862-872 (1989) at p. 865, col. 2, lns. 6-15).

ISH and FISH based chromosome analysis is typically performed using DNA probes that are greater than 100 bp in length (often greater than a kb in length), and that typically have multiple labels and that are directed to target sequences of alpha satellite DNA of the chromosome sought to be detected. These probes are typically generated by digestion of naturally occurring DNAs (nick translation) or by enzymatic synthesis using naturally occurring DNA as a template. Thus, the probes are typically a heterogeneous population of numerous fragments, the exact composition of which varies substantially from preparation to preparation. Consequently, the performance of the probes will typically vary substantially from preparation to preparation.

Particularly when utilized in the same assay under a single set of stringency conditions, these nucleic acid probes (composition of nucleic acid fragments) may exhibit some cross reaction to other chromosomes of the sample (See: Matera et al., Genomics, 18: 729-731 (1993)). Cross reaction is at least partially the result of the strong sequence homology within the classes of alpha satellite DNA and thereby requires that the assay exhibit a high degree of discrimination for long DNA probes under preset conditions of stringency. Thus, typical oligonucleotide probes can exhibit cross reaction at, what is commonly referred to as, both low and even high stringency conditions. Since cross hybridization occurs under conditions of both low and high stringency, the signal to noise ratio is poor for these assays regardless of the nature of the stringency conditions. This is particularly disadvantageous for multicolor analysis wherein different fluorophores can exhibit different efficiencies for signal generation. Cross reaction can also be particularly disadvantageous in an assay which is automated since these processes often will mis-call weak signals as false positives.

A commonly used method for reducing cross reaction caused by non-specific hybridization in in-situ hybridization assays involves the use of "blocking nucleic acid" (See: Gray et al., U.S. Pat. No. 5,447,841). Common sources of blocking nucleic acid can include enzymatically digested DNA, salmon sperm DNA as well as other natural sources of heterogenous nucleic acid. Similarly, synthetic oligonucleotides can be used to reduce the binding of probes to non-target sequences though this methodology does not appear to have been utilized in chromosome analysis (See: Arnold et al., U.S. Pat. No. 5,434,047). Likewise, PNA probes have been used to suppress the binding of detectable probes to non-target sequences though again this methodology has not been previously applied to chromosome analysis (See: WIPO Patent Application: WO98/24933).

As applied to the analysis of chromosomes X and Y, ISH and FISH techniques have typically employed DNA probes that have multiple labels and that are typically greater than 100 base pairs (bp) in length and that are prepared by nick translation of cloned DNA greater than 1 kilobase (kb) in length (See: Chevet et al, Hum. Genet., 97: 171-175 (1996)). The most commonly used probes for analysis of sex disorders appear to be commercially available sets of probes CEP X/Y/18/13/21 (See: Munne et al., Human Reproduction, 8: 2185-2191 (1993)) that are available from Vysis, (formerly Imagenetics) or similar DNA probes that are available from Oncor (See: Martini et al., Human Reproduction, 11: 1638-1643 (1996)). Generally, the DNA probes for the analysis of X and Y are directed to target sequences of alpha satellite DNA of the chromosome sought to be detected.

As applied to the analysis of human chromosome 2, ISH and FISH techniques have typically employed nick translated DNA probes that have multiple labels and that are greater than 100 base pairs (bp) in length (See: Haaf et al., Genomics, 13: 122-128 (1992) referencing Greig et al., Am. J. Hum. Genet., 45: 862-872 (1989). Similarly, the FISH analysis of human chromosome 10 was performed using nick translated DNA probe or approximately 175 bp (See: Howe et al., Hum. Genet. 91: 199-204 (1993). Methods and sequence information suitable for producing, by digestion of chromosomal DNA or by nick translation, long DNA probes suitable for the analysis of human chromosome 6 can be found in Jabs et al., Am. J. Hum. Genet. 41: 374-390 (1997).

As applied to the analysis of chromosome 16, ISH and FISH techniques have typically employed nick translated DNA probes that have multiple labels and that are greater than 100 base pairs (bp) in length (See: Greig et al., Am. J. Hum. Genet., 45: 862-872 (1989) and Stallings et al., Genomics, 13: 332-338 (1992)). However, Stallings et al., did utilize a synthetic 35-mer for the identification and characterization of CH16LAR (lies on chromosome 16) sequences though this was not an ISH or FISH assay (See: Stallings et al., Genomics, 13: 332-338 (1992) at the section entitled "Identification And Characterization Of CH16LAR Sequences" beginning p. 336, col. 1). A PCR assay has been developed to assay chromosome 16 for loss of heterozygosity though this is not a probe-based assay (See: Kihana et al., Jpn. J. Cancer Res., 87: 1184-1190 (1996). Analysis of alpha satellite DNA of chromosomes 17 and 18 have utilized DNA probes of hundreds to thousands of nucleotides in length (See: Waye et al, Molecular and Cellular Biology, 6: 3156-3165 (1986) and Alexandrov et al., Genomics 11: 15-23 (1991), respectively).

The methods thus far described all relate to the analysis of chromosomes X, Y, 1, 2, 6, 10 16, 17 or 18 using conventional nucleic acid based assay formats. However, the FISH analysis of human chromosome 5 has been described using a 30-mer synthetic oligonucleotide probe (See: Matera et al., Genomics, 18: 729-731 (1993) directed to the centromeric region. This is the only example, of which Applicant is aware, of using a synthetic nucleic acid in a FISH format to identify a human chromosome.

Despite its name, Peptide Nucleic Acid (PNA) is neither a nucleic acid, a peptide nor is it even an acid. Peptide Nucleic Acid (PNA) is a non-naturally occurring polyamide that can hybridize to nucleic acid (DNA and RNA) with sequence specificity (See U.S. Pat. No. 5,539,082 and Egholm et al., Nature 365:566-568 (1993)). Being a non-naturally occurring molecule, unmodified PNA is not known to be a substrate for the enzymes that are known to degrade peptides or nucleic acids. Therefore, PNA should be stable in biological samples, as well as have a long shelf-life. Unlike nucleic acid hybridization that is very dependent on ionic strength, the hybridization of a PNA with a nucleic acid is fairly independent of ionic strength and is favored at low ionic strength, conditions that strongly disfavor the hybridization of nucleic acid to nucleic acid (Egholm et al., Nature, at p. 567). The effect of ionic strength on the stability and conformation of PNA complexes has been extensively investigated (Tomac et al., J. Am. Chem. Soc. 118: 5544-5552 (1996)). Sequence discrimination is more efficient for PNA recognizing DNA than for DNA recognizing DNA (Egholm et al., Nature, at p. 566). However, the advantages in point mutation discrimination with non-nucleic acid probes, as compared with DNA probes, in a hybridization assay, appears to be somewhat sequence dependent (Nielsen et al., Anti-Cancer Drug Design 8:53-65, (1993) and Weiler et al., Nucl. Acids Res. 25: 2792-2799 (1997)).

Though they hybridize to nucleic acid with sequence specificity (See: Egholm et al., Nature, at p. 567), PNAs have been slow to achieve commercial success at least partially due to cost, sequence specific properties/problems associated with solubility and sell-aggregation (See: Bergman, F., Bannwarth, W. and Tam, S., Tett. Lett. 36:6823-6826 (1995), Haaima, G., Lohse, A., Buchardt, O. and Nielsen, P. E., Angew. Chem. Int. Ed. Engl. 35:1939-1942 (1996) and Lesnik, E., Hassman, F., Barbeau, J., Teng, K. and Weiler, K., Nucleosides & Nucleotides 16:1775-1779 (1997) at p 433, col. 1, ln. 28 through col. 2, ln. 3) as well as the uncertainty pertaining to non-specific interactions that might occur in complex systems such as a cell (See: Good, L. et al., *Antisense & Nucleic Acid Drug Development* 7:431-437 (1997)). Consequently, their unique properties clearly demonstrate that PNA is not the equivalent of a nucleic acid in either structure or function. Thus, PNA probes need to be evaluated for performance and optimization to thereby confirm whether they can be used to specifically and reliably detect a particular nucleic acid target sequence, particularly when the target sequence exists in a complex sample such as a cell, tissue or organism.

PNA probes have been demonstrated as being useful for the detection of rRNA in ISH and FISH assays (See: WO95/32305 and WO97/18325). PNA probes have also been used in the analysis of mRNA (e.g. Kappa Light Chain), viral nucleic acid (e.g. human papillomavirus) and the analysis of centromeric sequences in human chromosomes. Importantly, a PNA probe has also been used to detect human X chromosome specific sequences in a PNA-FISH format (See: WO97/18325, now U.S. Pat. No. 5,888,733). The ISH based analysis of eukaryotic chromosomes and cells using polyamide nucleic acids has also been suggested (See: U.S. Pat. No. 5,888,734).

The analysis of the telomere length of human chromosomes has been demonstrated using PNA probes in a FISH assay (See: Lansdorp et al., Human Mol. Genetics, 5: 685-691 (1996) as well as WO97/14026). Telomere length was measurable since the intensity of fluorescence from the terminus of the chromosome was shown to be proportional to the number of hybridized PNA probes and therefore proportional to the length of the telomere.

Similarly, the analysis of trinucleotide repeats in chromosomal DNA using appropriate PNA probes has been suggested (See: WO97/14026). Subsequently, DNA and PNA probes were used to examine cells for genetic defects associated with expansion of trinucleotide repeats which manifest as the disease known as human myotonic dystrophy (See: Taneja, *Biotechniques*, 24: 472-476 (1998)). The molecular basis of myotonic dystrophy (DM) is an extreme expansion of CTG repeat sequences in the 3'-UTR of the transcripts for the myotonin protein kinase (DMPK) gene. The severity and age of onset of this disease is known to be proportional to the length of the repeat expansion. The intensity of fluorescence from PNA probes hybridized to the targeted repeats could be used to quantify the length of the expansion repeat. This suggests the possibility of expansion repeat quantitation in a manner useful to confirm the diagnosis of genetic disease and possibly quantifying the age of onset and anticipated severity of the disease.

The Applicant is unaware of any previously described use of peptide nucleic acid (PNA) probes for the detection, identification or enumeration of chromosomes Y, 1, 2, 3, 4, 6, 7, 8, 9, 10, 11, 12, 13, 16, 17, 18, 20 and 21.

In summary, any methods, kits or compositions that could improve the specificity, sensitivity and reliability of probe-based assays for the detection of chromosomes X, Y, 1, 2, 3, 4, 6, 7, 8, 9, 10, 11, 12, 13, 16, 17, 18, 20 and 21 would be a useful advance in the state of the art particularly where the methods were uniformly applicable to probes of all or substantially all sequence variations. Moreover, the methods, kits or compositions would be particularly useful if they could provide for the rapid, reliable, accurate, sensitive and automated multiplex analysis of samples for the presence, absence or number of chromosomes X, Y, 1, 2, 3, 4, 6, 7, 8, 9, 10, 11, 12, 16, 17, 18 and 20, as well as 13/21 as a pair. It would be most useful if the methods, kits and compositions were suitable for the simultaneous analysis of some or all of the human chromosomes in the same assay.

SUMMARY OF THE INVENTION

This invention is directed to non-nucleic acid probes, probe sets, methods and kits useful for detecting, identifying and/or quantitating human chromosomes X, Y, 1, 2, 3, 4, 6, 7, 8, 9, 10, 11, 12, 16, 17, 18, and/or 20, as well as 13/21 as a pair, in a sample. Non-nucleic acid probes include peptide nucleic acid (PNA) probes as well as other probes that comprise an uncharged or positively charged backbone. The non-nucleic acid probes of this invention comprise probing nucleobase sequences that specifically hybridize with target sequences within the human chromosome or chromosomes sought to be detected. The preferred probing nucleobase sequence of the non-nucleic acid probes useful for detecting, identifying and/or quantitating a particular human chromosome or chromosomes are listed in Table 1.

In preferred embodiments, non-nucleic acid probes are organized into a set that is designed to detect, identify or quantitate, individually or together with other chromosomes, each of chromosomes X, Y, 1, 2, 3, 4, 6, 7, 8, 9, 10, 11, 12, 16, 17, 18 and/or 20, as well as 13/21 as a pair, that may be present in the sample. In a most preferred embodiment, a probe set is suitable for the specific detection, identification and/or quantitation of the total number of each of human chromosomes X, Y, 1, 2, 3, 4, 6, 7, 8, 9, 10, 11, 12, 16, 17, 18 and/or 20, as well as 13/21 as a pair, in a sample of interest. Preferably, the probes or probe sets are integrated into an assay used for the simultaneous detection, identification and/or quantitation of some or all human chromosomes. Most preferably, the assay is an automated PNA-ISH or PNA-FISH assay and in the most preferred embodiments the assay is automated and performed using either a slide scanner based analysis system, microscope and camera (e.g. CCD camera) or a flow cytometer.

This invention is further directed to a method suitable for detecting, identifying and/or quantitating human chromosomes X, Y, 1, 2, 3, 4, 6, 7, 8, 9, 10, 11, 12, 16, 17, 18 and/or 20, as well as 13/21 as a pair, that may be present in the sample. The method comprises contacting the sample with one or more non-nucleic acid probes, wherein suitable probes are described herein. According to the method, the presence, absence or number, individually or together with other chromosomes, of human chromosomes X, Y, 1, 2, 3, 4, 6, 7, 8, 9, 10, 11, 12, 16, 17, 18 and/or 20, as well as 13/21 as a pair, in the sample is then detected, identified and/or quantitated. Detection, identification and/or quantitation of chromosomes X, Y, 1, 2, 3, 4, 6, 7, 8, 9, 10, 11, 12, 16, 17, 18 and/or 20, as well as 13/21 as a pair, is made possible by correlating the hybridization, under suitable hybridization conditions or suitable in-situ hybridization conditions, of the probing nucleobase sequence of a non-nucleic acid probe to the target sequence of the chromosome sought to be detected to thereby confirm the presence, absence or quantity of one or more the chromosomes sought to be detected. Furthermore, the method can be multiplexed to provide specific detection, identification and/or quantitation of each of chromosomes X, Y, 1, 2, 3, 4, 6, 7, 8, 9, 10, 11, 12, 16, 17, 18 and/or 20, as well as 13/21 as a pair, in a single assay provided that the non-nucleic acid probes for a particular chromosome or chromosome pair are independently detectable from probes for the other chromosomes in the assay. In a preferred embodiment, non-nucleic acid probes used to detect each of chromosomes X, Y, 1, 2, 3, 4, 6, 7, 8, 9, 10, 11, 12, 16, 17, 18 and/or 20, as well as 13/21 as a pair, are each labeled with one or more independently detectable fluorophores to thereby enable correlation of the presence of signal from a particular fluorophore, or set of fluorophores, with the presence of each of chromosomes X, Y, 1, 2, 3, 4, 6, 7, 8, 9, 10, 11, 12, 13, 16, 17, 18 or 20, as well as 13/21 as a pair. Preferably, the assay is used for the simultaneous detection of all human chromosomes (a multiplex assay) and most preferably the assay is an automated PNA-FISH assay. Most preferably, the assay is automated and performed using either a slide scanner based analysis system, microscope and camera (e.g. CCD camera) or a flow cytometer.

In yet another embodiment, this invention is directed to kits suitable for performing an assay that detects the presence, absence and/or number of human chromosomes X, Y, 1, 2, 3, 4, 6, 7, 8, 9, 10, 11, 12, 13, 16, 17, 18, 20 and/or 21 in a sample. The kits of this invention comprise one or more non-nucleic acid probes and other reagents or compositions that are selected to perform an assay or otherwise simplify the performance of an assay. In a preferred embodiment, non-nucleic acid probes of the kit that are used to detect a particular chromosome or chromosomes are independently detectable. In a preferred embodiment, different non-nucleic acid probes of the kit are labeled with one or more independently detectable fluorophores to thereby enable correlation of the presence of signal from a particular fluorophore, or set of fluorophores, with the presence of each of chromosomes X, Y, 1, 2, 3, 4, 6, 7, 8, 9, 10, 11, 12, 16, 17, 18 and/or 20, as well as 13/21 as a pair. Preferably, the kits are used in an assay suitable for simultaneous detection, identification and/or quantitation of some or all human chromosomes and most preferably the assay is an automated PNA-FISH assay. Most preferably, the assay is automated and performed using either a slide scanner based analysis system, microscope and camera (e.g. CCD camera) or a flow cytometer.

In still another embodiment, this invention is directed to a multiplex assay suitable for detecting, identifying and/or enumerating at least two different human chromosomes in the same sample and in the same assay using least two non-nucleic acid probes that are independently detectable. In preferred embodiments, each of the two or more probes can detect the presence, absence and/or number of human chromosomes X, Y, 1, 2, 3, 4, 6, 7, 8, 9, 10, 11, 12, 16, 17, 18 and/or 20, as well as 13/21 as a pair, in the same sample and in the same assay. Preferably, the multiplex assay is a PNA-ISH or PNA FISH assay.

In still one more embodiment, this invention is directed to non-nucleic acid probes comprising two or more linked independently detectable moieties wherein the combination of the two or more independently detectable moieties is used to identify a particular probe/target sequence hybrid since the combination of the two or more linked moieties is unique. Preferably, the independently detectable moieties are independently detectable fluorophores.

In yet another embodiment, this invention is directed to probe sets, methods and kits suitable for the simultaneous and specific detection of two or more chromosomes such that at least two the individual probes of the probe set or kit, that is used in the method, hybridize to all of the two or more specific chromosomes sought to be detected. Preferably the probe sets, methods and kits pertain to the simultaneous and specific detection of chromosomes 13 and 21 as a pair (See: FIG. 21).

In still another embodiment, this invention is directed to probe sets, methods and kits designed specifically for prenatal analysis. Preferably, the probes sets, methods and kits for prenatal analysis are specific for the detection, identification and enumeration of human chromosomes X, Y, 18 and 13/21 as a pair. Most preferably the prenatal analysis is a multiplex analysis wherein chromosomes X, Y and 18 are detected as individual chromosomes using a unique label and chromosomes 13 & 21 are detected as a pair using yet another unique label. In this manner, conditions of aneuploidy and polyploidy for these individual chromosomes of prenatal significance can be rapidly detected using the standard PNA-ISH and PNA-FISH methods described herein.

The non-nucleic acid probes, probe sets, methods and kits of this invention have been demonstrated to be specific for human chromosomes X, Y, 1, 2, 3, 4, 7, 6, 9, 8, 10, 11, 12, 16, 17, 18 and 20, as well as 13/21 as a pair. Moreover, the assays described herein are rapid (with a sample containing fixed cells, the assay can be completed in 90 minutes or less), sensitive, reliable and generally applicable to probes of significantly different nucleobase sequence and variable PNA probe length. Assays can be used to accurately detect, identify and/or quantitate each of the total number of human chromosomes X, Y, 1, 2, 3, 4, 6, 7, 8, 9, 10, 11, 12, 16, 17, 18 and/or 20, as well as 13/21 as a pair, that is present in a sample containing all other human chromosomes. Non-limiting examples of typical samples include cells, tissues (including bone marrow), spermatozoa, ova, blastomeres, oocysts, buccal cells and chorinic ville. Most preferably, the methods, kits and compositions of this invention are suitable for the simultaneous detection, identification and/or quantitation of all human chromosomes in a sample. Most preferably, the assay is automated and performed using either a slide scanner based analysis system, microscope and camera (e.g. CCD camera) or a flow cytometer.

The non-nucleic acid probes, probe sets, methods and kits of this invention can be used to detect or identify chromosome related abnormalities. Non-limiting examples of chromosome related abnormalities which can be detected using this invention include aneuploidy karyotypes and polyploidy karyotypes. Additionally, the non-nucleic acid probes, probe sets, methods and kits of this invention are particularly useful for preimplantation diagnosis, for prenatal screening or for use in clinical diagnostic applications.

BRIEF DESCRIPTION OF THE DRAWINGS

General Note: For FIGS. 1, 2, 3, 4, 5, 8, 9 and 19, the composite digital image was obtained with each of the blue, green and red filters of a CCD camera attached to a microscope. For FIGS. 6, 7, 10, 11 and 13-18 and 20-21 the composite digital image was obtained with each of the blue and green filters of a CCD camera attached to a microscope. For FIG. 12, the filters are as described in Example 10.

DETAILED DESCRIPTION OF THE INVENTION

Figure 1:
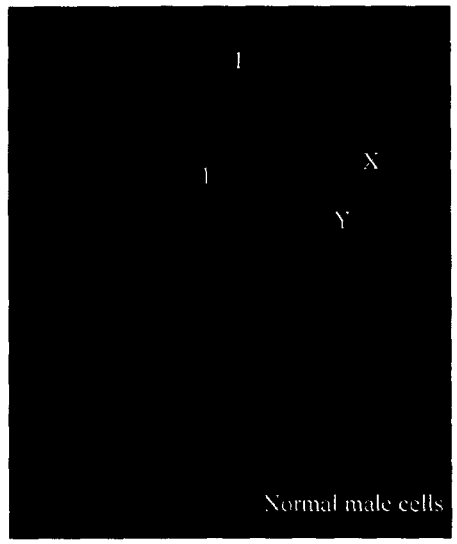
In FIG. 1 chromosomes X, Y and 1 are clearly detectable in the visible interphase nuclei and metaphase spreads. The perfectly paired sets of chromosomes indicate that these cells come from a normal human male.

1. Definitions a. As used herein, the term "nucleobase" means those naturally occurring and those non-naturally occurring heterocyclic moieties commonly known to those who utilize nucleic acid technology or utilize peptide nucleic acid technology to thereby generate polymers that can sequence specifically bind to nucleic acids.

b. As used herein, the term "nucleobase sequence" means any segment of a polymer that comprises nucleobase containing subunits. Non-limiting examples of suitable polymers or polymers segments include oligodeoxynucleotides, oligoribonucleotides, peptide nucleic acids, nucleic acid analogs, nucleic acid mimics, linked polymers or chimeras.

c. As used herein, the term "target sequence" means the nucleic acid sequence of a specific chromosome that is sought to be detected in an assay and to which at least a portion of the probing nucleobase sequence of the chromosome specific non-nucleic acid probe is designed to hybridize.

d. As used herein, the term "non-nucleic acid probe" means a probe comprising a probing nucleobase sequence that is designed to hybridize to at least a portion of the target sequence and is further characterized in that it comprises a neutral or positively charged backbone under suitable hybridization conditions or suitable in-situ hybridization conditions. A preferred non-limiting example of a non-nucleic acid probe is a peptide nucleic acid (PNA) probe.

e. As used herein, the term "peptide nucleic acid" or "PNA" means any oligomer, linked polymer or chimeric oligomer, comprising two or more PNA subunits (residues), including any of the polymers referred to or claimed as peptide nucleic acids in U.S. Pat. Nos. 5,539,082, 5,527,675, 5,623,049, 5,714,331, 5,736,336, 5,773,571, 5,786,461, 5,837,459, 5,891,625, 5,972,610 and 5,986,053; all of which are herein incorporated by reference. The term "peptide nucleic acid" or "PNA" shall also apply to polymers comprising two or more subunits of those nucleic acid mimics described in the following publications: Diderichsen et al., *Tett. Lett.* 37: 475-478 (1996); Fujii et al., *Bioorg. Med. Chem. Lett.* 7: 637-627 (1997); Jordan et al., *Bioorg. Med. Chem. Lett.* 7: 687-690 (1997); Krotz et al., *Tett. Lett.* 36: 6941-6944 (1995); Lagriffoul et al., *Bioorg. Med. Chem. Lett.* 4: 1081-1082 (1994); Lowe et al., *J. Chem. Soc. Perkin Trans.* 1, (1997) 1: 539-546; Lowe et al., *J. Chem. Soc. Perkin Trans.* 11: 547-554 (1997); Lowe et al., *J. Chem. Soc. Perkin Trans.* 1 1:5 55-560 (1997); Petersen et al., *Bioorg. Med. Chem. Lett.* 6: 793-796 (1996); Diederichsen, U., *Bioorganic & Med. Chem. Lett.,* 8: 165-168 (1998); Cantin et al., *Tett. Lett.,* 38: 4211-4214 (1997); Ciapetti et al., *Tetrahedron,* 53: 1167-1176 (1997); Lagriffoule et al., *Chem. Eur. J.,* 3: 912-919 (1997) and the Peptide-Based Nucleic Acid Mimics (PENAMs) of Shah et al as disclosed in WO96/04000.

In preferred embodiments, a PNA is a polymer comprising two or more subunits of the formula:

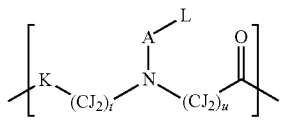

wherein, each J is the same or different and is selected from the group consisting of H, $R^1$, $OR^1$, $SR^1$, $NHR^1$, $NR^1_2$, F, Cl, Br and I. Each K is the same or different and is selected from the group consisting of O, S, NH and $NR^1$. Each $R^1$ is the same or different and is an alkyl group having one to five carbon atoms which may optionally contain a heteroatom or a substituted or unsubstituted aryl group. Each A is selected from the group consisting of a single bond, a group of the formula; —$(CJ_2)_s$- and a group of the formula; —$(CJ_2)_sC(O)$—, wherein, J is defined above and each s is an integer from one to five. The integer t is 1 or 2 and the integer u is 1 or 2. Each L is the same or different and is independently selected from the group consisting of J, adenine, cytosine, guanine, thymine, uridine, 5-methylcytosine, 2-aminopurine, 2-amino-6-chloropurine, 2,6-diaminopurine, hypoxanthine, pseudoisocytosine, 2-thiouracil, 2-thiothymidine, other naturally occurring nucleobase analogs, other non-naturally occurring nucleobases, substituted and unsubstituted aromatic moieties, biotin, fluorescein and dabcyl. In the most preferred embodiment, a PNA subunit consists of a naturally occurring or non-naturally occurring nucleobase attached to the aza nitrogen of the N-[2-(aminoethyl)]glycine backbone through a methylene carbonyl linkage.

f. As used herein, the terms "label" and "detectable moiety" shall be interchangeable and refers to moieties that can be attached to a non-nucleic acid probe, PNA probe, antibody or antibody fragment to thereby render the probe, antibody or antibody fragment detectable by an instrument or method.

g. As used herein, the term "chimera" or "chimeric oligomer" means an oligomer comprising two or more linked subunits that are selected from different classes of subunits. For example, a PNA/DNA chimera would comprise at least two PNA subunits linked to at least one 2'-deoxyribonucleic acid subunit (For exemplary methods and compositions related to PNA/DNA chimera preparation See: WO96/40709). Exemplary component subunits of the chimera are selected from the group consisting of PNA subunits, naturally occurring amino acid subunits, DNA subunits, RNA subunits and subunits of analogues or mimics of nucleic acids.

h. As used herein, the term "linked polymer" means a polymer comprising two or more polymer segments that are linked by a linker. The polymer segments that are linked to form the linked polymer are selected from the group consisting of an oligodeoxynucleotide, an oligoribonucleotide, a peptide, a polyamide, a peptide nucleic acid (PNA) and a chimera.

2. Description

I. General:
PNA Synthesis:
Methods for the chemical assembly of PNAs are well known (See: U.S. Pat. Nos. 5,539,082, 5,527,675, 5,623,049, 5,714,331, 5,736,336, 5,773,571, 5,786,461, 5,837,459, 5,891,625, 5,972,610 or 5,986,053, herein incorporated by reference). Chemicals and instrumentation for the support bound automated chemical assembly of peptide nucleic acids are now commercially available. Both labeled and unlabeled PNA oligomers are likewise available from commercial vendors of custom PNA oligomers. Chemical assembly of a PNA is analogous to solid phase peptide synthesis, wherein at each cycle of assembly the oligomer possesses a reactive alkyl amino terminus that is condensed with the next synthon to be added to the growing polymer. Because standard peptide chemistry is utilized, natural and non-natural amino acids are routinely incorporated into a PNA oligomer. Because a PNA is a polyamide, it has a C-terminus (carboxyl terminus) and an N-terminus (amino terminus). For the purposes of the design of a hybridization probe suitable for antiparallel binding to the target sequence (the preferred orientation), the N-terminus of the probing nucleobase sequence of the PNA probe is the equivalent of the 5'-hydroxyl terminus of an equivalent DNA or RNA oligonucleotide.

PNA Labeling:
Preferred non-limiting methods for labeling non-nucleic acid probes and PNAs are described in WO98/24933, WO99/22018, WO99/21881; copending and co-owned applications U.S. Ser. No. 09/179,298, U.S. Ser. No. 09/179,162, U.S. Ser. No. 09/225,048 and U.S. Ser. No. 09/275,848 (herein incorporated by reference), the priority documents listed as related applications herein incorporated by reference, the examples section of this specification or are otherwise well known in the art of PNA synthesis.

Labels:
Non-limiting examples of detectable moieties (labels) suitable for labeling non-nucleic acid probes, PNAs or antibodies used in the practice of this invention would include a dextran conjugate, a branched nucleic acid detection system, a chromophore, a fluorophore, a spin label, a radioisotope, an enzyme, a hapten, an acridinium ester and a chemiluminescent compound. Other suitable labeling reagents and preferred methods of attachment would be recognized by those of ordinary skill in the art of PNA, peptide or nucleic acid synthesis.

Preferred haptens include 5(6)-carboxyfluorescein, 2,4-dinitrophenyl, digoxigenin, and biotin.

Preferred fluorochromes (fluorophores) include 5(6)-carboxyfluorescein (Flu), 6-((7-amino-4-methykoumarin-3-acetyl)amino)hexanoic acid (Cou), 5(and 6)-carboxy-X-rhodamine (Rox), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.) or the Alexa dye series (Molecular Probes, Eugene, Oreg.).

Preferred enzymes include polymerases (e.g. Taq polymerase, Klenow DNA polymerase, T7 DNA polymerase, Sequenase, DNA polymerase 1 and phi29 polymerase), alkaline phosphatase (AP), horseradish peroxidase (HRP) and most preferably, soy bean peroxidase (SBP).

Detectable and Independently Detectable Moieties/Multiplex Analysis:
In preferred embodiments of this invention, a multiplex hybridization assay is performed. In a multiplex assay, numerous conditions of interest are simultaneously examined. Multiplex analysis relies on the ability to sort sample components or the data associated therewith, during or after the assay is completed. In preferred embodiments of the invention, one or more distinct independently detectable moieties are used to label two or more different probes used in an assay. The ability to differentiate between and/or quantitate each of the independently detectable moieties provides the means to multiplex a hybridization assay because the data that correlates with the hybridization of each distinctly (independently) labeled probe to a particular target sequence can be correlated with the presence, absence or quantity of each of two or more chromosomes sought to be detected in the sample. Consequently, the multiplex assays of this invention may be used to simultaneously detect the presence, absence and/or number of two or more chromosomes in the same sample and in the same assay.

Spacer/Linker Moieties:

Generally, spacers are used to minimize the adverse effects that bulky labeling reagents might have on hybridization properties of probes. Linkers typically induce flexibility and randomness into the probe or otherwise link two or more nucleobase sequences of a probe or component polymer. Preferred spacer/linker moieties for the nucleobase polymers of this invention consist of one or more aminoalkyl carboxylic acids (e.g. aminocaproic acid) the side chain of an amino acid (e.g. the side chain of lysine or ornithine) natural amino acids (e.g. glycine), aminooxyalkylacids (e.g. 8-amino-3,6-dioxaoctanoic acid), alkyl diacids (e.g. succinic acid), alkyloxy diacids (e.g. diglycolic acid) or alkyldiamines (e.g. 1,8-diamino-3,6-dioxaoctane). Spacer/linker moieties may also incidentally or intentionally be constructed to improve the water solubility of the probe (For example see: Gildea et al., *Tett. Lett.* 39: 7255-7258 (1998)). Preferably, a spacer/linker moiety comprises one or more linked compounds having the formula: $-Y-(O_m-(CW_2)_n)_o-Z-$. The group Y is selected from the group consisting of: a single bond, $-(CW_2)_p-$, $-C(O)(CW_2)_p-$, $-C(S)(CW_2)_p-$ and $-S(O_2)(CW_2)_p$. The group Z has the formula NH, $NR^2$, S or O. Each W is independently H, $R^2$, $-OR^2$, F, Cl, Br or I; wherein, each $R^2$ is independently selected from the group consisting of: $-CX_3$, $-CX_2CX_3$, $-CX_2CX_2CX_3$, $-CX_2CX(CX_3)_2$, and $-C(CX_3)_3$. Each X is independently H, F, Cl, Br or I. Each m is independently 0 or 1. Each n, and p are independently whole numbers from 0 to 10.

Hybridization Conditions/Stringency:

Those of ordinary skill in the art of nucleic acid hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a probe/target combination is often found by the well known technique of fixing several of the aforementioned stringency factors and then determining the effect of varying a single stringency factor. The same stringency factors can be modulated to thereby control the stringency of hybridization of a non-nucleic acid probe or PNA probe to a nucleic acid, except that the hybridization of a PNA is fairly independent of ionic strength. Optimal stringency for an assay may be experimentally determined by examination of each stringency factor until the desired degree of discrimination is achieved.

Suitable Hybridization Conditions:

Generally, the more closely related the background causing nucleic acid contaminates are to the target sequence, the more carefully stringency must be controlled. Blocking probes may also be used as a means to improve discrimination beyond the limits possible by mere optimization of stringency factors. Suitable hybridization conditions will thus comprise conditions under which the desired degree of discrimination is achieved such that an assay generates an accurate (within the tolerance desired for the assay) and reproducible result. Aided by no more than routine experimentation and the disclosure provided herein, those of skill in the art will easily be able to determine suitable hybridization conditions for performing assays utilizing the methods and compositions described herein. Suitable in-situ hybridization conditions are those conditions suitable for performing an in-situ hybridization procedure. Thus, suitable in-situ hybridization conditions will become apparent to those of skill in the art by using the disclosure provided herein; with or without additional routine experimentation.

Blocking Probes:

Blocking probes are nucleic acid or non-nucleic acid probes that can be used to suppress the binding of the probing nucleobase sequence of the probing polymer to a non-target sequence. Preferred blocking probes are PNA probes (See: Coull et al., WIPO publication No. WO98/24933). Typically blocking probes are closely related to the probing nucleobase sequence and preferably they comprise a point mutation of the probing segment. It is believed that blocking probes operate by hybridization to the non-target sequence to thereby form a more thermodynamically stable complex than is formed by hybridization between the probing nucleobase sequence and the non-target sequence. Formation of the more stable and preferred complex blocks formation of the less stable non-preferred complex between the probing nucleobase sequence and the non-target sequence. Thus, blocking probes can be used with the methods, kits and compositions of this invention to suppress the binding of the nucleic acid or non-nucleic acid probe to a non-target sequence which might be present and interfere with the performance of the assay. Blocking probes are particularly advantageous in single point mutation discrimination.

Probing Nucleobase Sequence:

The probing nucleobase sequence of a non-nucleic acid probe of this invention is the sequence recognition portion of the construct. Therefore, the probing nucleobase sequence is designed to hybridize to at least a portion of the target sequence. Preferably, the probing nucleobase sequence hybridizes to the entire target sequence. Detection of probe hybridization can be correlated with the presence, absence or number of human chromosomes X, Y, 1, 2, 3, 4, 6, 7, 8, 9, 10, 11, 12, 16, 17, 18 or 20, as well as 13/21 as a pair, in a sample. Consequently, with due consideration of the requirements of a non-nucleic acid probe for the assay format chosen and the human chromosome or chromosomes sought to be detected, the length and nucleobase content of the probing nucleobase sequence of the non-nucleic acid probe will generally be chosen such that a stable complex is formed with the target sequence of the chromosome or chromosomes of interest, under suitable hybridization conditions or suitable in-situ hybridization conditions.

The non-nucleic acid probes of this invention are relatively short as compared with the nucleic acid probes (0.1 to 5 kb or larger) that have been typically been used in ISH or FISH assays for the detection of chromosomes. The non-nucleic acid probe suitable for the practice of this invention will preferably have a length of 10-30 subunits wherein the exact probing nucleobase sequence is at least ninety percent homologous to the nucleobase sequences listed in Table 1. Because the target is double standard chromosomal DNA, the complementary sequence to the probing nucleobase sequence listed in Table 1 with will also produce a suitable probe. Specifically, the probing nucleobase sequence of the non-nucleic acid probes of this invention will preferably be in the range of 15-25 subunits in length and most preferably 16-23 subunits in length. This invention contemplates that variations in the probing nucleobase sequences listed in Table 1 shall provide non-nucleic acid probes which are suitable for the specific detection of the identified chromosomes. Common variations include, truncations, deletions, insertions and frame shifts. Variation of the probing nucleobase sequences within the parameters described herein are considered to be an embodiment of this invention.

The most preferred probing nucleobase sequences are listed in Table 1. Non-nucleic acid probes comprising these particular probing nucleobase sequences have been observed by Applicant to be specific for the human chromosomes sought to be detected. By specific we mean that the Applicant, using a standard protocol and several different cell lines, has achieved a very high degree of hybridization specificity such that little or no detectable cross hybridization to other human chromosomes has been observed. This is most remarkable given that identical stringency conditions have been applied in all assays performed without regard to the substantial sequence and length differences of the non-nucleic acid probes identified in Tables 1 and 2.

The significant cross reaction between the nucleic acid probes can potentially lead to errors in automated analysis since these could erroneously be interpreted as aneuploidy or polyploidy karyotypes. With regard to multiplex analysis, the potential for errors will also increase since small amounts of cross hybridization will be cumulative. Thus, a large number of cross reactions to a single non-target chromosome can lead to a very significant non-specific signal in the assay that cannot easily be ignored, filtered or subtracted out as background.

The probing nucleobase sequence of a non-nucleic acid probe will preferably be exactly complementary to the target sequence. Alternatively, a substantially complementary probing nucleobase sequence might be used since it has been demonstrated that greater sequence discrimination can be obtained when utilizing probes wherein there exists one or more point mutations (base mismatch) between the probe and the target sequence (See: Guo et al., *Nature Biotechnology* 15:331-335 (1997).

The non-nucleic acid probes of this invention are further characterized in that the backbone of the probing nucleobase sequence of the probe is neutral or positively charged under suitable hybridization conditions or suitable in-situ hybridization conditions. Without intending to be bound to this hypothesis, it is believed that the neutral or positively charged backbone provides the probe with better access to the double stranded nucleic acid target sequence of the chromosome.

Probe Complexes:

In still another embodiment, two probes are designed to hybridize to the target sequence sought to be detected to thereby generate a detectable signal whereby the probing nucleobase sequence of each probe comprises the complement to half or approximately half of the complete target sequence of the chromosome sought to be detected in the assay. As a non-limiting example, the probing nucleobase sequences of the two probes might be designed using the assay as described in European Patent Application 849,363, entitled "Method of identifying a nucleic acid using triple helix formation of adjacently annealed probes" by H. Orum et al. (See: EPA 849,363). Using this methodology, the probes which hybridize to the target sequence need not be labeled since it is the probe complex formed by the annealing of the adjacent probes which is detected. Similar compositions comprised solely of PNA probes have been described in copending and commonly owned application U.S. Ser. No. 09/302,238, herein incorporated by reference.

II. Preferred Embodiments of the Invention a. Non-Nucleic Acid Probes

In one embodiment, this invention is directed to non-nucleic acid probes. The non-nucleic acid probes of this invention are suitable for detecting, identifying or quantitating human chromosomes X, Y, 1, 2, 3, 4, 6, 7, 8, 9, 10, 11, 12, 16, 17, 18 or 20, as well as 13/21 as a pair, in a sample or in the individual cells of a sample. General characteristics and attributes (e.g. length, labels, and linkers etc.) of the non-nucleic acid probes suitable for the detection, identification or quantitation of human chromosomes X, Y, 1, 2, 3, 4, 6, 7, 8, 9, 10, 11, 12, 16, 17, 18 or 20, as well as 13/21 as a pair, have been previously described herein (See the discussion under the section entitled: "General"). The preferred probing nucleobase sequences of non-nucleic acid probes of this invention are listed in Table 1.

TABLE 1

| Target Human Chromosome or Chromosomes | Probing Nucleobase Sequence | Seq. ID No. |
|---|---|---|
| X | CTT-CAA-AGA-GGT-CCA-CGA | 1 |
| X | AGG-GTT-CAA-CTG-TGT-GAC | 2 |
| X | GAA-ACT-TCT-GAG-TGA-TGA | 3 |
| X | CAG-TCA-TCG-CAG-AAA-ACT | 4 |
| X | AGA-TTT-CAC-TGG-AAA-CGG | 5 |
| X | GTT-ATG-GGA-AGG-TGA-TCC | 6 |
| X | TCG-AGC-CGC-AGA-GTT-TAA | 7 |
| X | CTA-TTT-AGC-GGG-CTT-GGA | 8 |
| X | TAC-AAG-GGT-GTT-GCA-AAC | 9 |
| Y | CCA-TAT-GCA-GTT-ATA-AGT-AGG | 10 |
| Y | TAT-TGT-ACC-AAG-CAG-AGT-ACC | 11 |
| Y | GGT-ATA-TAT-AAG-ATG-ACA-CAG-GA | 12 |
| Y | GTT-AGT-TAT-ATT-GGG-TGA-TAT-GT | 13 |
| Y | TCA-CAT-AAT-AGA-CAA-CAT-AC | 14 |
| Y | CAG-AAG-AGA-TTG-AAC-CTT | 15 |
| Y | GGC-ATA-GCA-CAT-AAC-ATG | 16 |
| 1 | AAT-CGT-CAT-CGA-ATG-AAT | 17 |
| 1 | CAT-TGA-ACA-GAA-TTG-AAT | 18 |
| 2 | GTT-TTC-AGG-GGA-AGA-TAT | 19 |
| 2 | TGT-GCG-CCC-TCA-ACT-AAC | 20 |
| 2 | GAA-GCT-TCA-TTG-GGA-TGT | 21 |
| 2 | CCA-ATA-AAA-GCT-ACA-TAG-A | 22 |
| 2 | GAA-AAA-GTT-TCT-GAC-ATT-GC | 23 |
| 2 | TAG-TTG-AAG-GGC-ACA-TCA | 24 |
| 2 | CAC-AAA-TAA-GAT-TCT-AAG-AAT | 25 |
| 2 | TCA-AAA-GAA-TGC-TTC-AAC-AC | 26 |
| 3 | ATA-ATT-AGA-CCG-GAA-TCA-T | 27 |
| 3 | GCT-GTT-TTC-TAA-AGG-AAA-G | 28 |
| 3 | AAG-ACT-TCA-AAG-AGG-TCC | 29 |
| 3 | TTT-GTC-AAG-AAT-TAT-AAG-AAG | 30 |
| 3 | CAA-GAT-TGC-TTT-TAA-TGG | 31 |
| 3 | TGT-GTA-TCA-ACT-CAC-GGA | 32 |
| 3 | CCT-CAC-AAA-GTA-GAA-ACT | 33 |
| 3 | GAA-AAA-GCA-GTT-ACT-GAG | 34 |
| 3 | TAA-TAA-TTA-GAC-GGA-ATC-AT | 35 |
| 3 | TTA-CAG-GGC-ATT-GAA-GCC | 36 |
| 3 | CAG-TTA-TGA-AGC-AGT-CTC | 37 |
| 3 | CAC-ACC-AGA-AAA-AGC-AGT | 38 |
| 3 | AAG-GGT-AAA-CAC-TGT-GAG | 39 |
| 3 | AGA-CAA-CGA-AAT-ATC-TTC-ATG | 40 |
| 3 | CTA-GCA-GTA-TGA-GGT-CAA | 41 |
| 3 | GCA-GAC-TTC-AGA-AAC-AGA | 42 |
| 3 | GGC-CTC-AAA-GAC-GTT-TAA | 43 |
| 3 | GTG-AAA-GTT-CCA-AGT-GAA | 44 |
| 3 | GAG-TGC-TTT-GAA-GCC-TAC | 45 |
| 3 | GAA-ACA-GCA-GAG-TTG-AAA | 46 |
| 3 | TGC-AGA-GAT-CAC-AAC-GTG | 47 |
| 3 | ACA-AAG-AAT-CAT-TCG-CAG | 48 |
| 3 | AGT-GTT-AGA-AAA-CTG-CTC | 49 |
| 4 | ACA-CGA-TTT-TGG-AAA-C AC | 119 |
| 4 | CGA-AAC-ATC-ACT-GAG-AGT | 120 |
| 4 | GGA-TGA-CAT-ATA-ATA-ACT-AG | 121 |
| 4 | GAA-TTG-AAC-ATT-CAC-TTT-GA | 122 |
| 4 | TAG-CTC-TGA-AGA-TTT-CGT | 123 |
| 4 | GAG-ATG-TTT-CCG-AGA-ATG | 124 |
| 4 | GTG-TAT-TCA-ACT-ACC-AGA | 125 |
| 4 | ACA-TTT-CTG-TTA-CAG-AGC | 126 |
| 4 | ATG-ACG-TAT-AAA-ATC-TAG-AG | 127 |
| 4 | ACG-AAC-ACA-GTT-GAA-CCT | 128 |
| 4 | CTC-ATA-AAA-ACC-AGA-AAG-AG | 129 |

TABLE 1-continued

| Target Human Chromosome or Chromosomes | Probing Nucleobase Sequence | Seq. ID No. |
|---|---|---|
| 6 | CTG-TTC-AGA-GTA-ACA-TGA | 50 |
| 6 | CCG-CTT-GGA-AAT-ACT-ACA | 51 |
| 6 | GAA-ATG-GAA-ATA-TCT-CCC-C | 52 |
| 6 | TCT-AGG-AGG-TCC-AAT-TAT | 53 |
| 6 | GAA-TTC-CCA-AGT-GGA-TAT | 54 |
| 6 | CTG-TAG-GTT-TAG-ATG-AAG | 55 |
| 6 | AAG-GAG-TGT-TTC-CCA-ACT | 56 |
| 6 | GGC-TTC-AAG-GCG-CTC-TAA | 57 |
| 6 | GCA-GAG-ACT-TCA-AAG-TGC | 58 |
| 6 | CAC-ACA-CAC-GGT-GGA-CCA | 59 |
| 6 | CAA-AGG-GAA-TGT-TCC-ATT | 60 |
| 6 | CAC-ATA-GCA-GTG-TTT-GAG | 61 |
| 6 | CTC-AAG-GCG-GTC-CAA-TTA | 62 |
| 6 | GAG-TCG-AAA-TGC-ACA-CAT | 63 |
| 6 | TAC-CAA-GAG-GAA-TGT-TGC | 64 |
| 7 | CAG-TTC-ATA-TGT-GCA-GTG | 130 |
| 7 | GGA-ATA-TCG-TCA-CCT-AAA | 131 |
| 7 | TGG-AGC-AAA-TTG-AAG-CCT | 132 |
| 7 | TGG-AGC-ACA-TTT-ATG-CCT | 133 |
| 7 | TGC-ATT-CTA-CTC-CCA-TAG | 134 |
| 7 | ACA-CTC-TGT-TTC-TAA-AAT-CT | 135 |
| 7 | GCA-GGC-GGA-TAT-TTA-GTA | 136 |
| 7 | AGC-GAT-TTG-ATG-CCA-ACA | 137 |
| 7 | TTG-CAA-ACG-GGG-TTT-CTT | 138 |
| 7 | CTT-TCA-TGC-TAG-ACA-GAA | 139 |
| 7 | CAA-AAA-AGT-TAC-TGA-GAA-C | 140 |
| 7 | AAA-ATG-CCA-CAG-CAA-GAG | 141 |
| 7 | GTT-TGA-AAA-CAC-ACT-GTT-TG | 142 |
| 7 | ATA-TGG-ACC-TGT-TTG-AGG | 143 |
| 7 | CAT-TGA-ATG-CTA-GAC-GGA | 144 |
| 8 | ACG-GGA-TGC-AAT-ATA-AAA | 65 |
| 8 | TGA-AGA-TTC-TGC-ATA-CGG | 66 |
| 8 | AAG-GTT-TGT-ACT-GAC-AGA | 67 |
| 8 | CTG-AAC-TAT-GGT-GAA-AAA | 68 |
| 8 | ACT-AAC-TGT-GCT-GAA-CAT | 69 |
| 8 | CCC-ATG-AAT-GCG-AGA-TAG | 70 |
| 9 | ATG-ATG-AAA-AAG-GTA-ATA | 145 |
| 9 | CAT-TCT-CAG-AAC-TGT-TTG | 146 |
| 10 | AAC-TGA-ACG-CAC-AGA-TGA | 71 |
| 10 | GGC-TAA-TCT-TTG-AAA-TTG-AAA | 72 |
| 10 | AGG-TGG-ATA-ATT-GGC-CCT | 73 |
| 10 | TGA-AGT-CCA-AAA-AAG-CAC | 74 |
| 10 | CTT-AGA-CAT-GGA-AAT-ATC | 75 |
| 10 | AAG-GGG-TCT-AAC-TAA-TCA | 76 |
| 10 | GTA-GTT-GTT-GAG-AAT-GAT | 77 |
| 11 | AAC-TTC-CCA-GAA-CTA-CAC | 78 |
| 11 | ATT-CTT-GAA-ATG-GAA-CAC | 79 |
| 11 | CTG-TGA-TTG-CTG-ATT-TGG | 80 |
| 11 | GTC-ATC-ACA-GGA-AAC-ATT | 81 |
| 11 | GAA-ATT-TCC-TGT-TGA-CAG-A | 82 |
| 11 | GTT-TGA-AAG-CTG-AAC-TAT-G | 83 |
| 12 | TCC-TGT-AAT-GTT-CGA-CAG | 84 |
| 12 | TCA-TAG-AAC-GCT-AGA-AAG | 85 |
| 12 | ACC-TTT-CTT-TTG-ATG-AAG-GA | 86 |
| 12 | CAA-ATA-TCA-CAA-AAA-GAG-GG | 87 |
| 12 | GAG-TTG-AAT-AGA-GGC-AAC | 88 |
| 12 | GGC-CAA-ATG-TAG-AAA-AGG | 89 |
| 12 | GCG-TTC-AAC-TCA-AGG-TGT | 90 |
| 12 | TGT-CCT-TTA-GAC-AGA-GCA | 91 |
| 12 | TGA-GAC-CAA-ATG-TAC-AAA-AG | 92 |
| 12 | GAA-TAC-TGA-GTA-AGT-TCT-TTG | 93 |
| 12 | AAC-TGC-ACA-AAT-AGG-GTG | 94 |
| 12 | TGG-AGA-CAC-TGT-GTT-TGT | 95 |
| 12 | CCA-GTT-GGA-GAT-TTC-AAT | 96 |
| 16 | GAA-GCC-TGC-CAG-TGG-ATA | 97 |
| 16 | TAC-AGC-ATT-CTG-GAA-ACC | 98 |
| 16 | CCA-GAC-ACT-GCG-TAG-TGA | 99 |
| 16 | ATA-TAA-TGC-TAG-AGG-GAG | 100 |
| 16 | AAA-AAC-AAG-ACA-AAC-TCG | 101 |
| 17 | ATT-TCA-GCT-GAC-TAA-ACA | 102 |
| 17 | AAC-GAA-TTA-TGG-TCA-CAT | 103 |
| 17 | GGT-GAC-GAC-TGA-GTT-TAA | 104 |
| 17 | TTT-GGA-CCA-CTC-TGT-GGC | 105 |
| 17 | AAC-GGG-ATA-ACT-GCA-CCT | 106 |
| 17 | TTT-GTG-GTT-TGT-GGT-GGA | 107 |
| 17 | AGG-GAA-TAG-CTT-CAT-AGA | 108 |

TABLE 1-continued

| Target Human Chromosome or Chromosomes | Probing Nucleobase Sequence | Seq. ID No. |
|---|---|---|
| 17 | ATC-ACG-AAG-AAG-GTT-CTG | 109 |
| 17 | CCG-AAG-ATG-TCT-TTG-GAA | 110 |
| 17 | AAA-GAG-GTC-TAC-ATG-TCC | 111 |
| 18 | TTC-CCG-TAA-CAA-CTA-TGC | 112 |
| 18 | TCC-CGT-AAC-AAC-TAG-GCA | 113 |
| 18 | AAA-AGG-AGT-GAT-CCA-ACC | 114 |
| 18 | TCC-CTT-TGG-TAG-AGC-AGG | 115 |
| 18 | ATT-TGA-GAT-GTG-TGT-ACT-CA | 116 |
| 18 | GCA-CTT-ACC-GGC-CTA-AG | 117 |
| 18 | CTC-AGA-AAC-TTA-CTC-GTG | 118 |
| 20 | ACA-GAA-CTA-AAC-CAT-CGT | 147 |
| 20 | TAG-GCC-AGC-TTG-GAG-GAT | 148 |
| 20 | CTA-GCT-GGG-AGG-ATT-T | 149 |
| 20 | TGT-GCC-TCA-ACT-GAC-A | 150 |
| 20 | TGC-TTT-GGG-ATG-TTT-CAA | 151 |
| 20 | GCA-ATG-TCA-GAA-CTT-TTT-TC | 152 |
| 13/21 | CCG-AAA-GAA-ATT-TGT-GGG | 153 |
| 13/21 | GAA-CAT-GGC-CTT-TCA-TAG | 154 |
| 13/21 | TCA-AGG-CGA-TCG-AAA-TGT | 155 |
| 13/21 | GAG-ACA-CAT-ATC-ACC-AAC | 156 |
| 13/21 | CAG-AAA-TTT-CTT-TCG-GAT-A | 157 |
| 13/21 | GAA-CAT-GGC-CTT-TCA-TAG | 158 |
| 13/21 | AGC-CAA-AGG-AGT-TGA-ACA | 159 |

Note: Apart from the functional examples described herein which have been performed to screen potential probe sequences and thereby confirm their practical specificity in an assay, the complementary target sequence to which the probing nucleobase sequences in Table 1 hybridize were examined using sequence alignment analysis of information currently available in Genbank. It is noteworthy that in the functional assay many of the sequences originally chosen did not prove to be highly specific despite alignment analysis indications that they should be specific to the chromosome sought to be detected.

The probing nucleobase sequences listed in Table 1 are complementary to target sequences that are highly repetitive within the chromosome sought to be detected. Since the chromosomal DNA is double stranded, the complement to the probing nucleobase sequences listed in Table 1 will also provide a probe suitable for hybridization to the complementary strand. Typically, the target sequence is repeated between 100 to 5000 times within the chromosome. Consequently, although each probe is typically labeled with a single detectable moiety, signal generated from the fluorophores (the preferred detectable moiety) concentrated on the chromosome sought to be detected with the non-nucleic acid probes of this invention is easily visible to the eye using a conventional fluorescence microscope.

Applicant has estimated that approximately 200 fluorophores concentrated in the chromosome are necessary to visualize a detectable signal using conventional microscopy. Consequently, it is preferable to choose non-nucleic acid probes directed to a target sequence which is repeated at least 200 times in the chromosome. Alternatively, non-nucleic acid probes can be chosen that have a target sequence which is repeated fewer than 200 times provided more than one probe to a particular chromosome is used in the assay. For example, two or more non-nucleic acid probes could be used provided that each target sequence was repeated one hundred times within the chromosome sought to be detected. Alternatively, multiple labels could be attached to each probe to thereby increase detectable signal by a factor commensurate with the number of attached labels and the number of available targets to thereby achieve the level of fluorescence intensity required to achieve a detectable signal. It is also anticipated that as more intense fluorophores are developed or more sensitive methods of detection become available, the number of target sequence repeats or number of probes per cocktail necessary to achieve a satisfactory level of signal in an assay for a particular chromosome will decrease.

The non-nucleic acid probes of this invention may comprise only a probing nucleobase sequence or may comprise additional moieties. Non-limiting examples of additional moieties include detectable moieties (labels), linkers, spacers, natural or non-natural amino acids, or other subunits of PNA, DNA or RNA. Additional moieties may be functional or non-functional in an assay. Generally however, additional moieties will be selected to be functional within the design of the assay in which the non-nucleic acid probe is to be used. The preferred non-nucleic acid probes of this invention are labeled with one or more detectable moieties. In a more preferred embodiment, one or more probes are labeled with two or more independently detectable moieties.

Preferred independently detectable moieties are independently detectable fluorophores. Preferred probes of this invention will also comprise solubility enhancer moieties such as those described in: Gildea et al., Tett. Lett. 39: 7255-7258 (1998) or copending and co-owned patent application U.S. Ser. No. 09/225,048, herein incorporated by reference. The solubility enhancers are typically used to enable the synthesis and purification of the PNA which otherwise may be insoluble or tend to self aggregate. The solubility enhancers are particularly useful in the synthesis and purification of the numerous labeled purine rich probes listed in Table 2.

In a most preferred embodiment of this invention, independently detectable moieties are used to label each of at least two different non-nucleic acid probes, whereby at least one probe is suitable for detecting one of chromosomes X, Y, 1, 2, 3, 4, 6, 7, 8, 9, 10, 11, 12, 16, 17, 18 or 20, as well as 13/21 as a pair, and at least one other probe is suitable for detecting another of chromosomes X, Y, 1, 2, 3, 4, 6, 7, 8, 9, 10, 11, 12, 16, 17, 18 or 20, as well as 13/21 as a pair, such that the independently detectable moieties can be used to independently detect, identify or quantitate each of at least two different chromosome types in the same assay. In certain preferred embodiments, one or more of the probes may comprise two or more independently detectable moieties wherein the combination of the two or more labels is unique in the assay and can be used to detect the presence or amount of the chromosome or chromosomes of interest in the sample. More specifically, the presence or amount of the unique combination of labels in the sample is indicative of the presence or amount of the probe/target sequence hybrid characteristic for the chromosome sought to be detected.

In preferred embodiments, the probes of this invention are used in in-situ hybridization (ISH) and fluorescence in-situ hybridization (FISH) assays. Excess probe used in an ISH or FISH assay typically must be removed so that the detectable moiety of specifically bound probes can be detected above the background signal that results from still present but unhybridized probe. Generally, the excess probe is washed away after the sample has been incubated with probe for a period of time. However, the use of "dark probes" are a preferred embodiment of this invention, since there is no requirement that excess "dark probe" be completely removed (washed away) from the sample since the unhybridized probe generates little or no detectable background in the assay.

As used herein, a "dark probe" shall be a probe that hybridizes to a target sequence to thereby cause a detectable change in at least one physical property of at least one attached label in a manner that can be used to detect, identify or quantitate the presence of an organism of interest in a sample of interest. Non-limiting examples of "dark probes" include nucleic acid Molecular Beacons (See: WO97/39008 and U.S. Pat. No. 5,925,517), PNA Molecular Beacons (See: WO99/21881 and U.S. Ser. No. 08/958,532 (abandoned) and copending and commonly owned U.S. Ser. No. 09/179,298, both incorporated herein by reference), Linear Beacons (See: WO99/22018 and copending and commonly owned U.S. Ser. No. 09/179,162, herein incorporated by reference) and probes comprising a reporter that interacts with the nucleic acid upon hybridization to thereby produce fluorescence. (See: WO97/45539). Thus, changes in signal in the assay utilizing a "dark probe" can be directly or indirectly correlated with hybridization of the probing nucleobase sequence to the target sequence of the chromosome of interest.

Detection of Chromosomes 13 & 21 as a Pair:

Based upon Applicant's investigations, there appears to very little distinction between the alpha satellite regions of chromosomes 13 and 21 such that short (<30 nucleobases in length) unique probes cannot be prepared to individually target these chromosomes. As a solution to this problem, non-nucleic acid probes of invention were prepared that are directed to both chromosomes 13 and 21 simultaneously. Since both chromosomes 13 and 21 are of prenatal significance, simultaneous detection of both chromosomes 13 and 21 allows for simple detection, identification and enumeration of these chromosomes in a single assay. The probing nucleobase sequence of suitable non-nucleic acid probes for the detection of chromosomes 13 and 21 are identified in Table 1. Moreover, a multiplex assay is simplified since fewer unique labels are required. Although specific probes were only designed for chromosomes 13 and 21 at this time, it is noted that probes can be prepared for other chromosomes having closely associated alpha satellite regions (e.g. chromosomes 14 and 22).

Unlabeled Non-Nucleic Acid Probes:

The probes of this invention need not be labeled with a detectable moiety to be operable within this invention. When using the probes of this invention it is possible to detect the probe/target sequence complex formed by hybridization of the probing nucleobase sequence of the probe to the target sequence. For example, a PNA/nucleic acid complex formed by the hybridization of a PNA probing nucleobase sequence to the target sequence could be detected using an antibody which specifically interacts with the complex under antibody binding conditions. Suitable antibodies to PNA/nucleic acid complexes as well as methods for their preparation and use are described in WIPO Patent Application WO95/17430 and U.S. Pat. No. 5,612,458, herein incorporated by reference. Antibodies to complexes formed with non-nucleic acid probes other than PNA can likewise be prepared using methods similar to those described in WIPO Patent Application WO95/17430 and U.S. Pat. No. 5,612,458.

The antibody/PNA/nucleic acid complex formed by interaction of the α-PNA/nucleic acid antibody with the PNA/nucleic acid complex can be detected by several methods. For example, the α-PNA/nucleic acid antibody could be labeled with a detectable moiety. Suitable detectable moieties have been previously described herein. Thus, the presence, absence or quantity of the detectable moiety is correlated with the presence, absence or quantity of the antibody/PNA/nucleic acid complex and the chromosome to be identified by the probing nucleobase sequence of the PNA probe. Alternatively, the antibody/PNA/nucleic acid complex is detected using a secondary antibody which is labeled with a detectable moiety. Typically the secondary antibody specifically binds to the α-PNA/nucleic acid antibody under antibody binding conditions. Thus, the presence, absence or quantity of the detectable moiety is correlated with the presence, absence or quantity of the antibody/antibody/PNA/nucleic acid complex and the chromosome to be identified by the probing nucleobase sequence of the probe. As used herein, the term antibody shall include antibody fragments that specifically bind to other antibodies or other antibody fragments.

Immobilization of Probes to a Surface:

One or more of the non-nucleic acid probes of this invention may optionally be immobilized to a surface for the detection identification or quantitation of human chromosomes X, Y, 1, 2, 3, 4, 6, 7, 8, 9, 10, 11, 12, 16, 17, 18 or 20, as well as 13/21 as a pair. Non-nucleic acid probes can be immobilized to the surface using the well known process of UV-crosslinking. More preferably, the non-nucleic acid probe is synthesized on the surface in a manner suitable for deprotection but not cleavage from the synthesis support (See: Weiler, J. et al, Hybridization based DNA screening on peptide nucleic acid (PNA) oligomer arrays., Nucl. Acids Res., 25: 2792-2799 (July, 1997)). In still another embodiment, one or more non-nucleic acid probes are covalently linked to a surface by the reaction of a suitable functional group on the probe with a functional group of the surface (See: Lester, A. et al, "PNA Array Technology": Presented at Biochip Technologies Conference in Annapolis (October, 1997)). This method is most preferred since the non-nucleic acid probes on the surface will typically be highly purified and attached using a defined chemistry, thereby minimizing or eliminating non-specific interactions.

Methods for the chemical attachment of probes to surfaces generally involve the reaction of a nucleophilic group, (e.g. an amine or thiol) of the probe to be immobilized, with an electrophilic group on the support to be modified. Alternatively, the nucleophile can be present on the support and the electrophile (e.g. activated carboxylic acid) present on the probe. Because native PNA possesses an amino terminus, a PNA will not necessarily require modification to thereby immobilize it to a surface (See: Lester et al., Poster entitled "PNA Array Technology").

Conditions suitable for the immobilization of a non-nucleic acid probe to a surface will generally be similar to those conditions suitable for the labeling of the polymer. The immobilization reaction is essentially the equivalent of labeling whereby the label is substituted with the surface to which the polymer is to be linked.

Numerous types of surfaces derivatized with amino groups, carboxylic acid groups, isocyantes, isothiocyanates and malimide groups are commercially available. Non-limiting examples of suitable surfaces include membranes, glass, controlled pore glass, polystyrene particles (beads), silica and gold nanoparticles.

Arrays of PNA Probes or Probe Sets:

Arrays are surfaces to which two or more probes have been immobilized each at a specified position. This invention is also directed to immobilized probes having probing nucleobase sequences judiciously chosen to interrogate (often using a capture assay) a sample to thereby detect the presence, absence or number of human chromosomes. Because the location and composition of each immobilized probe is known, arrays are generally useful for the simultaneously detection, identification or quantitation of two or more target sequences which may be present in the sample. Moreover, arrays of non-nucleic acid or PNA probes may be regenerated by stripping the hybridized nucleic acid after each assay, thereby providing a means to repetitively analyze numerous samples using the same array. Thus, arrays of non-nucleic acid or PNA probes may be useful for repetitive screening of samples for one or more chromosomes of interest. The arrays of this invention comprise at least one non-nucleic acid probe (as described herein) suitable for the detection, identification or quantitation of human chromosomes. Preferred probing nucleobase sequences for the immobilized non-nucleic acid probes are listed in Table 1.

Advantages Associated with Non-Nucleic Acid Probes:

Unlike oligonucleotide probes, non-nucleic acid probes lack a negative charge on the backbone of the nucleobase containing subunits and therefore they efficiently interact with the target sequence of the nucleic acid since there are no electrostatic forces which repel each other when the hybrid is formed. This allows for optimization of stringency conditions wherein a high degree of specificity of signal is achieved.

The non-nucleic acid probes of this invention also differ from the nucleic acid probes typically chosen for chromosome analysis since they are purified synthetic molecules that are highly defined and well characterized. Consequently, the non-nucleic acid probes or the mixtures of non-nucleic acid probes can be more easily reproduced than are the nucleic acid probes that are typically derived by enzymatic manipulation of nucleic acid starting materials. Thus, the non-nucleic acid probes or the mixtures of non-nucleic acid probes of this invention should be more homogenous from lot to lot thereby reducing the lot to lot performance variability often associated with nucleic acid probes.

b. Probe Sets

In another embodiment, this invention is directed to a probe set suitable for detecting, identifying or quantitating human chromosomes X, Y, 1, 2, 3, 4, 6, 7, 8, 9, 10, 11, 12, 16, 17, 18 or 20, as well as 13/21 as a pair, present in a sample or in the cells of a sample. General and preferred characteristics of non-nucleic acid probes suitable for preparing a probe set useful for the detection, identification or quantitation of said human chromosomes have been previously described herein. Preferred probing nucleobase sequences are listed in Table 1. The grouping of non-nucleic acid probes within sets characterized for specific detection of one, two or more of the identified human chromosomes is contemplated as a preferred embodiment of this invention. In preferred embodiments, one or more probe sets identified herein are combined with other probes to generate a probe set suitable for the detection, identification and/or enumeration of all human chromosomes in the same assay.

Probe sets of this invention shall comprise at least one non-nucleic acid probe but need not comprise only non-nucleic acid probes. For example, probe sets of this invention may comprise mixtures of non-nucleic acid probes and nucleic acid probes, provided however that a set comprises at least one non-nucleic acid probe as described herein. In preferred embodiments, some of the probes of the set are blocking probes composed of unlabeled PNA and/or nucleic acid oligomers.

Table 1 lists many alternative probing nucleobase sequences suitable for the detection, identification and/or quantitation of the identified human chromosomes of interest. Since alternative probing nucleobase sequences exist for the detection of any of the chromosomes, it is preferable to use a probe set containing two or more non-nucleic acid probes for the detection, identification and/or quantitation of a particular chromosome or chromosomes to thereby increase the detectable signal in the assay. In a preferred embodiment, all the probes of a set that are used to detect, identify and/or quantitate a particular chromosome or chromosomes will be labeled with the same independently detectable moiety or moieties and all probes of a set that are used to detect, identify and/or quantitate a different chromosome or chromosomes (e.g. 13/21 as a pair) in the same sample will be labeled with one or more different independently detectable moieties to thereby enable the independent detection of each of chromosomes X, Y, 1, 2, 3, 4, 6, 7, 8, 9, 10, 11, 12, 16, 17, 18 or 20, as well as 13/21 as a pair, in the same sample and in the same assay (a multiplex assay). One exemplary probe set would therefore comprise probes suitable for the independent detection, identification and/or quantitation of each of chromosomes X, Y, 1, 2, 3, 4, 6, 7, 8, 9, 10, 11, 12, 16, 17, 18 and 20, as well as 13/21 as a pair, that might be present in a sample. For example, a suitable probe set might therefore contain at least one non-nucleic acid probe suitable for detecting each of chromosomes X, Y, 1, 2, 3, 4, 6, 7, 8, 9, 10, 11, 12, 16, 17, 18 and 20, as well as 13/21 as a pair, but more preferably, the preferred probe set would contain non-nucleic acid probes such that most or all of the probing nucleobase sequences listed in Table 1 are represented.

Consequently, an exemplary probe set might therefore comprise at least one non-nucleic acid probe suitable for detecting the human X chromosome, wherein at least one probe of the set has a probing nucleobase sequence, at least a portion of which is at least ninety percent homologous to the nucleobase sequences, or there complements, which are selected from the group consisting of: CTT-CAA-AGA-GGT-CCA-CGA (Seq. ID No. 1); AGG-GTT-CAA-CTG-TGT-GAC (Seq. ID No. 2); GAA-ACT-TCT-GAG-TGA-TGA (Seq. ID No. 3); CAG-TCA-TCG-CAG-AAA-ACT (Seq. ID No. 4); AGA-TTT-CAC-TGG-AAA-CGG (Seq. ID No. 5); GTT-ATG-GGA-AGG-TGA-TCC (Seq. ID No. 6); TCG-AGC-CGC-AGA-GTT-TAA (Seq. ID No. 7); CTA-TTT-AGC-GGG-CTT-GGA (Seq. ID No. 8) and TAC-AAG-GGT-GTT-GCA-AAC (Seq. ID No. 9). The set would further comprise at least one non-nucleic acid probe suitable for detecting the human Y chromosome, wherein at least one probe of the set has a probing nucleobase sequence, at least a portion of which is at least ninety percent homologous to the nucleobase sequences, or there complements, which are selected from the group consisting of: CCA-TAT-GCA-GTT-ATA-AGT-AGG (Seq. ID No. 10); TAT-TGT-ACC-AAG-CAG-AGT-ACC (Seq. ID No. 11); GGT-ATA-TAT-AAG-ATG-ACA-CAG-GA (Seq. ID No. 12); GTT-AGT-TAT-ATT-GGG-TGA-TAT-GT (Seq. ID No. 13); TCA-CAT-AAT-AGA-CAA-CAT-AC (Seq. ID No. 14); CAG-AAG-AGA-TTG-AAC-CTT (Seq. ID No. 15) and GGC-ATA-GCA-CAT-AAC-ATG (Seq. ID No. 16). The set would further comprise at least one non-nucleic acid probe suitable for detecting human chromosome 1, wherein at least one probe of the set has a probing nucleobase sequence, at least a portion of which is at least ninety percent homologous to the nucleobase sequences, or there complements, which are selected from the group consisting of: AAT-CGT-CAT-CGA-ATG-AAT (Seq. ID No. 17) and CAT-TGA-ACA-GAA-TTG-AAT (Seq. ID No. 18). The set would further comprise at least one non-nucleic acid probe suitable for detecting human chromosome 2, wherein at least one probe of the set has a probing nucleobase sequence, at least a portion of which is at least ninety percent homologous to the nucleobase sequences, or there complements, which are selected from the group consisting of: GTT-TTC-AGG-GGA-AGA-TAT (Seq. ID No. 19); TGT-GCG-CCC-TCA-ACT-AAC (Seq. ID No. 20); GAA-GCT-TCA-TTG-GGA-TGT (Seq. ID No. 21); CCA-ATA-AAA-GCT-ACA-TAG-A (Seq. ID No. 22); GAA-AAA-GTT-TCT-GAC-ATT-GC (Seq. ID No. 23); TAG-TTG-AAG-GGC-ACA-TCA (Seq. ID No. 24); CAC-AAA-TAA-GAT-TCT-AAG-AAT (Seq. ID No. 25) and TCA-AAA-GAA-TGC-TTC-AAC-AC (Seq. ID No. 26). The set would further comprise at least one non-nucleic acid probe suitable for detecting human chromosome 3, wherein at least one probe of the set has a probing nucleobase sequence, at least a portion of which is at least ninety percent homologous to the nucleobase sequences, or there complements, which are selected from the group consisting of: ATA-ATT-AGA-CCG-GAA-TCA-T (Seq. ID No. 27); GCT-GTT-TTC-TAA-AGG-AAA-G (Seq. ID No. 28); AAG-ACT-TCA-AAG-AGG-TCC (Seq. ID No. 29); TTT-GTC-AAG-AAT-TAT-AAG-AAG (Seq. ID No. 30); CAA-GAT-TGC-TTT-TAA-TGG (Seq. ID No. 31); TGT-GTA-TCA-ACT-CAC-GGA (Seq. ID No. 32); CCT-CAC-AAA-GTA-GAA-ACT (Seq. ID No. 33); GAA-AAA-GCA-GTT-ACT-GAG (Seq. ID No. 34); TAA-TAA-TTA-GAC-GGA-ATC-AT (Seq. ID No. 35); TTA-CAG-GGC-ATT-GAA-GCC (Seq. ID No. 36); CAG-TTA-TGA-AGC-AGT-CTC (Seq. ID No. 37); CAC-ACC-AGA-AAA-AGC-AGT (Seq. ID No. 38); AAG-GGT-AAA-CAC-TGT-GAG (Seq. ID No. 39); AGA-CAA-CGA-AAT-ATC-TTC-ATG (Seq. ID No. 40); CTA-GCA-GTA-TGA-GGT-CAA (Seq. ID No. 41); GCA-GAC-TTC-AGA-AAC-AGA (Seq. ID No. 42); GGC-CTC-AAA-GAC-GTT-TAA (Seq. ID No. 43); GTG-AAA-GTT-CCA-AGT-GAA (Seq. ID No. 44); GAG-TGC-TTT-GAA-GCC-TAC (Seq. ID No. 45); GAA-ACA-GCA-GAG-TTG-AAA (Seq. ID No. 46); TGC-AGA-GAT-CAC-AAC-GTG (Seq. ID No. 47); ACA-AAG-AAT-CAT-TCG-CAG (Seq. ID No. 48) and AGT-GTT-AGA-AAA-CTG-CTC (Seq. ID No. 49). The set would further comprise at least one non-nucleic acid probe suitable for detecting human chromosome 4, wherein at least one probe of the set has a probing nucleobase sequence, at least a portion of which is at least ninety percent homologous to the nucleobase sequences, or there complements, which are selected from the group consisting of: ACA-CGA-TTT-TGG-AAA-CAC (Seq. ID No. 119); CGA-AAC-ATC-ACT-GAG-AGT (Seq. ID No. 120); GGA-TGA-CAT-ATA-ATA-ACT-AG (Seq. ID No. 121); GAA-TTG-AAC-ATT-CAC-TTT-GA (Seq. ID No. 122); TAG-CTC-TGA-AGA-TTT-CGT (Seq. ID No. 123); GAG-ATG-TTT-CCG-AGA-ATG (Seq. ID No. 124); GTG-TAT-TCA-ACT-ACC-AGA (Seq. ID No. 125); ACA-TTT-CTG-TTA-CAG-AGC (Seq. ID No. 126); ATG-ACG-TAT-AAA-ATC-TAG-AG (Seq. ID No. 127); ACG-AAC-ACA-GTT-GAA-CCT (Seq. ID No. 128); and CTC-ATA-AAA-ACC-AGA-AAG-AG (Seq. ID No. 129). The set would further comprise at least one non-nucleic acid probe suitable for detecting human chromosome 6, wherein at least one probe of the set has a probing nucleobase sequence, at least a portion of which is at least ninety percent homologous to the nucleobase sequences, or there complements, which are selected from the group consisting of: CTG-TTC-AGA-GTA-ACA-TGA (Seq. ID No. 50); CCG-CTT-GGA-AAT-ACT-ACA (Seq. ID No. 51); GAA-ATG-GAA-ATA-TCT-CCC-C (Seq. ID No. 52); TCT-AGG-AGG-TCC-AAT-TAT (Seq. ID No. 53); GAA-TTC-CCA-AGT-GGA-TAT (Seq. ID No. 54); CTG-TAG-GTT-TAG-ATG-AAG (Seq. ID No. 55); AAG-GAG-TGT-TTC-CCA-ACT (Seq. ID No. 56); GGC-TTC-AAG-GCG-CTC-TAA (Seq. ID No. 57); GCA-GAG-ACT-TCA-AAG-TGC (Seq. ID No. 58); CAC-ACA-CAC-GGT-GGA-CCA (Seq. ID No. 59); CAA-AGG-GAA-TGT-TCC-ATT (Seq. ID No. 60); CAC-ATA-GCA-GTG-TTT-GAG (Seq. ID No. 61); CTC-AAG-GCG-GTC-CAA-TTA (Seq. ID No. 62); GAG-TCG-AAA-TGC-ACA-CAT (Seq. ID No. 63) and TAC-CAA-GAG-GAA-TGT-TGC (Seq. ID No. 64). The set would further comprise at least one non-nucleic acid probe suitable for detecting human chromosome 7, wherein at least one probe of the set has a probing nucleobase sequence, at least a portion of which is at least ninety percent homologous to the nucleobase sequences, or there complements, which are selected from the group consisting of: CAG-TTC-ATA-TGT-GCA-GTG (Seq. ID No. 130); GGA-ATA-TCG-TCA-CCT-AAA (Seq. ID No. 131); TGG-AGC-AAA-TTG-AAG-CCT (Seq. ID No. 132); TGG-AGC-ACA-TTT-ATG-CCT (Seq. ID No. 133); TGC-ATT-CTA-CTC-CCA-TAG (Seq. ID No. 134); ACA-CTC-TGT-TTC-TAA-AAT-CT (Seq. ID No. 135); GCA-GGC-GGA-TAT-TTA-GTA (Seq. ID No. 136); AGC-GAT-TTG-ATG-CCA-ACA (Seq. ID No. 137); TTG-CAA-ACG-GGG-TTT-CTT (Seq. ID No. 138); CTT-TCA-TGC-TAG-ACA-GAA (Seq. ID No. 139); CAA-AAA-AGT-TAC-TGA-GAA-C (Seq. ID No. 140); AAA-U ATG-CCA-CAG-CAA-GAG (Seq. ID No. 141); GTT-TGA-AAA-CAC-ACT-GTT-TG (Seq. ID No. 142); ATA-TGG-ACC-TGT-TTG-AGG (Seq. ID No. 143) and CAT-TGA-ATG-CTA-GAC-GGA (Seq. ID No. 144). The set would further comprise at least one non-nucleic acid probe suitable for detecting human chromosome 8, wherein at least one probe of the set has a probing nucleobase sequence, at least a portion of which is at least ninety percent homologous to the nucleobase sequences, or there complements, which are selected from the group consisting of: ACG-GGA-TGC-AAT-ATA-AAA (Seq. ID No. 65); TGA-AGA-TTC-TGC-ATA-CGG (Seq. ID No. 66); AAG-GTT-TGT-ACT-GAC-AGA (Seq. ID No. 67); CTG-AAC-TAT-GGT-GAA-AAA (Seq. ID No. 68); ACT-AAC-TGT-GCT-GAA-CAT (Seq. ID No. 69) and CCC-ATG-AAT-GCG-AGA-TAG (Seq. ID No. 70). The set would further comprise at least one non-nucleic acid probe suitable for detecting human chromosome 9, wherein at least one probe of the set has a probing nucleobase sequence, at least a portion of which is at least ninety percent homologous to the nucleobase sequences, or there complements, which are selected from the group consisting of: ATG-ATG-AAA-AAG-GTA-ATA-E (Seq. ID No. 145) and CAT-TCT-CAG-AAC-TGT-TTG-E (Seq. ID No. 146). The set would further comprise at least one non-nucleic acid probe suitable for detecting human chromosome 10, wherein at least one probe of the set has a probing nucleobase sequence, at least a portion of which is at least ninety percent homologous to the nucleobase sequences, or there complements, which are selected from the group consisting of: AAC-TGA-ACG-CAC-AGA-TGA (Seq. ID No. 71); GGC-TAA-TCT-TTG-AAA-TTG-AAA (Seq. ID No. 72); AGG-TGG-ATA-ATT-GGC-CCT (Seq. ID No. 73); TGA-AGT-CCA-AAA-AAG-CAC (Seq. ID No. 74); CTT-AGA-CAT-GGA-AAT-ATC (Seq. ID No. 75); AAG-GGG-TCT-AAC-TAA-TCA (Seq. ID No. 76) and GTA-GTT-GTT-GAG-AAT-GAT (Seq. ID No. 77). The set would further comprise at least one non-nucleic acid probe suitable for detecting human chromosome 11, wherein at least one probe of the set has a probing nucleobase sequence, at least a portion of which is at least ninety percent homologous to the nucleobase sequences, or there complements, which are selected from the group consisting of: AAC-TTC-CCA-GAA-CTA-CAC (Seq. ID No. 78); ATT-CTT-GAA-ATG-GAA-CAC (Seq. ID No. 79); CTG-TGA-TTG-CTG-ATT-TGG (Seq. ID No. 80); GTC-ATC-ACA-GGA-AAC-ATT (Seq. ID No. 81); GAA-ATT-TCC-TGT-TGA-CAG-A (Seq. ID No. 82) and GTT-TGA-AAG-CTG-AAC-TAT-G (Seq. ID No. 83). The set would further comprise at least one non-nucleic acid probe suitable for detecting human chromosome 12, wherein at least one probe of the set has a probing nucleobase sequence, at least a portion of which is at least ninety percent homologous to the nucleobase sequences, or there complements, which are selected from the group consisting of: TCC-TGT-AAT-GTT-CGA-CAG (Seq. ID No. 84); TCA-TAG-AAC-GCT-AGA-AAG (Seq. ID No. 85); ACC-TTT-CTT-TTG-ATG-AAG-GA (Seq. ID No. 86); CAA-ATA-TCA-CAA-AAA-GAG-GG (Seq. ID No. 87); GAG-TTG-AAT-AGA-GGC-AAC (Seq. ID No. 88); GGC-CAA-ATG-TAG-AAA-AGG (Seq. ID No. 89); GCG-TTC-AAC-TCA-AGG-TGT (Seq. ID No. 90); TGT-CCT-TTA-GAC-AGA-GCA (Seq. ID No. 91); TGA-GAC-CAA-ATG-TAC-AAA-AG (Seq. ID No. 92); GAA-TAC-TGA-GTA-AGT-TCT-TTG (Seq. ID No. 93); AAC-TGC-ACA-AAT-AGG-GTG (Seq. ID No. 94); TGG-AGA-CAC-TGT-GTT-TGT (Seq. ID No. 95) and CCA-GTT-GGA-GAT-TTC-AAT (Seq. ID No. 96). The set would further comprise at least one non-nucleic acid probe suitable for detecting human chromosome 16, wherein at least one probe of the set has a probing nucleobase sequence, at least a portion of which is at least ninety percent homologous to the nucleobase sequences, or there complements, which are selected from the group consisting of: GAA-GCC-TGC-CAG-TGG-ATA (Seq. ID No. 97); TAC-AGC-ATT-CTG-GAA-ACC (Seq. ID No. 98); CCA-GAC-ACT-GCG-TAG-TGA (Seq. ID No. 99); ATA-TAA-TGC-TAG-AGG-GAG (Seq. ID No. 100) and AAA-AAC-AAG-ACA-AAC-TCG (Seq. ID No. 101). The set would further comprise at least one non-nucleic acid probe suitable for detecting human chromosome 17, wherein at least one probe of the set has a probing nucleobase sequence, at least a portion of which is at least ninety percent homologous to the nucleobase sequences, or there complements, which are selected from the group consisting of: ATT-TCA-GCT-GAC-TAA-ACA (Seq. ID No. 102); AAC-GAA-TTA-TGG-TCA-CAT (Seq. ID No. 103); GGT-GAC-GAC-TGA-GTT-TAA (Seq. ID No. 104); TTT-GGA-CCA-CTC-TGT-GGC (Seq. ID No. 105); AAC-GGG-ATA-ACT-GCA-CCT (Seq. ID No. 106); TTT-GTG-GTT-TGT-GGT-GGA (Seq. ID No. 107); AGG-GAA-TAG-CTT-CAT-AGA (Seq. ID No. 108); ATC-ACG-AAG-AAG-GTT-CTG (Seq. ID No. 109); CCG-AAG-ATG-TCT-TTG-GAA (Seq. ID No. 110) and AAA-GAG-GTC-TAC-ATG-TCC (Seq. ID No. 111). The set would further comprise at least one non-nucleic acid probe suitable for detecting human chromosome 18, wherein at least one probe of the set has a probing nucleobase sequence, at least a portion of which is at least ninety percent homologous to the nucleobase sequences, or there complements, which are selected from the group consisting of: TTC-CCG-TAA-CAA-CTA-TGC (Seq. ID No. 112); TCC-CGT-AAC-AAC-TAG-GCA (Seq. ID No. 113); AAA-AGG-AGT-GAT-CCA-ACC (Seq. ID No. 114); TCC-CTT-TGG-TAG-AGC-AGG (Seq. ID No. 115); ATT-TGA-GAT-GTG-TGT-ACT-CA (Seq. ID No. 116); GCA-CTT-ACC-GGC-CTA-AG (Seq. ID No. 117) and CTC-AGA-AAC-TTA-CTC-GTG (Seq. ID No. 118). The set would further comprise at least one non-nucleic acid probe suitable for detecting human chromosome 20, wherein at least one probe of the set has a probing nucleobase sequence, at least a portion of which is at least ninety percent homologous to the nucleobase sequences, or there complements, which are selected from the group consisting of: ACA-GAA-CTA-AAC-CAT-CGT (Seq. ID No. 147); TAG-GCC-AGC-TTG-GAG-GAT (Seq. ID No. 148); CTA-GCT-GGG-AGG-ATT-T (Seq. ID No. 149); TGT-GCC-TCA-ACT-GAC-A-E (Seq. ID No. 150); TGC-TTT-GGG-ATG-TTT-CAA (Seq. ID No. 151) and GCA-ATG-TCA-GAA-CTT-TTT-TC (Seq. ID No. 152). The set would further comprise at least one non-nucleic acid probe suitable for detecting human chromosome 13/21, wherein at least one probe of the set has a probing nucleobase sequence, at least a portion of which is at least ninety percent homologous to the nucleobase sequences, or there complements, which are selected from the group consisting of: CCG-AAA-GAA-ATT-TGT-GGG (Seq. ID No. 153); GAA-CAT-GGC-CTT-TCA-TAG (Seq. ID No. 154); TCA-AGG-CGA-TCG-AAA-TGT (Seq. ID No. 155); GAG-ACA-CAT-ATC-ACC-AAC (Seq. ID No. 156); CAG-AAA-TTT-CTT-TCG-GAT-A (Seq. ID No. 157); GAA-CAT-GGC-CTT-TCA-TAG (Seq. ID No. 158) and AGC-CAA-AGG-AGT-TGA-ACA (Seq. ID No. 159).

In a preferred embodiment, probes of the set that are specific for detecting each particular chromosome would be independently detectable from probes for detecting the other chromosomes. This would enable the independent detection, identification and quantitation of each of chromosomes X, Y, 1, 2, 3, 4, 6, 7, 8, 9, 10, 11, 12, 16, 17, 18 and/or 20, as well as 13/21 as a pair, in the same sample and in the same assay. Most preferably, the probes of the set will be labeled with one or more independently detectable fluorophores to thereby enable correlation of a particular fluorophore, or set of fluorophores, with the presence of a particular human chromosome.

A second exemplary probe set might comprise those non-nucleic acid probes suitable for the detection of human chromosome X. A suitable exemplary probe set might therefore comprise at least two non-nucleic acid probes suitable for detecting the human chromosome X, wherein at least one probe of the set has a probing nucleobase sequence, at least a portion of which is at least ninety percent homologous to the nucleobase sequences, or there complements, which are selected from the group consisting of: CTT-CAA-AGA-GGT-CCA-CGA (Seq. ID No. 1); AGG-GTT-CAA-CTG-TGT-GAC (Seq. ID No. 2); GAA-ACT-TCT-GAG-TGA-TGA (Seq. ID No. 3); CAG-TCA-TCG-CAG-AAA-ACT (Seq. ID No. 4); AGA-TTT-CAC-TGG-AAA-CGG (Seq. ID No. 5); GTT-ATG-GGA-AGG-TGA-TCC (Seq. ID No. 6); TCG-AGC-CGC-AGA-GTT-TAA (Seq. ID No. 7); CTA-TTT-AGC-GGG-CTT-GGA (Seq. ID No. 8) and TAC-AAG-GGT-GTT-GCA-AAC (Seq. ID No. 9).

A third exemplary probe might comprise those non-nucleic acid probes suitable for the detection of human chromosome Y. A suitable exemplary probe set might therefore comprise at least two non-nucleic acid probes suitable for detecting the human Y chromosome, wherein at least one probe of the set has a probing nucleobase sequence, at least a portion of which is at least ninety percent homologous to the nucleobase sequences, or there complements, which are selected from the group consisting of: CCA-TAT-GCA-GTT-ATA-AGT-AGG (Seq. ID No. 10); TAT-TGT-ACC-AAG-CAG-AGT-ACC (Seq. ID No. 11); GGT-ATA-TAT-AAG-ATG-ACA-CAG-GA (Seq. ID No. 12); GTT-AGT-TAT-ATT-GGG-TGA-TAT-GT (Seq. ID No. 13); TCA-CAT-AAT-AGA-CAA-CAT-AC (Seq. ID No. 14); CAG-AAG-AGA-TTG-AAC-CTT (Seq. ID No. 15) and GGC-ATA-GCA-CAT-AAC-ATG (Seq. ID No. 16).

A fourth exemplary probe set might comprise those non-nucleic acid probes suitable for the detection of human chromosome 1. A suitable exemplary, probe set might therefore comprise at least two non-nucleic acid probes suitable for detecting the human chromosome 1, wherein at least one probe of the set has a probing nucleobase sequence, at least a portion of which is at least ninety percent homologous to the nucleobase sequences, or there complements, which are selected from the group consisting of: AAT-CGT-CAT-CGA-ATG-AAT (Seq. ID No. 17) and CAT-TGA-ACA-GAA-TTG-AAT (Seq. ID No. 18).

A fifth exemplary probe set might comprise those probes suitable for the detection of human chromosome 2. A suitable exemplary probe set might therefore comprise at least two non-nucleic acid probes suitable for detecting the human chromosome 2, wherein at least one probe of the set has a probing nucleobase sequence, at least a portion of which is at least ninety percent homologous to the nucleobase sequences, or there complements, which are selected from the group consisting of: GTT-TTC-AGG-GGA-AGA-TAT (Seq. ID No. 19); TGT-GCG-CCC-TCA-ACT-AAC (Seq. ID No. 20); GAA-GCT-TCA-TTG-GGA-TGT (Seq. ID No. 21); CCA-ATA-AAA-GCT-ACA-TAG-A (Seq. ID No. 22); GAA-AAA-GTT-TCT-GAC-ATT-GC (Seq. ID No. 23); TAG-TTG-AAG-GGC-ACA-TCA (Seq. ID No. 24); CAC-AAA-TAA-GAT-TCT-AAG-AAT (Seq. ID No. 25) and TCA-AAA-GAA-TGC-TTC-AAC-AC (Seq. ID No. 26).

A sixth exemplary probe set might comprise those probes suitable for the detection of human chromosome 3. A suitable exemplary probe set might therefore comprise at least two non-nucleic acid probes suitable for detecting the human chromosome 3, wherein at least one probe of the set has a probing nucleobase sequence, at least a portion of which is at least ninety percent homologous to the nucleobase sequences, or there complements, which are selected from the group consisting of: ATA-ATT-AGA-CCG-GAA-TCA-T (Seq. ID No. 27); GCT-GTT-TTC-TAA-AGG-AAA-G (Seq. ID No. 28); AAG-ACT-TCA-AAG-AGG-TCC (Seq. ID No. 29); TTT-GTC-AAG-AAT-TAT-AAG-AAG (Seq. ID No. 30); CAA-GAT-TGC-TTT-TAA-TGG (Seq. ID No. 31); TGT-GTA-TCA-ACT-CAC-GGA (Seq. ID No. 32); CCT-CAC-AAA-GTA-GAA-ACT (Seq. ID No. 33); GAA-AAA-GCA-GTT-ACT-GAG (Seq. ID No. 34); TAA-TAA-TTA-GAC-GGA-ATC-AT (Seq. ID No. 35); TTA-CAG-GGC-ATT-GAA-GCC (Seq. ID No. 36); CAG-TTA-TGA-AGC-AGT-CTC (Seq. ID No. 37); CAC-ACC-AGA-AAA-AGC-AGT (Seq. ID No. 38); AAG-GGT-AAA-CAC-TGT-GAG (Seq. ID No. 39); AGA-CAA-CGA-AAT-ATC-TTC-ATG (Seq. ID No. 40); CTA-GCA-GTA-TGA-GGT-CAA (Seq. ID No. 41); GCA-GAC-TTC-AGA-AAC-AGA (Seq. ID No. 42); GGC-CTC-AAA-GAC-GTT-TAA (Seq. ID No. 43); GTG-AAA-GTT-CCA-AGT-GAA (Seq. ID No. 44); GAG-TGC-TTT-GAA-GCC-TAC (Seq. ID No. 45); GAA-ACA-GCA-GAG-TTG-AAA (Seq. ID No. 46); TGC-AGA-GAT-CAC-AAC-GTG (Seq. ID No. 47); ACA-AAG-AAT-CAT-TCG-CAG (Seq. ID No. 48) and AGT-GTT-AGA-AAA-CTG-CTC (Seq. ID No. 49).

A seventh exemplary probe set might comprise those probes suitable for the detection of human chromosome 4. A suitable exemplary probe set might therefore comprise at least two non-nucleic acid probes suitable for detecting the human chromosome 4, wherein at least one probe of the set has a probing nucleobase sequence, at least a portion of which is at least ninety percent homologous to the nucleobase sequences, or there complements, which are selected from the group consisting of: ACA-CGA-TTT-TGG-AAA-CAC (Seq. ID No. 119); CGA-AAC-ATC-ACT-GAG-AGT (Seq. ID No. 120); GGA-TGA-CAT-ATA-ATA-ACT-AG (Seq. ID No. 121); GAA-TTG-AAC-ATT-CAC-TTT-GA (Seq. ID No. 122); TAG-CTC-TGA-AGA-TTT-CGT (Seq. ID No. 123); GAG-ATG-TTT-CCG-AGA-ATG (Seq. ID No. 124); GTG-TAT-TCA-ACT-ACC-AGA (Seq. ID No. 125); ACA-TTT-CTG-TTA-CAG-AGC (Seq. ID No. 126); ATG-ACG-TAT-AAA-ATC-TAG-AG (Seq. ID No. 127); ACG-AAC-ACA-GTT-GAA-CCT (Seq. ID No. 128); and CTC-ATA-AAA-ACC-AGA-AAG-AG (Seq. ID No. 129).

An eighth exemplary probe might comprise those probes suitable for the detection of human chromosome 6. A suitable exemplary probe set might therefore comprise at least two non-nucleic acid probes suitable for detecting the human chromosome 6, wherein at least one probe of the set has a probing nucleobase sequence, at least a portion of which is at least ninety percent homologous to the nucleobase sequences, or there complements, which are selected from the group consisting of: CTG-TTC-AGA-GTA-ACA-TGA (Seq.

ID No. 50); CCG-CTT-GGA-AAT-ACT-ACA (Seq. ID No. 51); GAA-ATG-GAA-ATA-TCT-CCC-C (Seq. ID No. 52); TCT-AGG-AGG-TCC-AAT-TAT (Seq. ID No. 53); GAA-TTC-CCA-AGT-GGA-TAT (Seq. ID No. 54); CTG-TAG-GTT-TAG-ATG-AAG (Seq. ID No. 55); AAG-GAG-TGT-TTC-CCA-ACT (Seq. ID No. 56); GGC-TTC-AAG-GCG-CTC-TAA (Seq. ID No. 57); GCA-GAG-ACT-TCA-AAG-TGC (Seq. ID No. 58); CAC-ACA-CAC-GGT-GGA-CCA (Seq. ID No. 59); CAA-AGG-GAA-TGT-TCC-ATT (Seq. ID No. 60); CAC-ATA-GCA-GTG-TTT-GAG (Seq. ID No. 61); CTC-AAG-GCG-GTC-CAA-TTA (Seq. ID No. 62); GAG-TCG-AAA-TGC-ACA-CAT (Seq. ID No. 63) and TAC-CAA-GAG-GAA-TGT-TGC (Seq. ID No. 64).

A ninth exemplary probe might comprise those probes suitable for the detection of human chromosome 7. A suitable exemplary probe set might therefore comprise at least two non-nucleic acid probes suitable for detecting the human chromosome 7, wherein at least one probe of the set has a probing nucleobase sequence, at least a portion of which is at least ninety percent homologous to the nucleobase sequences, or there complements, which are selected from the group consisting of: CAG-TIC-ATA-TGT-GCA-GTG (Seq. ID No. 130); GGA-ATA-TCG-TCA-CCT-AAA (Seq. ID No. 131); TGG-AGC-AAA-TTG-AAG-CCT (Seq. ID No. 132); TGG-AGC-ACA-TTT-ATG-CCT (Seq. ID No. 133); TGC-ATT-CTA-CTC-CCA-TAG (Seq. ID No. 134); ACA-CTC-TGT-TTC-TAA-AAT-CT (Seq. ID No. 135); GCA-GGC-GGA-TAT-TTA-GTA (Seq. ID No. 136); AGC-GAT-TTG-ATG-CCA-ACA (Seq. ID No. 137); TTG-CAA-ACG-GGG-Z TTT-CTT (Seq. ID No. 138); CTT-TCA-TGC-TAG-ACA-GAA (Seq. ID No. 139); CAA-AAA-AGT-TAC-TGA-GAA-C (Seq. ID No. 140); AAA-ATG-CCA-CAG-CAA-GAG (Seq. ID No. 141); GTT-TGA-AAA-CAC-ACT-GTT-TG (Seq. ID No. 142); ATA-TGG-ACC-TGT-TTG-AGG (Seq. ID No. 143) and CAT-TGA-ATG-CTA-GAC-GGA (Seq. ID No. 144).

A tenth exemplary probe might comprise those probes suitable for the detection of human chromosome 8. A suitable exemplary probe set might therefore comprise at least two non-nucleic acid probes suitable for detecting the human chromosome 8, wherein at least one probe of the set has a probing nucleobase sequence, at least a portion of which is at least ninety percent homologous to the nucleobase sequences, or there complements, which are selected from the group consisting of: ACG-GGA-TGC-AAT-ATA-AAA (Seq. ID No. 65); TGA-AGA-TTC-TGC-ATA-CGG (Seq. ID No. 66); AAG-GTT-TGT-ACT-GAC-AGA (Seq. ID No. 67); CTG-AAC-TAT-GGT-GAA-AAA (Seq. ID No. 68); ACT-AAC-TGT-GCT-GAA-CAT (Seq. ID No. 69) and CCC-ATG-AAT-GCG-AGA-TAG (Seq. ID No. 70).

An eleventh exemplary probe might comprise those probes suitable for the detection of human chromosome 9. A suitable exemplary probe set might therefore comprise at least two non-nucleic acid probes suitable for detecting the human chromosome 9, wherein at least one probe of the set has a probing nucleobase sequence, at least a portion of which is at least ninety percent homologous to the nucleobase sequences, or there complements, which are selected from the group consisting of: ATG-ATG-AAA-AAG-GTA-ATA-E (Seq. ID No. 145) and CAT-TCT-CAG-AAC-TGT-TTG-E (Seq. ID No. 146).

A twelfth exemplary probe set might comprise those non-nucleic acid probes suitable for the detection of human chromosome 10. A suitable exemplary probe set might therefore comprise at least two non-nucleic acid probes suitable for detecting the human chromosome 10, wherein at least one probe of the set has a probing nucleobase sequence, at least a portion of which is at least ninety percent homologous to the nucleobase sequences, or there complements, which are selected from the group consisting of: AAC-TGA-ACG-CAC-AGA-TGA (Seq. ID No. 71); GGC-TAA-TCT-TTG-AAA-TTG-AAA (Seq. ID No. 72); AGG-TGG-ATA-ATT-GGC-CCT (Seq. ID No. 73); TGA-AGT-CCA-AAA-AAG-CAC (Seq. ID No. 74); CTT-AGA-CAT-GGA-AAT-ATC (Seq. ID No. 75); AAG-GGG-TCT-AAC-TAA-TCA (Seq. ID No. 76) and GTA-GTT-GTT-GAG-AAT-GAT (Seq. ID No. 77).

A thirteenth exemplary probe set might comprise those non-nucleic acid probes suitable for the detection of human chromosome 11. A suitable probe set might therefore comprise at least two non-nucleic acid probes suitable for detecting the human chromosome 11, wherein at least one probe of the set has a probing nucleobase sequence, at least a portion of which is at least ninety percent homologous to the nucleobase sequences, or there complements, which are selected from the group consisting of: AAC-TTC-CCA-GAA-CTA-CAC (Seq. ID No. 78); ATT-CTT-GAA-ATG-GAA-CAC (Seq. ID No. 79); CTG-TGA-TTG-CTG-ATT-TGG (Seq. ID No. 80); GTC-ATC-ACA-GGA-AAC-ATT (Seq. ID No. 81); GAA-ATT-TCC-TGT-TGA-CAG-A (Seq. ID No. 82) and GTT-TGA-AAG-CTG-AAC-TAT-G (Seq. ID No. 83).

A fourteenth exemplary probe set might comprise those non-nucleic acid probes suitable for the detection of human chromosome 12. A suitable exemplary probe set might therefore comprise at least two non-nucleic acid probes suitable for detecting the human chromosome 12, wherein at least one probe of the set has a probing nucleobase sequence, at least a portion of which is at least ninety percent homologous to the nucleobase sequences, or there complements, which are selected from the group consisting of: TCC-TGT-AAT-GTT-CGA-CAG (Seq. ID No. 84); TCA-TAG-AAC-GCT-AGA-AAG (Seq. ID No. 85); ACC-TTT-CTT-TTG-ATG-AAG-GA (Seq. ID No. 86); CAA-ATA-TCA-CAA-AAA-GAG-GG (Seq. ID No. 87); GAG-TTG-AAT-AGA-GGC-AAC (Seq. ID No. 88); GGC-CAA-ATG-TAG-AAA-AGG (Seq. ID No. 89); GCG-TTC-AAC-TCA-AGG-TGT (Seq. ID No. 90); TGT-CCT-TTA-GAC-AGA-GCA (Seq. ID No. 91); TGA-GAC-CAA-ATG-TAC-AAA-AG (Seq. ID No. 92); GAA-TAC-TGA-GTA-AGT-TCT-TTG (Seq. ID No. 93); AAC-TGC-ACA-AAT-AGG-GTG (Seq. ID No. 94); TGG-AGA-CAC-TGT-GTT-TGT (Seq. ID No. 95) and CCA-GTT-GGA-GAT-TTC-AAT (Seq. ID No. 96).

A fifteenth exemplary probe set might comprise those probes suitable for the detection of human chromosome 16. A suitable exemplary probe set might therefore comprise at least two non-nucleic acid probes suitable for detecting the human chromosome 16, wherein at least one probe of the set has a probing nucleobase sequence, at least a portion of which is at least ninety percent homologous to the nucleobase sequences, or there complements, which are selected from the group consisting of: GAA-GCC-TGC-CAG-TGG-ATA (Seq. ID No. 97); TAC-AGC-ATT-CTG-GAA-ACC (Seq. ID No. 98); CCA-GAC-ACT-GCG-TAG-TGA (Seq. ID No. 99); ATA-TAA-TGC-TAG-AGG-GAG (Seq. ID No. 100) and AAA-AAC-AAG-ACA-AAC-TCG (Seq. ID No. 101).

A sixteenth exemplary probe might comprise those probes suitable for the detection of human chromosome 17. A suitable exemplary probe set might therefore comprise at least two non-nucleic acid probes suitable for detecting the human chromosome 17, wherein at least one probe of the set has a probing nucleobase sequence, at least a portion of which is at least ninety percent homologous to the nucleobase sequences, or there complements, which are selected from the group consisting of: ATT-TCA-GCT-GAC-TAA-ACA (Seq.

ID No. 102); AAC-GAA-TTA-TGG-TCA-CAT (Seq. ID No. 103); GGT-GAC-GAC-TGA-GTT-TAA (Seq. ID No. 104); TTT-GGA-CCA-CTC-TGT-GGC (Seq. ID No. 105); AAC-GGG-ATA-ACT-GCA-CCT (Seq. ID No. 106); TTT-GTG-GTT-TGT-GGT-GGA (Seq. ID No. 107); AGG-GAA-TAG-CTT-CAT-AGA (Seq. ID No. 108); ATC-ACG-AAG-AAG-GTT-CTG (Seq. ID No. 109); CCG-AAG-ATG-TCT-TTG-GAA (Seq. ID No. 110) and AAA-GAG-GTC-TAC-ATG-TCC (Seq. ID No. 111).

A seventeenth exemplary probe set might comprise those non-nucleic acid probes suitable for the detection of human chromosome 18. A suitable exemplary probe set might therefore comprise at least two non-nucleic acid probes suitable for detecting the human chromosome 18, wherein at least one probe of the set has a probing nucleobase sequence, at least a portion of which is at least ninety percent homologous to the nucleobase sequences, or there complements, which are selected from the group consisting of: TTC-CCG-TAA-CAA-CTA-TGC (Seq. ID No. 112); TCC-CGT-AAC-AAC-TAG-GCA (Seq. ID No. 113); AAA-AGG-AGT-GAT-CCA-ACC (Seq. ID No. 114); TCC-CTT-TGG-TAG-AGC-AGG (Seq. ID No. 115); ATT-TGA-GAT-GTG-TGT-ACT-CA (Seq. ID No. 116); GCA-CTT-ACC-GGC-CTA-AG (Seq. ID No. 117) and CTC-AGA-AAC-TTA-CTC-GTG (Seq. ID No. 118).

An eighteenth exemplary probe set might comprise those non-nucleic acid probes suitable for the detection of human chromosome 20. A suitable exemplary probe set might therefore comprise at least two non-nucleic acid probes suitable for detecting the human chromosome 18, wherein at least one probe of the set has a probing nucleobase sequence, at least a portion of which is at least ninety percent homologous to the nucleobase sequences, or there complements, which are selected from the group consisting of: ACA-GAA-CTA-AAC-CAT-CGT (Seq. ID No. 147); TAG-GCC-AGC-TTG-GAG-GAT (Seq. ID No. 148); CTA-GCT-GGG-AGG-ATT-T (Seq. ID No. 149); TGT-GCC-TCA-ACT-GAC-A-E (Seq. ID No. 150); TGC-TTT-GGG-ATG-TTT-CAA (Seq. ID No. 151) and GCA-ATG-TCA-GAA-CTT-TTT-TC (Seq. ID No. 152).

Still a nineteenth exemplary probe set might comprise those non-nucleic acid probes suitable for the detection of human chromosome 13/21. A suitable exemplary probe set might therefore comprise at least two non-nucleic acid probes suitable for detecting the human chromosome 18, wherein at least one probe of the set has a probing nucleobase sequence, at least a portion of which is at least ninety percent homologous to the nucleobase sequences, or there complements, which are selected from the group consisting of: CCG-AAA-GAA-ATT-TGT-GGG (Seq. ID No. 153); GAA-CAT-GGC-CTT-TCA-TAG (Seq. ID No. 154); TCA-AGG-CGA-TCG-AAA-TGT (Seq. ID No. 155); GAG-ACA-CAT-ATC-ACC-AAC (Seq. ID No. 156); CAG-AAA-TTT-CTT-TCG-GAT-A (Seq. ID No. 157); GAA-CAT-GGC-CTT-TCA-TAG (Seq. ID No. 158) and AGC-CAA-AGG-AGT-TGA-ACA (Seq. ID No. 159).

Figure 21:
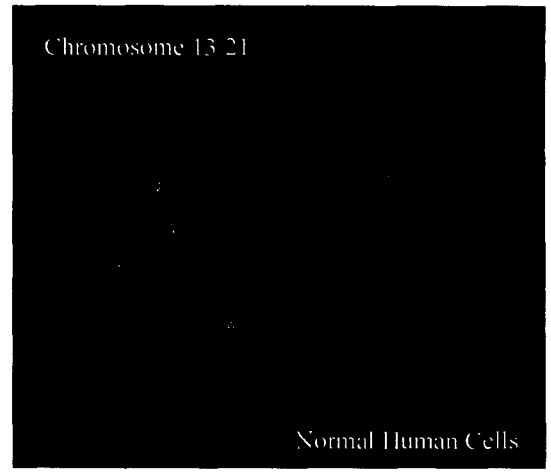
In FIG. 21, signals for human chromosome 13/21 as a pair are clearly detectable in the visible interphase nuclei and metaphase spreads. Since the detection of both chromosomes 13 and 21 is simultaneous, a total of four spots is visible in each normal chromosome or metaphase spread.

In yet another embodiment, this invention is directed to probe sets that can be used with the methods described herein or otherwise packaged into kits and which are suitable for the simultaneous and specific detection of two or more chromosomes such that at least two the individual probes of the probe set or kit, that is used in the method, hybridize to all of the two or more specific chromosomes sought to be detected. Preferably the probe sets, methods and kits pertain to the simultaneous and specific detection of chromosomes 13 and 21 (See: FIG. 21) or chromosomes 14 and 22, as a pair. Suitable non-nucleic acid probes that are specific for the detection of human chromosomes 13 and 21 have been previously described herein. One suitable exemplary probe set might therefore comprise least one probe having a probing nucleobase sequence, at least a portion of which is at least ninety percent homologous to the nucleobase sequences, or there complements, which are selected from the group consisting of: CCG-AAA-GAA-ATT-TGT-GGG (Seq. ID No. 153); GAA-CAT-GGC-CTT-TCA-TAG (Seq. ID No. 154); TCA-AGG-CGA-TCG-AAA-TGT (Seq. ID No. 155); GAG-ACA-CAT-ATC-ACC-AAC (Seq. ID No. 156); CAG-AAA-TTT-CTT-TCG-GAT-A (Seq. ID No. 157); GAA-CAT-GGC-CTT-TCA-TAG (Seq. ID No. 158) and AGC-CAA-AGG-AGT-TGA-ACA (Seq. ID No. 159).

In still another embodiment, this invention is directed to a probe set that can be used with the methods described herein or otherwise packaged into kits and which are suitable for prenatal analysis. Preferably, the probes sets, methods and kits for prenatal analysis are specific for the detection, identification and enumeration of human chromosomes X, Y, 18 and 13/21 as a pair. Suitable non-nucleic acid probes that are specific for the detection of these human chromosomes have been previously described herein. Most preferably the prenatal analysis is a multiplex analysis wherein chromosomes X, Y and 18 are detected as individual chromosomes using a unique label and chromosomes 13 & 21 are detected as a pair using yet another unique label. In this manner, conditions of aneuploidy and polyploidy for these individual chromosomes of prenatal significance can be rapidly detected using the standard PNA-ISH and PNA-FISH methods described herein.

Multiplex Probe Sets for PNA-FISH Assays:

Because the individual non-nucleic acid probes of this invention can each be labeled with one or more independently detectable moieties, it is possible to design probe sets wherein each non-nucleic acid probe of the set are independently detectable. Fluorophores that have sufficiently different excitation and emission spectra are often used as independently detectable moieties. A non-limiting example of exemplary independently detectable fluorophores can be found in the section of this specification entitled "Labels". Thus, an assay utilizing a probe set comprising two or more non-nucleic acid probes, each labeled with one or more independently detectable moieties, could be used to independently detect, identify or quantitate the number of the human chromosome X, Y, 1, 2, 3, 4, 6, 7, 8, 9, 10, 11, 12, 16, 17, 18 or 20, as well as 13/21 as a pair, in the same assay. Consequently, the non-nucleic acid probes, probe sets, methods and kits of this invention are particularly useful for the rapid, sensitive, reliable and versatile multiplex analysis of the identified human chromosomes in a single sample and same assay. By versatile we mean that the method is generally applicable despite substantial variability in the length and nucleobase content of the probes used in the assay. In most preferred embodiments, the set of non-nucleic acid probes are suitable for the detection, identification and/or quantitation of all human chromosomes in the same sample and in the same assay (e.g. a multiplex assay).

c. Methods

In another embodiment, this invention is directed to a method suitable for detecting, identifying and/or quantitating human chromosomes X, Y, 1, 2, 3, 4, 6, 7, 8, 9, 10, 11, 12, 16, 17, 18 and/or 20, as well as 13/21 as a pair, in a sample or in the individual cells of a sample. The general and preferred characteristics of non-nucleic acid probes and probe sets suitable for the detection, identification and/or quantitation of the identified human chromosomes have been previously described herein. Preferred probing nucleobase sequences are listed in Table 1. Preferably, the method is used for the simultaneous detection of all human chromosomes in the same assay and most preferably the assay is an automated multiplex PNA-ISH or PNA-FISH assay. Most preferably, the assay is automated and performed using either a slide scanner based analysis system, microscope and camera (e.g. CCD camera) or a flow cytometer.

According to the method, the sample is contacted with one or more non-nucleic acid probes having a probing nucleobase sequence that is specific for one or more of human chromosomes selected from the group consisting of X, Y, 1, 2, 3, 4, 6, 7, 8, 9, 10, 11, 12, 16, 17, 18 or 20, as well as 13/21 as a pair. The one or more chromosomes are then detected, identified and/or quantitated. Detection, identification and/or quantitation (enumeration) is made possible by monitoring the hybridization under suitable hybridization conditions or suitable in-situ hybridization conditions, of the probing nucleobase sequence of non-nucleic acid probes to the target sequences of the chromosomes, and correlating the result with the presence, absence or number of the chromosomes sought to be detected in the sample. Typically, this correlation is made possible by direct or indirect detection of the probe/target sequence hybrid. This method is particularly advantageous for scoring the number of human chromosomes per cell. The number of chromosomes per cell is particularly useful in karyotype analysis.

In preferred embodiments, the method for detecting, identifying or quantitating human chromosomes X, Y, 1, 2, 3, 4, 6, 7, 8, 9, 10, 11, 12, 16, 17, 18 and/or 20, as well as 13/21 as a pair, in a sample comprise contacting the sample with one or more non-nucleic acid probes, wherein at least one probe of the set has a probing nucleobase sequence, at least a portion of which is at least ninety percent homologous to the probing nucleobase sequences, or there complements, which are selected from the group consisting of: CTT-CAA-AGA-GGT-CCA-CGA (Seq. ID No. 1); AGG-GTT-CAA-CTG-TGT-GAC (Seq. ID No. 2); GAA-ACT-TCT-GAG-TGA-TGA (Seq. ID No. 3); CAG-TCA-TCG-CAG-AAA-ACT (Seq. ID No. 4); AGA-TTT-CAC-TGG-AAA-CGG (Seq. ID No. 5); GTT-ATG-GGA-AGG-TGA-TCC (Seq. ID No. 6); TCG-AGC-CGC-AGA-GTT-TAA (Seq. ID No. 7); CTA-TTT-AGC-GGG-CTT-GGA (Seq. ID No. 8); TAC-AAG-GGT-GTT-GCA-AAC (Seq. ID No. 9); CCA-TAT-GCA-GTT-ATA-AGT-AGG (Seq. ID No. 10); TAT-TGT-ACC-AAG-CAG-AGT-ACC (Seq. ID No. 11); GGT-ATA-TAT-AAG-ATG-ACA-CAG-GA (Seq. ID No. 12); GTT-AGT-TAT-ATT-GGG-TGA-TAT-GT (Seq. ID No. 13); TCA-CAT-AAT-AGA-CAA-CAT-AC (Seq. ID No. 14); CAG-AAG-AGA-TTG-AAC-CTT (Seq. ID No. 15); GGC-ATA-GCA-CAT-AAC-ATG (Seq. ID No. 16); AAT-CGT-CAT-CGA-ATG-AAT (Seq. ID No. 17); CAT-TGA-ACA-GAA-TTG-AAT (Seq. ID No. 18); GTT-TTC-AGG-GGA-AGA-TAT (Seq. ID No. 19); TGT-GCG-CCC-TCA-ACT-AAC (Seq. ID No. 20); GAA-GCT-TCA-TTG-GGA-TGT (Seq. ID No. 21); CCA-ATA-AAA-GCT-ACA-TAG-A (Seq. ID No. 22); GAA-AAA-GTT-TCT-GAC-ATT-GC (Seq. ID No. 23); TAG-TTG-AAG-GGC-ACA-TCA (Seq. ID No. 24); CAC-AAA-TAA-GAT-TCT-AAG-AAT (Seq. ID No. 25); TCA-AAA-GAA-TGC-TTC-AAC-AC (Seq. ID No. 26); ATA-ATT-AGA-CCG-GAA-TCA-T (Seq. ID No. 27); GCT-GTT-TTC-TAA-AGG-AAA-G (Seq. ID No. 28); AAG-ACT-TCA-AAG-AGG-TCC (Seq. ID No. 29); TTT-GTC-AAG-AAT-TAT-AAG-AAG (Seq. ID No. 30); CAA-GAT-TGC-TTT-TAA-TGG (Seq. ID No. 31); TGT-GTA-TCA-ACT-CAC-GGA (Seq. ID No. 32); CCT-CAC-AAA-GTA-GAA-ACT (Seq. ID No. 33); GAA-AAA-GCA-GTT-ACT-GAG (Seq. ID No. 34); TAA-TAA-TTA-GAC-GGA-ATC-AT (Seq. ID No. 35); TTA-CAG-GGC-ATT-GAA-GCC (Seq. ID No. 36); CAG-TTA-TGA-AGC-AGT-CTC (Seq. ID No. 37); CAC-ACC-AGA-AAA-AGC-AGT (Seq. ID No. 38); AAG-GGT-AAA-CAC-TGT-GAG (Seq. ID No. 39); AGA-CAA-CGA-AAT-ATC-TTC-ATG (Seq. ID No. 40); CTA-GCA-GTA-TGA-GGT-CAA (Seq. ID No. 41); GCA-GAC-TTC-AGA-AAC-AGA (Seq. ID No. 42); GGC-CTC-AAA-GAC-GTT-TAA (Seq. ID No. 43); GTG-AAA-GTT-CCA-AGT-GAA (Seq. ID No. 44); GAG-TGC-TTT-GAA-GCC-TAC (Seq. ID No. 45); GAA-ACA-GCA-GAG-TTG-AAA (Seq. ID No. 46); TGC-AGA-GAT-CAC-AAC-GTG (Seq. ID No. 47); ACA-AAG-AAT-CAT-TCG-CAG (Seq. ID No. 48); AGT-GTT-AGA-AAA-CTG-CTC (Seq. ID No. 49); ACA-CGA-TTT-TGG-AAA-CAC (Seq. ID No. 119); CGA-AAC-ATC-ACT-GAG-AGT (Seq. ID No. 120); GGA-TGA-CAT-ATA-ATA-ACT-AG (Seq. ID No. 121); GAA-TTG-AAC-ATT-CAC-TTT-GA (Seq. ID No. 122); TAG-CTC-TGA-AGA-TTT-CGT (Seq. ID No. 123); GAG-ATG-TTT-CCG-AGA-ATG (Seq. ID No. 124); GTG-TAT-TCA-ACT-ACC-AGA (Seq. ID No. 125); ACA-TTT-CTG-TTA-CAG-AGC (Seq. ID No. 126); ATG-ACG-TAT-AAA-ATC-TAG-AG (Seq. ID No. 127); ACG-AAC-ACA-GTT-GAA-CCT (Seq. ID No. 128); CTC-ATA-AAA-ACC-AGA-AAG-AG (Seq. ID No. 129); CTG-TTC-AGA-GTA-ACA-TGA (Seq. ID No. 50); CCG-CTT-GGA-AAT-ACT-ACA (Seq. ID No. 51); GAA-ATG-GAA-ATA-TCT-CCC-C (Seq. ID No. 52); TCT-AGG-AGG-TCC-AAT-TAT (Seq. ID No. 53); GAA-TTC-CCA-AGT-GGA-TAT (Seq. ID No. 54); CTG-TAG-GTT-TAG-ATG-AAG (Seq. ID No. 55); AAG-GAG-TGT-TTC-CCA-ACT (Seq. ID No. 56); GGC-TTC-AAG-GCG-CTC-TAA (Seq. ID No. 57); GCA-GAG-ACT-TCA-AAG-TGC (Seq. ID No. 58); CAC-ACA-CAC-GGT-GGA-CCA (Seq. ID No. 59); CAA-AGG-GAA-TGT-TCC-ATT (Seq. ID No. 60); CAC-ATA-GCA-GTG-TTT-GAG (Seq. ID No. 61); CTC-AAG-GCG-GTC-CAA-TTA (Seq. ID No. 62); GAG-TCG-AAA-TGC-ACA-CAT (Seq. ID No. 63); TAC-CAA-GAG-GAA-TGT-TGC (Seq. ID No. 64); CAG-TTC-ATA-TGT-GCA-GTG (Seq. ID No. 130); GGA-ATA-TCG-TCA-CCT-AAA (Seq. ID No. 131); TGG-AGC-AAA-TTG-AAG-CCT (Seq. ID No. 132); TGG-AGC-ACA-TTT-ATG-CCT (Seq. ID No. 133); TGC-ATT-CTA-CTC-CCA-TAG (Seq. ID No. 134); ACA-CTC-TGT-TTC-TAA-AAT-CT (Seq. ID No. 135); GCA-GGC-GGA-TAT-TTA-GTA (Seq. ID No. 136); AGC-GAT-TTG-ATG-CCA-ACA (Seq. ID No. 137); TTG-CAA-ACG-GGG-TTT-CTT (Seq. ID No. 138); CTT-TCA-TGC-TAG-ACA-GAA (Seq. ID No. 139); CAA-AAA-AGT-TAC-TGA-GAA-C (Seq. ID No. 140); AAA-ATG-CCA-CAG-CAA-GAG (Seq. ID No. 141); GTT-TGA-AAA-CAC-ACT-GTT-TG (Seq. ID No. 142); ATA-TGG-ACC-TGT-TTG-AGG (Seq. ID No. 143); CAT-TGA-ATG-CTA-GAC-GGA (Seq. ID No. 144); ACG-GGA-TGC-AAT-ATA-AAA (Seq. ID No. 65); TGA-AGA-TTC-TGC-ATA-CGG (Seq. ID No. 66); AAG-GTT-TGT-ACT-GAC-AGA (Seq. ID No. 67); CTG-AAC-TAT-GGT-GAA-AAA (Seq. ID No. 68); ACT-AAC-TGT-GCT-GAA-CAT (Seq. ID No. 69); CCC-ATG-AAT-GCG-AGA-TAG (Seq. ID No. 70); ATG-ATG-AAA-AAG-GTA-ATA-E (Seq. ID No. 145); CAT-TCT-CAG-AAC-TGT-TTG-E (Seq. ID No. 146); AAC-TGA-ACG-CAC-AGA-TGA (Seq. ID No. 71); GGC-TAA-TCT-TTG-AAA-TTG-AAA (Seq. ID No. 72); AGG-TGG-ATA-ATT-GGC-CCT (Seq. ID No. 73); TGA-AGT-CCA-AAA-AAG-CAC (Seq. ID No. 74); CTT-AGA-CAT-GGA-AAT-ATC (Seq. ID No. 75); AAG-GGG-TCT-AAC-TAA-TCA (Seq. ID No. 76); GTA-GTT-GTT-GAG-AAT-GAT (Seq. ID No. 77); AAC-TTC-CCA-GAA-CTA-CAC (Seq. ID No. 78); ATT-CTT-GAA-ATG-GAA-CAC (Seq. ID No. 79); CTG-TGA- TTG-CTG-ATT-TGG (Seq. ID No. 80); GTC-ATC-ACA-GGA-AAC-ATT (Seq. ID No. 81); GAA-ATT-TCC-TGT-TGA-CAG-A (Seq. ID No. 82); GTT-TGA-AAG-CTG-AAC-TAT-G (Seq. ID No. 83); TCC-TGT-AAT-GTT-CGA-CAG (Seq. ID No. 84); TCA-TAG-AAC-GCT-AGA-AAG (Seq. ID No. 85); ACC-TTT-CTT-TTG-ATG-AAG-GA (Seq. ID No. 86); CAA-ATA-TCA-CAA-AAA-GAG-GG (Seq. ID No. 87); GAG-TTG-AAT-AGA-GGC-AAC (Seq. ID No. 88); GGC-CAA-ATG-TAG-AAA-AGG (Seq. ID No. 89); GCG-TTC-AAC-TCA-AGG-TGT (Seq. ID No. 90); TGT-CCT-TTA-GAC-AGA-GCA (Seq. ID No. 91); TGA-GAC-CAA-ATG-TAC-AAA-AG (Seq. ID No. 92); GAA-TAC-TGA-GTA-AGT-TCT-TTG (Seq. ID No. 93); AAC-TGC-ACA-AAT-AGG-GTG (Seq. ID No. 94); TGG-AGA-CAC-TGT-GTT-TGT (Seq. ID No. 95); CCA-GTT-GGA-GAT-TX-AAT (Seq. ID No. 96); GAA-GCC-TGC-CAG-TGG-ATA (Seq. ID No. 97); TAC-AGC-ATT-CTG-GAA-ACC (Seq. ID No. 98); CCA-GAC-ACT-GCG-TAG-TGA (Seq. ID No. 99); ATA-TAA-TGC-TAG-AGG-GAG (Seq. ID No. 100); AAA-AAC-AAG-ACA-AAC-TCG (Seq. ID No. 101); ATT-TCA-GCT-GAC-TAA-ACA (Seq. ID No. 102); AAC-GAA-TTA-TGG-TCA-CAT (Seq. ID No. 103); GGT-GAC-GAC-TGA-GTT-TAA (Seq. ID No. 104); TTT-GGA-CCA-CTC-TGT-GGC (Seq. ID No. 105); AAC-GGG-ATA-ACT-GCA-CCT (Seq. ID No. 106); TTT-GTG-GTT-TGT-GGT-GGA (Seq. ID No. 107); AGG-GAA-TAG-CTT-CAT-AGA (Seq. ID No. 108); ATC-ACG-AAG-AAG-GTT-CTG (Seq. ID No. 109); CCG-AAG-ATG-TCT-TTG-GAA (Seq. ID No. 110); AAA-GAG-GTC-TAC-ATG-TCC (Seq. ID No. 111); TTC-CCG-TAA-CAA-CTA-TGC (Seq. ID No. 112); TCC-CGT-AAC-AAC-TAG-GCA (Seq. ID No. 113); AAA-AGG-AGT-GAT-CCA-ACC (Seq. ID No. 114); TCC-CTT-TGG-TAG-AGC-AGG (Seq. ID No. 115); ATT-TGA-GAT-GTG-TGT-ACT-CA (Seq. ID No. 116); GCA-CTT-ACC-GGC-CTA-AG (Seq. ID No. 117); CTC-AGA-AAC-TTA-CTC-GTG (Seq. ID No. 118); ACA-GAA-CTA-AAC-CAT-CGT (Seq. ID No. 147); TAG-GCC-AGC-TTG-GAG-GAT (Seq. ID No. 148); CTA-GCT-GGG-AGG-ATT-T (Seq. ID No. 149); TGT-GCC-TCA-ACT-GAC-A-E (Seq. ID No. 150); TGC-TTT-GGG-ATG-TTT-CAA (Seq. ID No. 151); GCA-ATG-TCA-GAA-CTT-TTT-TC (Seq. ID No. 152); CCG-AAA-GAA-ATT-TGT-GGG (Seq. ID No. 153); GAA-CAT-GGC-CTT-TCA-TAG (Seq. ID No. 154); TCA-AGG-CGA-TCG-AAA-TGT (Seq. ID No. 155); GAG-ACA-CAT-ATC-ACC-AAC (Seq. ID No. 156); CAG-AAA-TTT-CTT-TCG-GAT-A (Seq. ID No. 157); GAA-CAT-GGC-CTT-TCA-TAG (Seq. ID No. 158) and AGC-CAA-AGG-AGT-TGA-ACA (Seq. ID No. 159).

Exemplary probe sets specific to each chromosome or pair of chromosomes and preferred probing nucleobase sequences suitable for the preparation of chromosome specific non-nucleic acid probes have previously been described herein. In a preferred embodiment, the method can be multiplexed to provide specific detection, identification and/or quantitation of each of chromosomes X, Y, 1, 2, 3, 4, 6, 7, 8, 9, 10, 11, 12, 16, 17, 18 and/or 20, as well as a 13/21 as a pair, in a single assay provided that the non-nucleic acid probes for a particular chromosome (X, Y, 1, 2, 3, 4, 6, 7, 8, 9, 10, 11, 12, 16, 17, 18 and/or 20, as well as 13/21 as a pair) are independently detectable. In a preferred embodiment, non-nucleic acid probes used to detect each of the identified chromosomes or pair of chromosomes are each labeled with one or more independently detectable fluorophores to thereby enable correlation of signal from a particular fluorophore, or set of fluorophores, with the presence, absence and/or quantity of a particular chromosome or pair of chromosomes. The grouping of non-nucleic acid probes within probe sets characterized for detecting, identification and/or quantitation or one, two or all of chromosomes X, Y, 1, 2, 3, 4, 6, 7, 8, 9, 10, 11, 12, 16, 17, 18 and 20 (as well as 13/21 as a pair) in the same assay is contemplated as a preferred embodiment of this invention. Most preferably, the set of non-nucleic acid probes is designed to detect, identify and/or quantitate most or all the human chromosomes from one or more samples in a single assay (e.g. a multiplex assay).

Exemplary Assay Formats:

The probes, probe sets, methods and kits of this invention are suitable for the detection, identification and quantitation of human chromosomes X, Y, 1, 2, 3, 4, 6, 7, 8, 9, 10, 11, 12, 16, 17, 18 and/or 20, as well as 13/21 as a pair. In preferred embodiments, in-situ hybridization is used as the assay format for detecting identifying and/or quantitating chromosomes in a sample. Most preferably, fluorescence in-situ hybridization (FISH or PNA-FISH) is the assay format. Exemplary methods for performing PNA-ISH can be found in: Thisted et al. Cell Vision, 3: 358-363 (1996), WIPO Patent Application WO97/18325, now U.S. Pat. No. 5,888,733, herein incorporated by reference or WIPO Patent Application WO97/14026, herein incorporated by reference.

Methods used to experimentally test the non-nucleic acid probes of this invention in PNA-FISH assays can be found in Examples 9 and 10 of this specification. FIGS. 1-21 demonstrate that labeled non-nucleic acid probes comprising the probing nucleobase sequences listed in Table 1 (actual PNA probe compositions are listed in Table 2) are specific for the human chromosome or pair of chromosomes sought to be detected. Furthermore, the speed and reproducibility of the protocol and the unambiguous results achieved using the non-nucleic acid probes of this invention is believed to be superior to those typically achieved with nucleic acid probes. Using previously fixed cells, the experimental conditions used in the Examples will yield results within approximately 1-2 hours. Furthermore, the assays performed were found to be sensitive, reliable, reproducible and generally applicable without regard to the substantial variability in sequence length or composition or label of the numerous probes tested (159 probing nucleobase sequences made and tested with a variability in length of 16 to 23 nucleobases including the analysis of three different labeling reagents (Cy5, Flu and Rox). This is a very surprising result given that the same assay conditions were found to be suitable for specific detection of different chromosomes using no less than 159 non-nucleic acid probes of such dramatically different composition.

Samples that have been treated with the non-nucleic acid probes or probe sets contained in the kits of this invention can be detected by several exemplary methods. Samples of cells or tissues can be fixed on slides and then visualized with a microscope or laser scanning device. Alternatively, the samples or cells can be fixed and then analyzed in a flow cytometer (See for example: Lansdorp et al.; WIPO Patent Application; WO97/14026). Slide scanners and flow cytometers are particularly useful for rapidly quantitating the number of total chromosomes or individual types of chromosomes (e.g. 1, 2, X, Y etc.) present in a single sample of interest.

d. Kits:

In yet another embodiment, this invention is directed to kits suitable for performing an assay which detects the presence, absence and/or number of human chromosomes X, Y, 1, 2, 3, 4, 6, 7, 8, 9, 10, 11, 12, 16, 17, 18 and/or 20, as well as 13/21 as a pair, in a sample or in the individual cells of a sample. The general and preferred characteristics of non-nucleic acid probes suitable for the detection, identification or quantitation of the indicated human chromosomes have been previously described herein. Preferred probing nucleobase sequences are listed in Table 1. Furthermore, methods suitable for using the non-nucleic acid probes or probes sets of a kit to detect, identify and/or quantitate the indicated human chromosomes have been previously described herein. Preferably, the kits are used in an assay suitable for simultaneous detection, identification and/or quantitation of all human chromosomes and most preferably the assay is an automated PNA-FISH assay. Most preferably, the assay is automated and performed using either a slide scanner based analysis system, microscope and CCD camera or a flow cytometer.

The kits of this invention comprise one or more non-nucleic acid probes and optionally one or more other reagents or compositions that are selected to perform an assay or otherwise simplify the performance of an assay used to detect, identify and/or quantitate human chromosomes X, Y, 1, 2, 3, 4, 6, 7, 8, 9, 10, 11, 12, 16, 17, 18 and/or 20, as well as 13/21 as a pair, in a sample. In kits that contain sets of non-nucleic acid probes wherein each of at least two probes of the set are used to distinctly detect, identify and/or quantitate each of the identified chromosomes or pair of chromosomes in the same sample and in the same assay, each of the probes of the set are preferably labeled with one or more independently detectable moieties. In a preferred embodiment, non-nucleic acid probes of a kit which are used to detect each of chromosomes X, Y, 1, 2, 3, 4, 6, 7, 8, 9, 10, 11, 12, 16, 17, 18 and/or 20, as well as 13/21 as a pair, are each labeled with one or more independently detectable fluorophores to thereby enable correlation of the presence of signal from a particular fluorophore, or set of fluorophores, with the presence, absence and/or quantity of the chromosome or pair of chromosomes sought to be detected.

e. Multiplex Assays

In still another embodiment, this invention is directed to a multiplex assay suitable for detecting, identifying and/or enumerating at least two different human chromosomes in the same assay and in the same sample using at least two non-nucleic acid probes which are independently detectable. In preferred embodiments, each of the two or more probes can detect the presence, absence and/or number of two human chromosomes in the same sample and in the same assay. Preferably, the multiplex assay is a PNA-ISH or PNA FISH assay.

Examples 9 and 10 of this specification demonstrate the feasibility of multiplex fluorescent in-situ hybridization using independently detectable PNA probes. The Figures which are to be viewed in connection with the description of these Examples conclusively demonstrate that individual human chromosomes are unambiguously detected in the sample wherein chromosomes X, Y and 1 are individually quantifiable both within the cells and the metaphase spreads.

f. Unique Multi-Labeled Non-Nucleic Acid Probes

In still one more embodiment, this invention is directed to non-nucleic acid probes comprising two or more linked independently detectable moieties wherein the combination of the two or more linked independently detectable moieties is used to identify a particular probe/target sequence hybrid since the combination of the two or more linked moieties is unique. Preferably the independently detectable moieties are independently detectable fluorophores. The uniquely labeled non-nucleic acid probes are particularly well suited for use in a multiplex assay.

g. Exemplary Applications for Using the Invention

Whether support bound or in solution, the non-nucleic acid probes, probe sets, methods and kits of this invention are particularly useful for the rapid, sensitive and reliable detection of human chromosomes X, Y, 1, 2, 3, 4, 6, 7, 8, 9, 10, 11, 12, 16, 17, 18 and/or 20, as well as 13/21 as a pair. Thus, the non-nucleic acid probes, probe sets, methods and kits of this invention can be used to detect or identify chromosome related abnormalities. Non-limiting examples of chromosome related abnormalities which can be detected using this invention include aneuploidy karyotypes and polyploidy karyotypes. Additionally, the non-nucleic acid probes, probe sets, methods and kits of this invention are particularly useful for preimplantation diagnosis, for prenatal screening or for use in clinical diagnostic applications.

Having described the preferred embodiments of the invention, it will now become apparent to one of skill in the art that other embodiments incorporating the concepts described herein may be used. It is felt, therefore, that these embodiments should not be limited to disclosed embodiments but rather should be limited only by the spirit and scope of the following claims.

EXAMPLES

This invention is now illustrated by the following examples which are not intended to be limiting in any way.

Example 1

Synthesis of bis-(2-methoxyethyl)amidyl-diglycolic acid

To 500 mmol of diglycolic anhydride stirring in 800 mL of dichloromethane (DCM) was added dropwise, 1.1 mole of bis(2-methoxyethyl)amine (Aldrich Chemical). The reaction was allowed to stir for 2 hours and then 280 mL of 6N HCl was added dropwise. The contents were then transferred to a separatory funnel and allowed to separate. The DCM layer was removed and the aqueous layer extracted with 100 mL of DCM. The combined DCM layers were then extracted with 100 mL of 10% aqueous citric acid. The DCM layer was then separated, dried ($Na_2SO_4$), filtered and evaporated to yield 73.8 g (296 mmole; 59% yield). A kugelrorh was then used to remove traces of solvent (product was heated to 60° C. at approximately 180 µM Hg; but not distilled).

Example 2

Synthesis of N—[N"-Fmoc-(2"-aminoethyl)]-N—[N,N'-(2-methoxyethyl)amidyl-diglycolyl]glycine ("Fmoc-"E"aeg-OH")

To 60 mmol of Fmoc-aeg-OH (PerSeptive Biosystems, Inc.) was added 360 mL of MilliQ water, 180 mL of acetone, 120 mmol of $NaHCO_3$ and 60 mmol of $K_2CO_3$. This solution was allowed to stir until all the Fmoc-aeg-OH had dissolved (approx. 2 hr.) and then the solution prepared, as described below, was added.

To 70 mmol of bis-(2-methoxyethyl)amidyl-diglycolic acid was added 120 mL of anhydrous acetonitrile (Fluka Chemical), 240 mmol of N-methylmorpholine (NMM; Fluka Chemical) and 75 mmol of trimethylacetyl chloride (Aldrich Chemical). The solution was allowed to stir at room temperature for 30 minutes and then added dropwise to the solution of Fmoc-aeg-OH which was prepared as described above.

After the combined solutions stirred for 1 hr and tlc analysis indicated complete reaction, 6N HCl was added to the reaction until the pH was less than 2 by paper. The organic solvent was then removed by vacuum evaporation. The remaining aqueous solution was then transferred to a separatory funnel and extracted 2x with 250 mL of ethyl acetate. The combined ethyl acetate layers were dried (Na$_2$SO$_4$), filtered and evaporated to yield 41.5 g of an oil.

This crude product was purified by column chromatography using a reversed phase stationary phase (C18) and a gradient of aqueous acetonitrile to elute the product and remove the pivalic acid. Though not visible by tlc, the elution of the pivalic acid can be monitored by smell. The pivalic acid can be almost completely eluted from the column prior to elution of the product. Elution of the product can be monitored by tlc. Yield 26.8 g (47 mmol; 78%). This "Fmoc-"E"aeg-OH" monomer was used directly on the PNA synthesis instrument, using standard condensation conditions, or used to prepare prederivatized synthesis supports which were used for the preparation of C-terminally "E" modified PNAs. An "E" modification (subunit) of a PNA or polyamide has the formula:

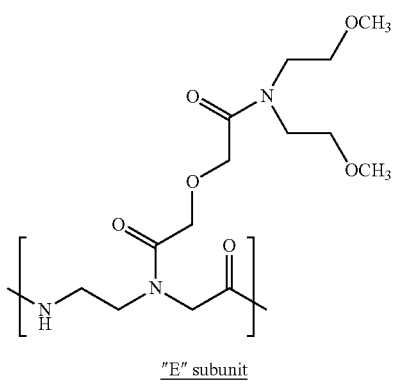

"E" subunit

Example 3

Synthesis of PNAs

Unless, otherwise stated, PNAs were synthesized using commercially available reagents and instrumentation obtained from PerSeptive Biosystems, Inc., Framingham, Mass., USA. Double couplings were routinely performed to improve the quality of the crude products. PNAs possessing "E" modifications were prepared by performing the synthesis using prederivatized synthesis support or by performing the synthesis using Fmoc-"E"aeg-OH (prepared as described above) monomers. PNAs possessing C-terminal fluorescein (bis-fluorescein labeled PNAs) were prepared by performing the synthesis using the Fmoc-K(Mtt)-OH (Bachem, Torrance, Calif., USA, P/N B-2535). Prior to performing the standard labeling procedure, the Mtt protecting group was removed using the following protocol. (See Note: Below)

The resin (still in the synthesis column) was treated with 10 mL of a solution containing 1% trifluoroacetic acid, 5% triisopropylsilane (TIS) in dichloromethane by passing the solution through the column over a period of approximately 15 minutes. After treatment, the synthesis support was washed with DMF. Prior to treatment with labeling reagent (See: Example 5), the support was neutralized by treatment with approximately 10 mL of a solution containing 5% diisopropylethylamine in DMF.

Note: This procedure was only performed on PNA prepared using Fmoc-PAL-PEG/PS (PE Biosystems, Foster City, Calif. P/N GEN913384). It was not performed with Fmoc-XAL-PEG/PS (PE Biosystems, Foster City, Calif. P/N GEN913394).

Example 4

Preferred Method for Removal of the Fmoc Protecting Group

The synthesis support was treated with a solution of 25% piperidine in DMF for 10-15 minutes at room temperature. After treatment, the synthesis support was washed and dried under high vacuum. The support can then be treated with labeling reagent (See: Example 5).

Example 5

Preferred Method for Amine Labeling of Support Bound PNA with the NHS esters of 5(6)carboxyfluorescein (Flu) or 5(and 6)-carboxy-X-rhodamine (Rox)

The amino protecting group (Fmoc) of the assembled PNA was removed and the synthesis support was washed and dried under vacuum. The synthesis support was then treated for 4-5 hours at 30-37° C. with approximately 250 μL of a solution containing 0.08 M NHS ester labeling reagent, 0.24 M DIEA and 0.24 M 2,6-lutidine. After treatment the synthesis support was washed and dried under high vacuum. The PNA oligomer was then cleaved, deprotected and purified.

Example 6

General Procedure for Labeling of Support Bound PNA with 5(6)carboxyfluorescein

After proper reaction with linkers and removal of the terminal amine protecting group, the resin was treated with 250 μL of a solution containing 0.5M 5(6)carboxyfluorescein, 0.5M N,N'-diisopropylcarbodiimide, 0.5M 1-hydroxy-7-azabenzotriazole (HOAt) in DMF (See: Weber et al., *Bioorganic & Medicinal Chemistry Letters,* 8: 597-600 (1998).

After treatment the synthesis support was washed and dried under high vacuum. The PNA oligomer was then cleaved, deprotected and purified as described below.

Note on Fluorescein Labeling: The fluorescein labeled PNAs described herein were prepared using several different procedures. The different procedures have evolved to optimize fluorescein labeling conditions. At this time we prefer to use the procedure of Weber et al., as modified, for most fluorescein labeling operations.

Example 7

General Procedure for Cleavage, Deprotection and Purification

The synthesis support (Fmoc-PAL-PEG/PS; P/N GEN913384) was then removed from the synthesis cartridge, transferred to a Ultrafree spin cartridge (Millipore Corp., P/N SE3P230J3) and treated with a solution of TFA/m-cresol (either of 7/3 or 8/2 (preferred)) for 1-3 hours. The solution was spun through the support bed and again the support was treated with a solution of TFA/m-cresol for 1-3 hours. The solution was again spun through the support bed. The combined eluents (TFA/m-cresol) was then precipitated by addition of approximately 1 mL of diethyl ether. The precipitate was pelletized by centrifugation. The pellet was then resuspended in ethyl ether and pelletized two additional times. The dried pellet was then resuspended in 20% aqueous acetonitrile (ACN) containing 0.1% TFA (additional ACN was added as necessary to dissolve the pellet). The product was analyzed and purified using conventional reversed phase chromatographic methods.

Note: Several PNAs were prepared using new product Fmoc-XAL-PEG/PS synthesis support (P/N GEN 913394) available from PerSeptive. This support has the advantage that the PNA can be removed more rapidly and under more mildly acid conditions. For PNAs prepared with Fmoc-XAL-PEG/PS the support is treated as described above except that a solution of TFA/m-cresol 9/1 was used for a period of 10-15 minutes (2×).

Example 8

Cy5 Labeling of PNAs

The purified amine containing PNA was dissolved in 1/1 DMF/water at a concentration of approximately 0.05 OD/μL to prepare a stock PNA solution. From the stock, approximately 30 nmole of PNA was added to a tube. To this tube was then added 125 μl 0.1 M HEPES (pH 8.5), and enough 1/1 DMF/water to bring the total volume to 250 μL. This solution was thoroughly mixed. To a prepackaged tube of Cy5 dye (Amersham P/N PA-25001), was added the entire 250 μl solution prepared as described above. The tube was well mixed and then allowed to react for 1 hour at ambient temperature.

After reaction, the solvent was removed by evaporation in a speed-vac. The pellet was then dissolved in 400 μL of a solution containing 3:1 1% aqueous TFA/ACN. Optionally the solution was then transferred to a 5000 MW Ultrafree (Millipore, P/N UFC3LCC25) or a 3000 MW (Amicon, P/N 42404) filter to removed excess dye. The recovered product was then repurified using reversed phase chromatographic methods.

Example 9

PNA-FISH Used for the Detection of Human Chromosomes X, Y, 1, 2, 3, 4, 6, 7, 8, 9, 10, 11, 12, 16, 17, 18 and 20, as Well as 13/21 as a Pair PNA Oligomers Prepared

TABLE 2

| Probe ID | Target Human Chromosome | PNA Probe Sequence |
|---|---|---|
| Rox-X-I | X | Rox-OE-CTT-CAA-AGA-GGT-CCA-CGA-E-NH$_2$ |
| Rox-X-II | X | Rox-OEE-AGG-GTT-CAA-CTG-TGT-GAC-E-NH$_2$ |
| Rox-X-III | X | Rox-OEE-GAA-ACT-TCT-GAG-TGA-TGA-EE-NH$_2$ |
| Rox-X-VI | X | Rox-OEE-CAG-TCA-TCG-CAG-AAA-ACT-EE-NH$_2$ |
| Rox-X-V | X | Rox-OEE-AGA-TTT-CAC-TGG-AAA-CGG-EE-NH$_2$ |
| Rox-X-VI | X | Rox-OEE-GTT-ATG-GGA-AGG-TGA-TCC-EE-NH$_2$ |
| Rox-X-VII | X | Rox-OEE-TCG-AGC-CGC-AGA-GTT-TAA-EE-NH$_2$ |
| Rox-X-VIII | X | Rox-OEE-CTA-TTT-AGC-GGG-CTT-GGA-EE-NH$_2$ |
| Rox-X-IX | X | Rox-OEE-TAC-AAG-GGT-GTT-GCA-AAC-EE-NH$_2$ |
| Flu-Y-I | Y | Flu-OE-CCA-TAT-GCA-GTT-ATA-AGT-AGG-E-NH$_2$ |
| Flu-Y-II | Y | Flu-OE-TAT-TGT-ACC-AAG-CAG-AGT-ACC-E-NH$_2$ |
| Flu-Y-III | Y | Flu-OEE-GGT-ATA-TAT-AAG-ATG-ACA-CAG-GA-EE-NH$_2$ |
| Flu-Y-IV | Y | Flu-OEE-GTT-AGT-TAT-ATT-GGG-TGA-TAT-GT-EE-NH$_2$ |
| Flu-Y-V | Y | Flu-OEE-TCA-CAT-AAT-AGA-CAA-CAT-AC-EE-NH$_2$ |
| Flu-Y-VI | Y | Flu-OEE-CAG-AAG-AGA-TTG-AAC-CTT-EE-NH$_2$ |
| Flu-Y-VII | Y | Flu-OEE-GGC-ATA-GCA-CAT-AAC-ATG-EE-NH$_2$ |
| Rox-1-I | 1 | Rox-OE-AAT-CGT-CAT-CGA-ATG-AAT-E-NH$_2$ |
| Rox-1-II | 1 | Rox-OE-CAT-TGA-ACA-GAA-TTG-AAT-E-NH$_2$ |
| Cy5-1-I | 1 | Cy5-OE-AAT-CGT-CAT-CGA-ATG-AAT-E-NH$_2$ |
| Cy5-1-II | 1 | Cy5-OE-CAT-TGA-ACA-GAA-TTG-AAT-E-NH$_2$ |
| Flu-2-I | 2 | Flu-OEE-GTT-TTC-AGG-GGA-AGA-TAT-EEO-K(Flu)-NH$_2$ |
| Flu-2-II | 2 | Flu-OEE-TGT-GCG-CCC-TCA-ACT-AAC-EEO-K(Flu)-NH$_2$ |
| Flu-2-III | 2 | Flu-OEE-GAA-GCT-TCA-TTG-GGA-TGT-EE-NH$_2$ |
| Flu-2-IV | 2 | Flu-OEE-CCA-ATA-AAA-GCT-ACA-TAG-A-EEO-K(Flu)-NH$_2$ |
| Flu-2-V | 2 | Flu-OEE-GAA-AAA-GTT-TCT-GAC-ATT-GC-EE-NH$_2$ |
| Flu-2-VI | 2 | Flu-OEE-TAG-TTG-AAG-GGC-ACA-TCA-EE-NH$_2$ |
| Flu-2-VII | 2 | Flu-OEE-CAC-AAA-TAA-GAT-TCT-AAG-AAT-EE-NH$_2$ |
| Flu-2-VIII | 2 | Flu-OEE-TCA-AAA-GAA-TGC-TTC-AAC-AC-EE-NH$_2$ |
| Rox-3-I | 3 | Rox-OEE-ATA-ATT-AGA-CCG-GAA-TCA-T-E-NH$_2$ |
| Rox-3-II | 3 | Rox-OEE-GCT-GTT-TTC-TAA-AGG-AAA-G-EE-NH$_2$ |
| Rox-3-III | 3 | Rox-OEE-AAG-ACT-TCA-AAG-AGG-TCC-E-NH$_2$ |
| Flu-3-I | 3 | Flu-OEE-TTT-GTC-AAG-AAT-TAT-AAG-AAG-EE-NH$_2$ |
| Flu-3-II | 3 | Flu-OEE-CAA-GAT-TGC-TTT-TAA-TGG-EE-NH$_2$ |
| Flu-3-III | 3 | Flu-OEE-TGT-GTA-TCA-ACT-CAC-GGA-EE-NH$_2$ |
| Flu-3-IV | 3 | Flu-OEE-CCT-CAC-AAA-GTA-GAA-ACT-EE-NH$_2$ |
| Flu-3-V | 3 | Flu-OEE-GAA-AAA-GCA-GTT-ACT-GAG-EE-NH$_2$ |
| Flu-3-VI | 3 | Flu-OEE-TAA-TAA-TTA-GAC-GGA-ATC-AT-EE-NH$_2$ |
| Flu-3-VII | 3 | Flu-OEE-TTA-CAG-GGC-ATT-GAA-GCC-EE-NH$_2$ |
| Flu-3-VIII | 3 | Flu-OEE-CAG-TTA-TGA-AGC-AGT-CTC-EE-NH$_2$ |
| Flu-3-IX | 3 | Flu-OEE-CAC-ACC-AGA-AAA-AGC-AGT-EE-NH$_2$ |
| Flu-3-X | 3 | Flu-OEE-AAG-GGT-AAA-CAC-TGT-GAG-EE-NH$_2$ |
| Flu-3-XI | 3 | Flu-OEE-AGA-CAA-CGA-AAT-ATC-TTC-ATG-EE-NH$_2$ |
| Flu-3-XII | 3 | Flu-OEE-CTA-GCA-GTA-TGA-GGT-CAA-EE-NH$_2$ |
| Flu-3-XIII | 3 | Flu-OEE-GCA-GAC-TTC-AGA-AAC-AGA-EE-NH$_2$ |

TABLE 2-continued

| Probe ID | Target Human Chromosome | PNA Probe Sequence |
|---|---|---|
| Flu-3-XIV | 3 | Flu-OEE-GGC-CTC-AAA-GAC-GTT-TAA-EE-NH$_2$ |
| Flu-3-XV | 3 | Flu-OEE-GTG-AAA-GTT-CCA-AGT-GAA-EE-NH$_2$ |
| Flu-3-XVI | 3 | Flu-OEE-GAG-TGC-TTT-GAA-GCC-TAC-EE-NH$_2$ |
| Flu-3-XVII | 3 | Flu-OEE-GAA-ACA-GCA-GAG-TTG-AAA-EE-NH$_2$ |
| Flu-3-XVIII | 3 | Flu-OEE-TGC-AGA-GAT-CAC-AAC-GTG-EE-NH$_2$ |
| Flu-3-XIX | 3 | Flu-OEE-ACA-AAG-AAT-CAT-TCG-CAG-EE-NH$_2$ |
| Flu-3-XX | 3 | Flu-OEE-AGT-GTT-AGA-AAA-CTG-CTC-EE-NH$_2$ |
| Flu-4-I | 4 | FLU-OEE-ACA-CGA-TTT-TGG-AAA-CAC-EE-NH$_2$ |
| Flu-4-II | 4 | FLU-OEE-CGA-AAC-ATC-ACT-GAG-AGT-EE-NH$_2$ |
| Flu-4-III | 4 | FLU-OEE-GGA-TGA-CAT-ATA-ATA-ACT-AG-EE-NH$_2$ |
| Flu-4-IV | 4 | FLU-OEE-GAA-TTG-AAC-ATT-CAC-TTT-GA-EE-NH$_2$ |
| Flu-4-V | 4 | FLU-OEE-TAG-CTC-TGA-AGA-TTT-CGT-EE-NH$_2$ |
| Flu-4-VI | 4 | FLU-OEE-GAG-ATG-TTT-CCG-AGA-ATG-EE-NH$_2$ |
| Flu-4-VII | 4 | FLU-OEE-GTG-TAT-TCA-ACT-ACC-AGA-EE-NH$_2$ |
| Flu-4-VIII | 4 | FLU-OEE-ACA-TTT-CTG-TTA-CAG-AGC-EE-NH$_2$ |
| Flu-4-IX | 4 | FLU-OEE-ATG-ACG-TAT-AAA-ATC-TAG-AG-EE-NH$_2$ |
| Flu-4-X | 4 | FLU-OEE-ACG-AAC-ACA-GTT-GAA-CCT-EE-NH$_2$ |
| Flu-4-XI | 4 | FLU-OEE-CTC-ATA-AAA-ACC-AGA-AAG-AG-EE-NH$_2$ |
| Flu-6-I | 6 | Flu-OEE-CTG-TTC-AGA-GTA-ACA-TGA-EE-NH$_2$ |
| Flu-6-II | 6 | Flu-OEE-CCG-CTT-GGA-AAT-ACT-ACA-EE-NH$_2$ |
| Flu-6-III | 6 | Flu-OEE-GAA-ATG-GAA-ATA-TCT-CCC-C-E-NH$_2$ |
| Flu-6-IV | 6 | Flu-OEE-TCT-AGG-AGG-TCC-AAT-TAT-E-NH$_2$ |
| Flu-6-V | 6 | Flu-OEE-GAA-TTC-CCA-AGT-GGA-TAT-EE-NH$_2$ |
| Flu-6-VI | 6 | Flu-OEE-CTG-TAG-GTT-TAG-ATG-AAG-EE-NH$_2$ |
| Flu-6-VII | 6 | Flu-OEE-AAG-GAG-TGT-TTC-CCA-ACT-EE-NH$_2$ |
| Flu-6-VIII | 6 | Flu-OEE-GGC-TTC-AAG-GCG-CTC-TAA-EE-NH$_2$ |
| Flu-6-IX | 6 | Flu-OEE-GCA-GAG-ACT-TCA-AAG-TGC-EE-NH$_2$ |
| Flu-6-X | 6 | Flu-OEE-CAC-ACA-CAC-GGT-GGA-CCA-E-NH$_2$ |
| Flu-6-XI | 6 | Flu-OEE-CAA-AGG-GAA-TGT-TCC-ATT-EE-NH$_2$ |
| Flu-6-XII | 6 | Flu-OEE-CAC-ATA-GCA-GTG-TTT-GAG-EE-NH$_2$ |
| Flu-6-XIII | 6 | Flu-OEE-CTC-AAG-GCG-GTC-CAA-TTA-E-NH$_2$ |
| Flu-6-XIV | 6 | Flu-OEE-GAG-TCG-AAA-TGC-ACA-CAT-E-NH$_2$ |
| Flu-6-XV | 6 | Flu-OEE-TAC-CAA-GAG-GAA-TGT-TGC-EE-NH$_2$ |
| Flu-7-I | 7 | FLU-OEE-CAG-TTC-ATA-TGT-GCA-GTG-EE-NH$_2$ |
| Flu-7-II | 7 | FLU-OEE-GGA-ATA-TCG-TCA-CCT-AAA-EE-NH$_2$ |
| Flu-7-III | 7 | FLU-OEE-TGG-AGC-AAA-TTG-AAG-CCT-EE-NH$_2$ |
| Flu-7-IV | 7 | FLU-OEE-TGG-AGC-ACA-TTT-ATG-CCT-EE-NH$_2$ |
| Flu-7-V | 7 | FLU-OEE-TGC-ATT-CTA-CTC-CCA-TAG-EE-NH$_2$ |
| Flu-7-VI | 7 | FLU-OEE-ACA-CTC-TGT-TTC-TAA-AAT-CT-EE-NH$_2$ |
| Flu-7-VII | 7 | FLU-OEE-GCA-GGC-GGA-TAT-TTA-GTA-EE-NH$_2$ |
| Flu-7-VIII | 7 | FLU-OEE-AGC-GAT-TTG-ATG-CCA-ACA-EE-NH$_2$ |
| Flu-7-IX | 7 | FLU-OEE-TTG-CAA-ACG-GGG-TTT-CTT-EE-NH$_2$ |
| Flu-7-X | 7 | FLU-OEE-CTT-TCA-TGC-TAG-ACA-GAA-EE-NH$_2$ |
| Flu-7-XI | 7 | FLU-OEE-CAA-AAA-AGT-TAC-TGA-GAA-C-EE-NH$_2$ |
| Flu-7-XII | 7 | FLU-OEE-AAA-ATG-CCA-CAG-CAA-GAG-EE-NH$_2$ |
| Flu-7-XIII | 7 | FLU-OEE-GTT-TGA-AAA-CAC-ACT-GTT-TG-EE-NH$_2$ |
| Flu-7-XIV | 7 | FLU-OEE-ATA-TGG-ACC-TGT-TTG-AGG-EE-NH$_2$ |
| Flu-7-V | 7 | FLU-OEE-CAT-TGA-ATG-CTA-GAC-GGA-EE-NH$_2$ |
| Rox-8-I | 8 | Rox-OE-ACG-GGA-TGC-AAT-ATA-AAA-E-NH$_2$ |
| Rox-8-II | 8 | Rox-OE-TGA-AGA-TTC-TGC-ATA-CGG-E-NH$_2$ |
| Rox-8-III | 8 | Rox-OE-AAG-GTT-TGT-ACT-GAC-AGA-E-NH$_2$ |
| Rox-8-IV | 8 | Rox-OE-CTG-AAC-TAT-GGT-GAA-AAA-E-NH$_2$ |
| Rox-8-V | 8 | Rox-OE-ACT-AAC-TGT-GCT-GAA-CAT-E-NH$_2$ |
| Rox-8-VI | 8 | Rox-OE-CCC-ATG-AAT-GCG-AGA-TAG-E-NH$_2$ |
| Rox-9-I | 9 | RHO-OE-ATG-ATG-AAA-AAG-GTA-ATA-E-NH$_2$ |
| Rox-9-II | 9 | RHO-OE-CAT-TCT-CAG-AAC-TGT-TTG-E-NH$_2$ |
| Rox-10-I | 10 | Rox-OEE-AAC-TGA-ACG-CAC-AGA-TGA-EE-NH$_2$ |
| Rox-10-II | 10 | Rox-OEE-GGC-TAA-TCT-TTG-AAA-TTG-AAA-EE-NH$_2$ |
| Rox-10-III | 10 | Rox-OEE-AGG-TGG-ATA-ATT-GGC-CCT-EE-NH$_2$ |
| Rox-10-IV | 10 | Rox-OEE-TGA-AGT-CCA-AAA-AAG-CAC-EE-NH$_2$ |
| Rox-10-V | 10 | Rox-OEE-CTT-AGA-CAT-GGA-AAT-ATC-E-NH$_2$ |
| Rox-10-VI | 10 | Rox-OEE-AAG-GGG-TCT-AAC-TAA-TCA-E-NH$_2$ |
| Flu-10-VII | 10 | Flu-OEE-GTA-GTT-GTT-GAG-AAT-GAT-EE-NH$_2$ |
| Rox-11-I | 11 | Rox-OEE-AAC-TTC-CCA-GAA-CTA-CAC-EE-NH$_2$ |
| Rox-11-II | 11 | Rox-OEE-ATT-CTT-GAA-ATG-GAA-CAC-EE-NH$_2$ |
| Rox-11-III | 11 | Rox-OEE-CTG-TGA-TTG-CTG-ATT-TGG-EE-NH$_2$ |
| Rox-11-IV | 11 | Rox-OEE-GTC-ATC-ACA-GGA-AAC-ATT-EE-NH$_2$ |
| Rox-11-V | 11 | Rox-OEE-GAA-ATT-TCC-TGT-TGA-CAG-A-EE-NH$_2$ |
| Flu-11-I | 11 | Flu-OEE-GTT-TGA-AAG-CTG-AAC-TAT-G-E-NH$_2$ |
| Flu-12-I | 12 | Flu-OEE-TCC-TGT-AAT-GTT-CGA-CAG-EE-NH$_2$ |
| Flu-12-II | 12 | Flu-OEE-TCA-TAG-AAC-GCT-AGA-AAG-EE-NH$_2$ |
| Flu-12-III | 12 | Flu-OEE-ACC-TTT-CTT-TTG-ATG-AAG-GA-EE-NH$_2$ |
| Flu-12-IV | 12 | Flu-OEE-CAA-ATA-TCA-CAA-AAA-GAG-GG-EE-NH$_2$ |
| Flu-12-V | 12 | Flu-OEE-GAG-TTG-AAT-AGA-GGC-AAC-EE-NH$_2$ |
| Flu-12-VI | 12 | Flu-OEE-GGC-CAA-ATG-TAG-AAA-AGG-EE-NH$_2$ |
| Flu-12-VII | 12 | Flu-OEE-GCG-TTC-AAC-TCA-AGG-TGT-EE-NH$_2$ |

TABLE 2-continued

| Probe ID | Target Human Chromosome | PNA Probe Sequence |
|---|---|---|
| Flu-12-VIII | 12 | Flu-OEE-TGT-CCT-TTA-GAC-AGA-GCA-EE-NH$_2$ |
| Flu-12-IX | 12 | Flu-OEE-TGA-GAC-CAA-ATG-TAC-AAA-AG-EE-NH$_2$ |
| Flu-12-X | 12 | Flu-OEE-GAA-TAC-TGA-GTA-AGT-TCT-TTG-EE-NH$_2$ |
| Flu-12-XI | 12 | Flu-OEE-AAC-TGC-ACA-AAT-AGG-GTG-EE-NH$_2$ |
| Flu-12-XII | 12 | Flu-OEE-TGG-AGA-CAC-TGT-GTT-TGT-E-NH$_2$ |
| Flu-12-IX | 12 | Flu-OEE-CCA-GTT-GGA-GAT-TTC-AAT-E-NH$_2$ |
| Flu-16-I | 16 | Flu-OE-GAA-GCC-TGC-CAG-TGG-ATA-E-NH$_2$ |
| Flu-16-II | 16 | Flu-OE-TAC-AGC-ATT-CTG-GAA-ACC-E-NH$_2$ |
| Rox-16-I | 16 | Rox-OE-CCA-GAC-ACT-GCG-TAG-TGA-E-NH$_2$ |
| Rox-16-II | 16 | Rox-OE-ATA-TAA-TGC-TAG-AGG-GAG-E-NH$_2$ |
| Rox-16-III | 16 | Rox-OE-AAA-AAC-AAG-ACA-AAC-TCG-E-NH$_2$ |
| Flu-17-I | 17 | Flu-OE-ATT-TCA-GCT-GAC-TAA-ACA-E-NH$_2$ |
| Flu-17-II | 17 | Flu-OE-AAC-GAA-TTA-TGG-TCA-CAT-E-NH$_2$ |
| Flu-17-III | 17 | Flu-OE-GGT-GAC-GAC-TGA-GTT-TAA-E-NH$_2$ |
| Flu-17-IV | 17 | Flu-OEE-TTT-GGA-CCA-CTC-TGT-GGC-EE-NH$_2$ |
| Flu-17-V | 17 | Flu-OEE-AAC-GGG-ATA-ACT-GCA-CCT-EE-NH$_2$ |
| Flu-17-VI | 17 | Flu-OEE-TTT-GTG-GTT-TGT-GGT-GGA-EE-NH$_2$ |
| Flu-17-VII | 17 | Flu-OEE-AGG-GAA-TAG-CTT-CAT-AGA-EE-NH$_2$ |
| Flu-17-VIII | 17 | Flu-OEE-ATC-ACG-AAG-AAG-GTT-CTG-EE-NH$_2$ |
| Flu-17-XI | 17 | Flu-OEE-CCG-AAG-ATG-TCT-TTG-GAA-EE-NH$_2$ |
| Flu-17-X | 17 | Flu-OEE-AAA-GAG-GTC-TAC-ATG-TCC-EE-NH$_2$ |
| Flu-18-I | 18 | Flu-OEE-TTC-CCG-TAA-CAA-CTA-TGC-EE-NH$_2$ |
| Flu-18-II | 18 | Flu-OEE-TCC-CGT-AAC-AAC- TAG-GC A-EE-NH$_2$ |
| Flu-18-III | 18 | Flu-OEE-AAA-AGG-AGT-GAT-CCA-ACC-EE-NH$_2$ |
| Flu-18-IV | 18 | Flu-OEE-TCC-CTT-TGG-TAG-AGC-AGG-EE-NH$_2$ |
| Flu-18-V | 18 | Flu-OEE-ATT-TGA-GAT-GTG-TGT-ACT-CA-EE-NH$_2$ |
| Flu-18-VI | 18 | Flu-OEE-GCA-CTT-ACC-GGC-CTA-AG-EE-NH$_2$ |
| Flu-18-VII | 18 | Flu-OEE-CTC-AGA-AAC-TTA-CTC-GTG-EE-NH$_2$ |
| Flu-20-I | 20 | FLU-OEE-ACA-GAA-CTA-AAC-CAT-CGT-EE-NH$_2$ |
| Flu-20-II | 20 | FLU-OEE-TAG-GCC-AGC-TTG-GAG-GAT-EE-NH$_2$ |
| Flu-20-III | 20 | FLU-OEE-CTA-GCT-GGG-AGG-ATT-T-EE-NH$_2$ |
| Flu-20-IV | 20 | FLU-OEE-TGT-GCC-TCA-ACT-GAC-A-E-NH$_2$ |
| Flu-20-V | 20 | FLU-OEE-TGC-TTT-GGG-ATG-TTT-CAA-EE-NH$_2$ |
| Flu-20-VI | 20 | FLU-OEE-GCA-ATG-TCA-GAA-CTT-TTT-TC-EE-NH$_2$ |
| Flu-13/21-I | 13/21 | FLU-OEE-CCG-AAA-GAA-ATT-TGT-GGG-EE-NH$_2$ |
| Flu-13/21-II | 13/21 | FLU-OEE-GAA-CAT-GGC-CTT-TCA-TAG-EE-NH$_2$ |
| Flu-13/21-III | 13/21 | FLU-OEE-TCA-AGG-CGA-TCG-AAA-TGT-EE-NH$_2$ |
| Flu-13/21-IV | 13/21 | FLU-OEE-GAG-ACA-CAT-ATC-ACC-AAC-EE-NH$_2$ |
| Flu-13/21-V | 13/21 | FLU-OEE-CAG-AAA-TTT-CTT-TCG-GAT-A-EE-NH$_2$ |
| Flu-13/21-VI | 13/21 | FLU-OEE-GAA-CAT-GGC-CTT-TCA-TAG-EE-NH$_2$ |
| Flu-13/21-VII | 13/21 | FLU-OEE-AGC-CAA-AGG-AGT-TGA-ACA-EE-NH$_2$ |

PNA sequences are written from the amine (N-) terminus to the carboxyl (C-) terminus. K=the amino acid L-lysine; Flu=5(6)-carboxyfluorescein; Rox=5(and 6)-carboxy-X-rhodamine; Cy5 is the cyanine 5 dye obtained from Amersham/Pharmacia; O=8-amino-3,6-dioxaoctanoic acid and "E" has been previously described herein.

Preferred Method for Cytogenetic Preparations:

Human normal or patient cells were incubated in culture with 0.015 µg/mL colcemid for 45-60 min (Taneja et al., *The Journal of Cell Biology,* 12: 995-1002 (1995)). After incubation, media was removed in a 50 mL centrifuge tube. In case of fibroblast or attached cells, the cells were trypsinized with 0.5% trypsin-EDTA in Hank's Balanced Salt Solution (HBSS, Gibco, BRL). Trypsinized cells were added to the previously removed media to stop the trypsin reaction. Cells were then centrifuged at approximately 1000 rpm for 5 min and the cell pellet was resuspended in 10 mL of 0.075M KCl. Cells were incubated at 37° C. for 15 min, and again centrifuged at approximately 1000 rpm for 5 min. Ten milliliters of freshly prepared methanol/acetic acid (3:1) was then added drop by drop with mixing to the cell pellet. The cells were thereafter incubated at room temperature for 10 min and again centrifuged. Approximately 10 mL of methanol/acetic acid (3:1) was again added to the cells and then the cells were incubated for 10 min at room temperature. Cells were then centrifuged, the supernatant was removed, and the cell pellet resuspended in 1 mL of methanol/acetic acid (3:1). Cells were dropped onto ethanol washed slides and dried in air overnight. Finally, slides were incubated at 65° C. for one hour and stored at −80° C.

Design of Chromosome Specific Probes:

Probes for X chromosome were designed from the done pBamX7 of DXZ1 locus (Waye et al., *Nucl. Acids Res.,* 13: 2731-2743 (1985)) and were labeled with rhodamine (red). The pBamX7 clone is 2 kb alpha satellite DNA which hybridized to 5000 copies located in the centromeric region of X chromosome (Willard et al., 1986; *The Journal of Cell Biology et al.,* 1987). Probes for the Y chromosome were designed from 2.47 kb repeat sequences in DYZ2 locus (Frommer M., et al., 1984). The human Y chromosome carries 2000 copies of tandemly repeat sequences (a 2.47 kb fragment) and localized on the long arm of the Y chromosome (Cooke et al., *Chromosoma (Berl.)* 87: 491-502 (1982)). PNA probes for detecting the human Y chromosome were labeled with fluorescein (green). Chromosome 1 specific PNA probes were derived from the published human satellite 2 sequences (Jeanpierre M., *Ann. Genet,* 37: 1994). Satellite 2 DNA is present in the pericentric heterochromatin region on the long arm of chromosome 1 (1q12). Chromosome 1 specific probes were labeled with rhodamine or Cy5. Table 1 lists only those probing nucleobase sequences which, when tested in hybridizations assays, were found to be specific for the chromosomes sought to be detected. The target sequences for the chromosome specific probing nucleobase sequences (18-23 bases) listed in Table 1, were checked for cross hybridization using sequence alignment analysis. Probes for human chromosome 2 were designed from p2-11 (See: Haaf and Willard, *Genomics,* 13: 122-128 (1992)) and were labeled with fluorescein (green). The clone p2-11 is 1356 bp long and is part of the D2Z1 locus. The D2Z1 array spans about 1050-2900 kb of the centromere of chromosome 2. Probes for human chromosome 3 were designed from Gene Bank accession number M29460 (HS3ALPH, Smith et al., unpublished), M29461 (HS6ALPH, Smith et al., unpublished), and X06394 (HSREPA18, Delattre et al., *Nucleic Acid Research,* 15: 8561 (1987)) and were labeled with fluorescein. The clones (HS3ALPH (345 bp), HS6ALPH (676 bp) and HSREPA18 (635 bp)) are the part of alpha satellite sequences and localized at the centromere of chromosome 3. Chromosome 4 specific PNA probes were designed from two alpha satellite clones pYAM7-62 (685 bp) and pYAM3-84 (1184 bp), sequenced by Mashkova et al. (*Gene,* 140: 211-217, (1994)) and also from the clone p4n1/4 (675 bp) (D'Aiuto et al., *Genomics,* 18: 230-235, (1993)). Suitable probes directed to these alphoid sequences were prepared and labeled with fluorescein. Probes for human chromosome 6 were designed from clone 308 (See: Jabs and Persico, *Am. J. Hum. Genet,* 41: 374-390 (1987)) and were labeled with fluorescein (green). The clone 308 is a 2.9 kb Barn HI DNA fragment of higher order repeat unit consisting of 19 alphoid monomers. It is a part of D6Z1 locus and is located in the centromere of chromosome 6. Two clones pMGB7 (2.7 kbp, ~10 copies) and pα7t1 (340 bp, ~500 copies) of alpha satellite DNA have been identified by Waye et al. (*Molecular and Cellular Biology,* 7: 349-356, (1987)) and were located on the centromere of chromosome 7. Probes were designed to target repeat sequences within pMGB7 and pα7t1 and were labeled fluorescein (green). Chromosome 8 specific probes were taken from the gene Bank accession number M64779 (HSD8Z2AA, Ge et al., unpublished), originated from chromosome 8 and is a part of D8Z2 locus. The target to these probes is present on the centromere of chromosome 8. Rochhi et al. (*Genomics,* 9: 517-523, (1991)) have isolated and sequenced a DNA clone pMR9A (340 bp) that identified an alpha satellite DNA subset and located on the centromere of chromosome 9. PNA probes designed from pMR9A were labeled with rhodamine. Probes for human chromosome 10 were designed from the centromeric probe pα10RP8, a 912 bp clone in the D10Z1 locus (Howe et al., *Hum. Genet.,* 91: 199-204 (1993)), and were labeled with either fluorescein (green) or rhodamine (red). The pα10RP8 fragment is located in the centromeric region of chromosome 10. The principle repetitive unit of this alpha satellite subset is an 850 bp XbaI fragment (clone pLC11A, Waye et al., *Chromosoma,* 95: 182-188 (1987)) composed of five tandem diverged alphoid monomers; each of ~171 bp in length. The pentamer repeat units are themselves tandemly reiterated in ~500 copies per chromosome 11. These probes were specific for the centromeric alpha satellite sequences of chromosome 11. Chromosome 12 specific probes were taken from clone pGR12 (D12Z3). A 685 bp fragment of alpha satellite DNA sequences, (Gene Bank accession number M28221 (Rocchi et al., *Am. J. of Hum. Genet.* 46: 784-788, 1990)), originated from the chromosome 12 centromere. Probes for human chromosome 16 were designed from pSE-16-2 (See: Greig et al., *Am. J. Hum. Genet.,* 45: 862-872 (1989)) and were labeled with either fluorescein (green) or rhodamine (red). The clone pSE-16-2 is 340 bp long and is part of the D16Z2 locus. The D16Z2 array spans about 1400-2000 kb of the centromere of chromosome 16. Probes for human chromosome 17 were designed from p17H8 (See: Waye et al, *Molecular and Cellular Biology,* 6: 3156-3165 (1986)) and were labeled with fluorescein (green). The clone p17H8 is a 2.7 kb higher order repeat unit consisting of 16 alphoid monomers, which is 500-1000 copies located in the centromere of chromosome 17. Probes for human chromosome 18 were designed from the 1360 bp pst-1 insert of pYAM9-60 in the D18Z1 locus (Alexandrov et al., *Genomics,* 11: 15-23 (1991)) and were labeled with either fluorescein (green). The pYAM9-60 fragment is located in the centromeric region of chromosome 18. Chromosome 20 specific PNA probes were derived from the clone pZ20R (Baldini, A. GeneBank accession # X58269), clone p-alpha-H1 (Baldini et al. GeneBank accession # X56450) and from the clones SN2 &SN3 (Johnson 315 et al., *Hum. Mol. Genet.* 1: 741-747 (1992)), and were labeled with fluorescein (green). These sequences were located at the centromere of chromosome 20. The alpha satellite DNA higher order repeat unit clone pW29-19 shared by chromosomes 13 (D13Z1) and 21 (D21Z1) was examined in detail by Greig et al. (*J. Mol. Evol.,* 37: 464-475, (1993)). Ikeno et al. (Hum. Mol. Genet., 8:1245-1257) also identified the alpha satellite DNA higher order repeat unit clone p11-4 from chromosome 21, which also hybridize to chromosome 13. PNA probes were designed from the clones pW29-19 and p11-4 and were labeled with fluorescein (green). These probes detected chromosomes 13 and 21 simultaneously as a pair.

PNA probes for a particular chromosome listed in Table 2 used in a particular experiment were first mixed before hybridization with the cells.

Preferred Procedure for Performing In-Situ Hybridization:

Slides containing interphase nuclei and metaphase chromosome spreads, prepared as described above were treated with 25 μL of hybridization buffer (70% formamide, 1×Denhardt solution, 10 mM NaCl, 20 mM Tris pH 7.5, 0.1 μg/mL each of *E. Coli* tRNA and salmon sperm DNA) containing 0.1 μM of each fluorochrome labeled PNA probe for a particular chromosome listed in Table 2 (Except for X, Y and 1: See note below for information on probes used to generate the Figures). Slides were then heated at 70° C. for 10 minutes in a humidified incubator and then transferred to a ambient humidified incubator and PNA probe hybridization was allowed to proceed for 30-60 minutes. After a brief rinse in PBS and 0.1% tween 20 (Sigma) at room temperature, slides were washed in preheated 0.1% tween 20 in PBS (PBS is 2.7 mM KCl, 1.5 mM $KH_2PO$, 137 mM NaCl, and 8 mM $Na_2HPO$) at 55° C. for 30 minutes. Finally the slides were rinsed with PBS. Slides were then dehydrated in 70% and 100% ethanol for two minutes each and air dried for 10 minutes. Cells were then counterstained with 4,6-diamino-2-phenylindole (DAPI, Sigma Chemicals) and were mounted in 1,4-phenylenediamine in 90% glycerol in PBS. Slides were then analyzed using a microscope equipped with a CCD digital camera.

Digital Imaging Microscopy:

Images reproduced in FIGS. 1-11 and 13-21 were obtained using a Nikon fluorescent microscope equipped with a 60× immersion oil objective, a 10× ocular (total enlargement is 600 fold) and light filters obtained from Omega Optical (XF22 (green), XF34 (red), and XF05 (blue) filter). Electronic digital images were made of the slide using a SPOT CCD-camera and software obtained from Diagnostic Instruments, Inc., Sterling Heights, Mich. (USA).

Results:

General:

The composite digital images obtained, all covering the same section of the slide, are presented in FIGS. 1-11 and 13-21. With reference to the color images of FIGS. 1-11 and 13-21, the blue Dapi stain was used to visualize chromosomes of the metaphase spreads and interphase nuclei.

Specific Figures:

General Note: The Cy5 labeled probes listed in Table 2 were not used to generate any of FIGS. 1-11, 13-21. FIGS. 1-5 were obtained with only probes Rox-X-I-III and Flu-Y-I-IV and not probes of the entire set as identified in Table 2.

FIG. 1: Chromosomes X, Y and 1 are clearly detectable in the visible interphase nuclei and metaphase spreads. The perfectly paired sets of chromosomes indicate that these cells come from a normal human male.

Figure 2:
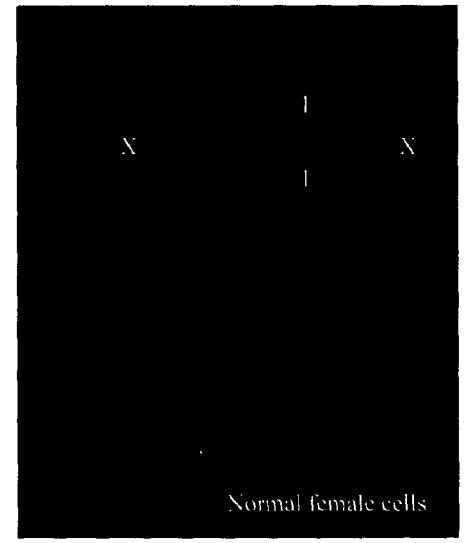
In FIG. 2 chromosomes X and 1 are clearly detectable in the visible interphase nuclei and metaphase spreads. The perfectly paired sets of chromosomes indicate that these cells come from a normal human female.

FIG. 2: Chromosomes X and 1 are clearly detectable in the visible interphase nuclei and metaphase spreads. The perfectly paired sets of chromosomes indicate that these cells come from a normal human female (chromosome Y was not detected).

Figure 3:
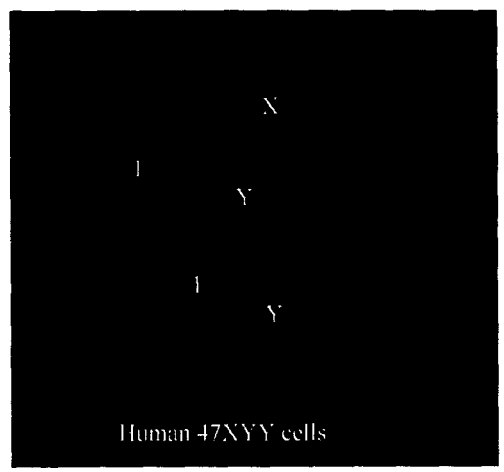
In FIG. 3 chromosomes X, Y and 1 are clearly detectable in the visible interphase nuclei and metaphase spreads. The imbalance in detectable chromosomes indicates that these cells come from human having an additional Y-chromosome (47XYY). This is an aneuploidy condition known as trisomy.

FIG. 3: Chromosomes X, Y and 1 are clearly detectable in the visible interphase nuclei and metaphase spreads. The imbalance in detectable chromosomes indicates that these cells come from human having an additional Y-chromosome (47XYY). This is an aneuploidy condition known as trisomy.

Figure 4:
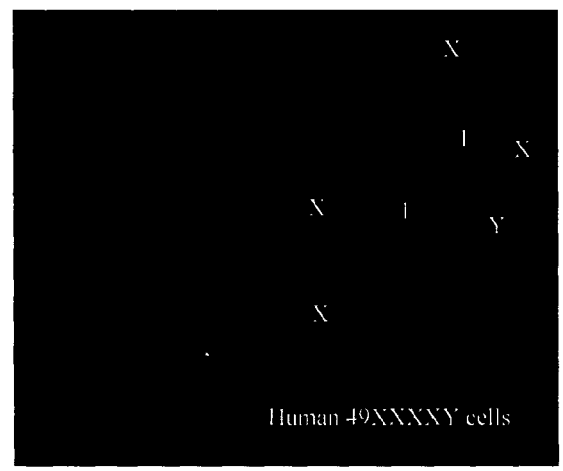
In FIG. 4 chromosomes X, Y and 1 are clearly detectable in the visible interphase nuclei and metaphase spreads. The imbalance in detectable chromosomes indicates that these cells come from human having three additional X-chromosomes (49XXXXY). This is an aneuploidy condition known as pentasomy.

FIG. 4: Chromosomes X, Y and 1 are clearly detectable in the visible interphase nuclei and metaphase spreads. The imbalance in detectable chromosomes indicates that these cells come from human having three additional X-chromosomes (49XXXXY). This is an aneuploidy condition known as pentasomy.

Figure 5:
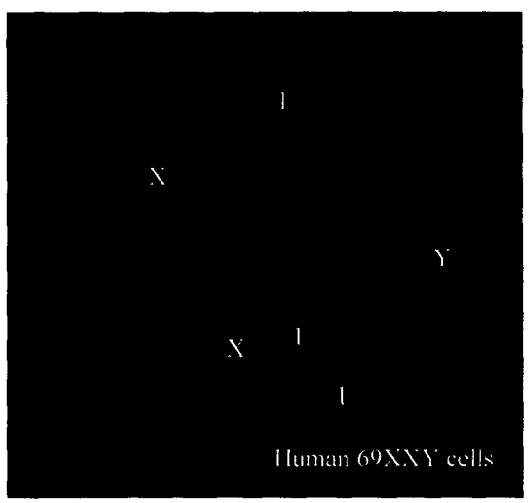
In FIG. 5 metaphase chromosomes of a human having a condition known as triploid (polyploidy) 69XXY is clearly detectable.

FIG. 5: Metaphase chromosomes of a human having a condition known as triploid (polyploidy) 69XXY is clearly detectable. It is noteworthy that without having the chromosome 1 reference (3 copies of chromosome 1 is visible), it would be more difficult to properly diagnosis this patent as polyploidy as compared with an aneuploidy 47XXY karyotype.

Figure 6:
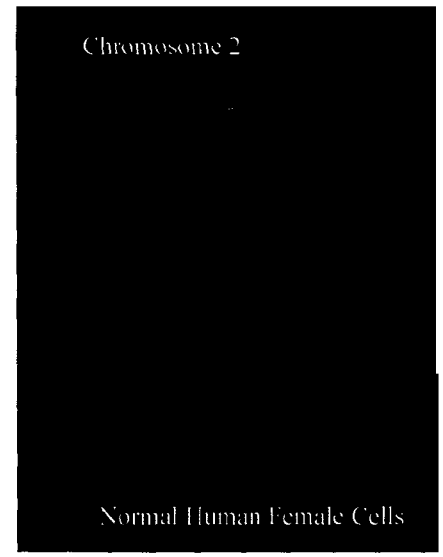
In FIG. 6 paired signals for human chromosome 2 are clearly detectable in the visible interphase nuclei and metaphase spreads.

FIG. 6: Pairs of human chromosome 2 are clearly detectable in the visible interphase nuclei and metaphase spreads. The perfectly paired sets of white spots indicate that these cells come from a human having a pair of human chromosome 2.

Figure 7:
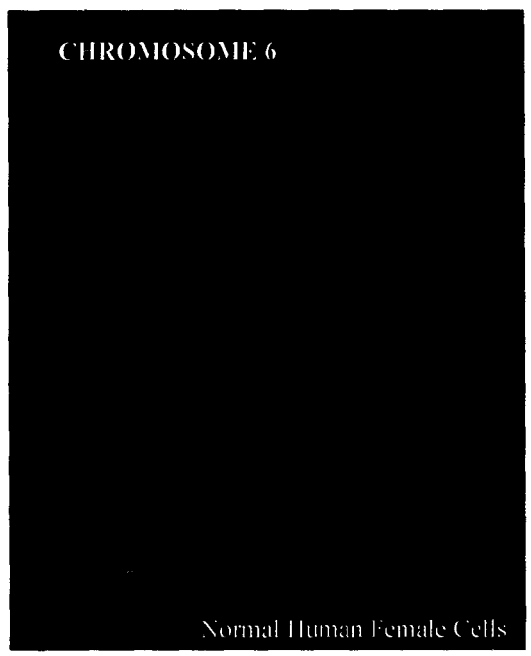
In FIG. 7 paired signals for human chromosome 6 are clearly detectable in the visible interphase nuclei and metaphase spreads.

FIG. 7: Pairs of human chromosome 6 are clearly detectable in the visible interphase nuclei and metaphase spreads. The perfectly paired sets of green spots indicate that these cells come from a human having a pair of human chromosome 6.

Figure 8:
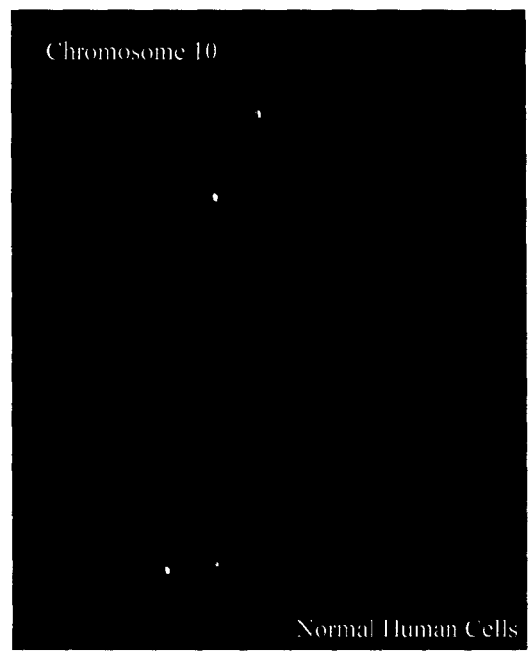
In FIG. 8 both rhodamine (red) and fluorescein (green) labeled PNA probes for chromosome 10 were simultaneously hybridized to the cells in the sample. Therefore, in the composite image, spots which are both green and red appear as white (computer generated color). Pairs of white spots for chromosome 10 are clearly detectable in the visible interphase nuclei and metaphase spreads. The data demonstrates that both the green and red PNA probes of different sequence hybridize to the same regions of the chromosomal DNA to thereby generate predominately white spots as compared with localized blotches of green and red.

FIG. 8: Pairs of chromosome 10 are clearly detectable in the visible interphase nuclei and metaphase spreads. The perfectly paired sets of green spots indicate that these cells come from a human having a pair of human chromosome 10.

Figure 9:
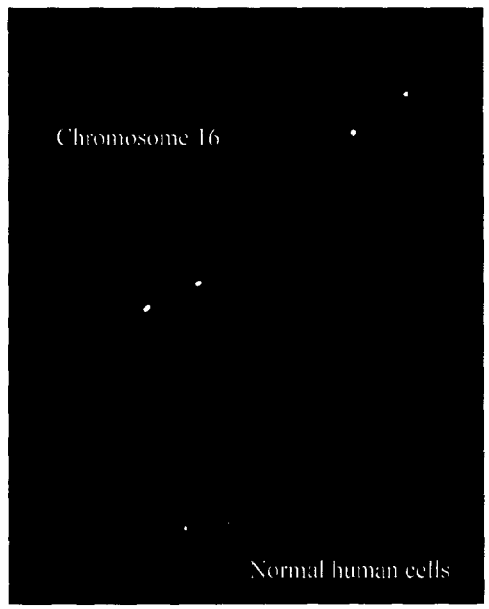
In FIG. 9 both rhodamine (red) and fluorescein (green) labeled PNA probes for chromosome 16 were simultaneously hybridized to the cells in the sample. Therefore, in the composite image, spots which are both green and red appear as white (computer generated color). Pairs of white spots for chromosome 16 are clearly detectable in the visible interphase nuclei and metaphase spreads. The data demonstrates that both the green and red PNA probes of different sequence hybridize to the same regions of the chromosomal DNA to thereby generate predominately white spots as compared with localized blotches of green and red.

FIG. 9: Pairs of chromosome 16 are clearly detectable in the visible interphase nuclei and metaphase spreads. The perfectly paired sets of white spots indicate that these cells come from a human having a pair of chromosome 16.

Figure 10:
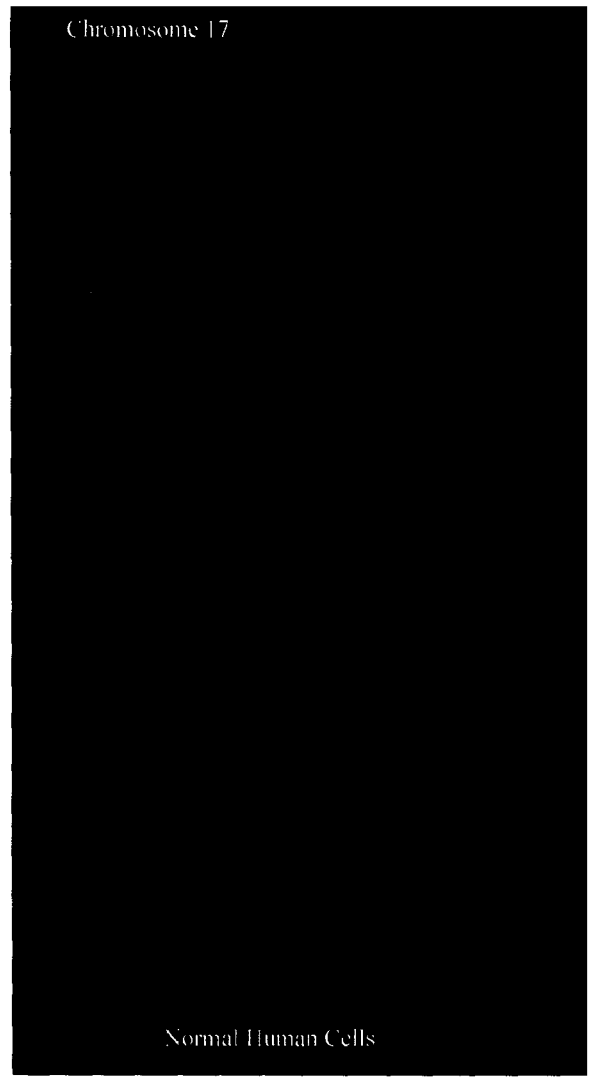
In FIG. 10 paired signals for chromosome 17 are clearly detectable in the visible interphase nuclei and metaphase spreads.

FIG. 10: Pairs of chromosome 17 are clearly detectable in the visible interphase nuclei and metaphase spreads. The perfectly paired sets of green spots indicate that these cells come from a human having a pair of chromosome 17.

Figure 11:
In FIG. 11 paired signals for human chromosome 18 are clearly detectable in the visible interphase nuclei and metaphase spreads.

FIG. 11: Pairs of chromosome 18 are clearly detectable in the visible interphase nuclei and metaphase spreads. The perfectly paired sets of green spots indicate that these cells come from a human having a pair of chromosome 18.

Figure 13:
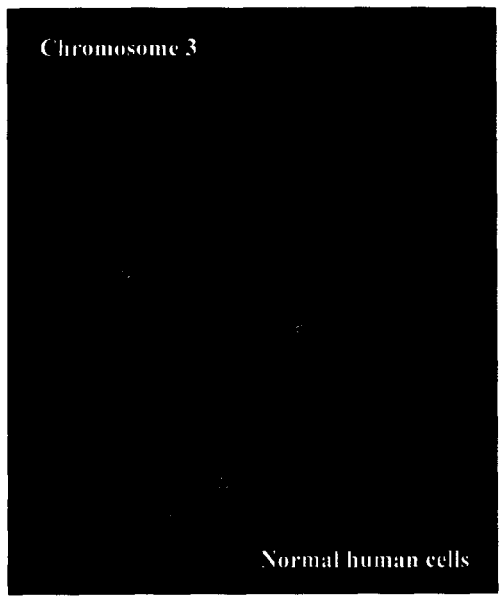
In FIG. 13, paired signals for human chromosome 3 are clearly detectable in the visible interphase nuclei and metaphase spreads.

FIG. 13: Pairs of chromosome 3 are clearly detectable in the visible interphase nuclei and metaphase spreads. The perfectly paired sets of green spots indicate that these cells come from a human having a pair of chromosome 3.

Figure 14:
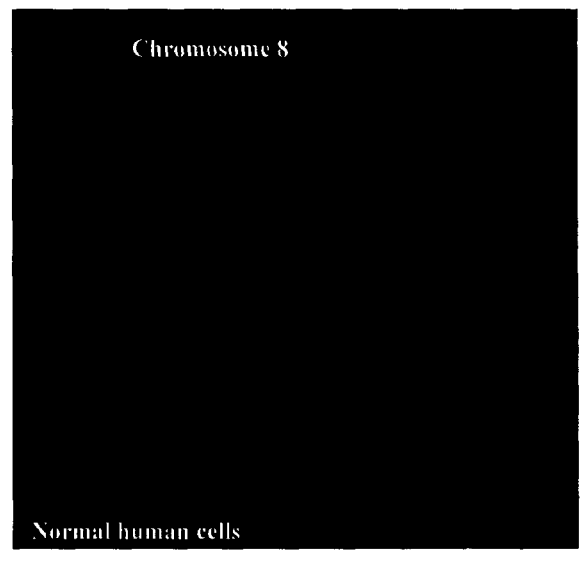
In FIG. 14, paired signals for human chromosome 8 are clearly detectable in the visible interphase nuclei and metaphase spreads.

FIG. 14: Pairs of chromosome 8 are clearly detectable in the visible interphase nuclei and metaphase spreads. The perfectly paired sets of green spots indicate that these cells come from a human having a pair of chromosome 8.

Figure 15:
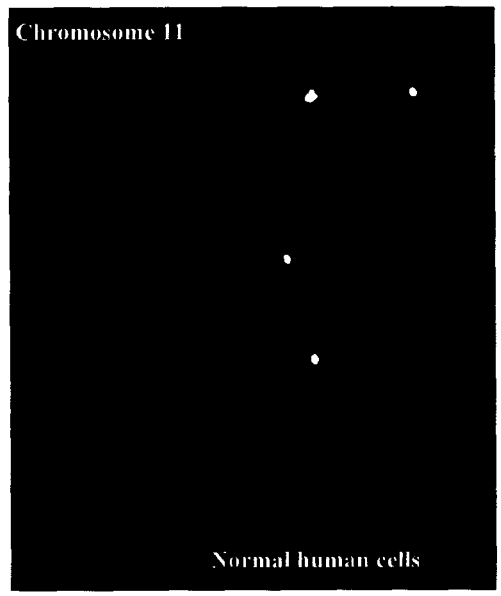
In FIG. 15, paired signals for human chromosome 11 are clearly detectable in the visible interphase nuclei and metaphase spreads.

FIG. 15: Pairs of chromosome 11 are clearly detectable in the visible interphase nuclei and metaphase spreads. The perfectly paired sets of green spots indicate that these cells come from a human having a pair of chromosome 11.

Figure 16:
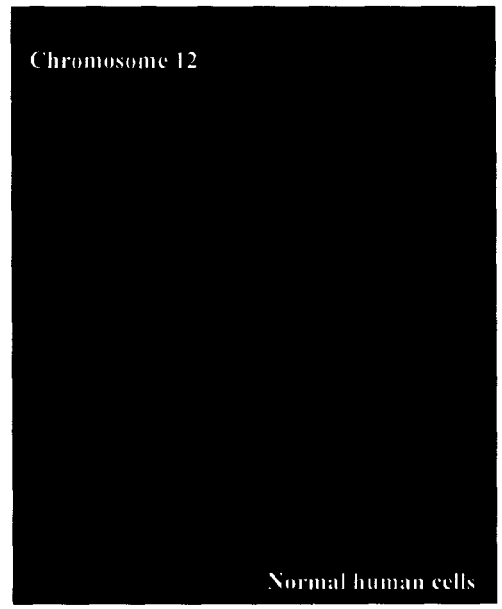
In FIG. 16, paired signals for human chromosome 12 are clearly detectable in the visible interphase nuclei and metaphase spreads.

FIG. 16: Pairs of chromosome 12 are clearly detectable in the visible interphase nuclei and metaphase spreads. The perfectly paired sets of green spots indicate that these cells come from a human having a pair of chromosome 12.

Figure 17:
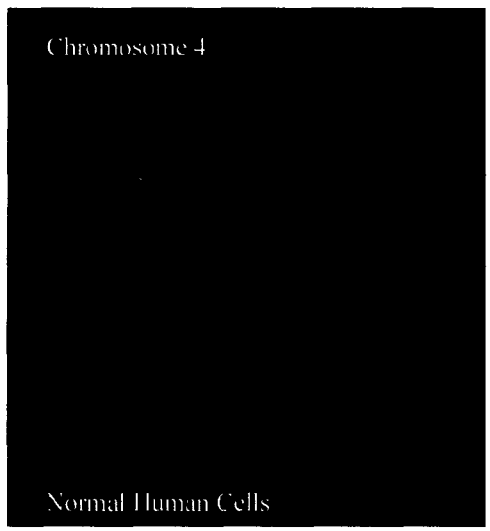
In FIG. 17, paired signals for human chromosome 4 are clearly detectable in the visible interphase nuclei and metaphase spreads.

FIG. 17: Pairs of chromosome 4 are clearly detectable in the visible interphase nuclei and metaphase spreads. The perfectly paired sets of green spots indicate that these cells come from a human having a pair of chromosome 4.

Figure 18:
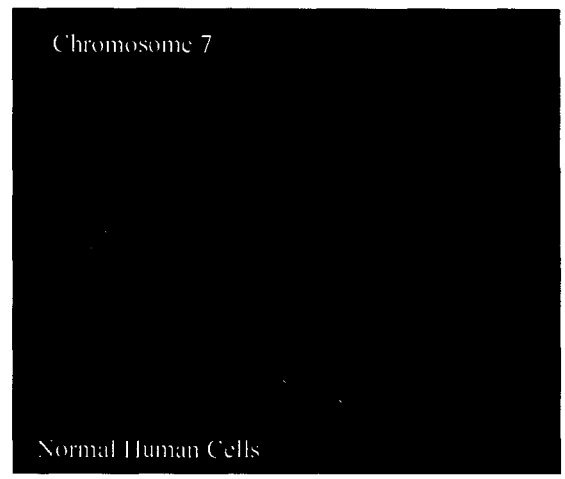
In FIG. 18, paired signals for human chromosome 7 are clearly detectable in the visible interphase nuclei and metaphase spreads.

FIG. 18: Pairs of chromosome 7 are clearly detectable in the visible interphase nuclei and metaphase spreads. The perfectly paired sets of green spots indicate that these cells come from a human having a pair of chromosome 7.

Figure 19:
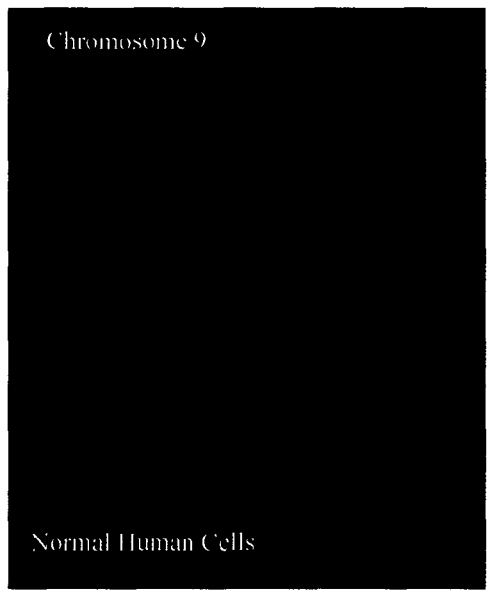
In FIG. 19, paired signals for human chromosome 9 are clearly detectable in the visible interphase nuclei and metaphase spreads.

FIG. 19: Pairs of chromosome 9 are dearly detectable in the visible interphase nuclei and metaphase spreads. The perfectly paired sets of red spots indicate that these cells come from a human having a pair of chromosome 9.

Figure 20:
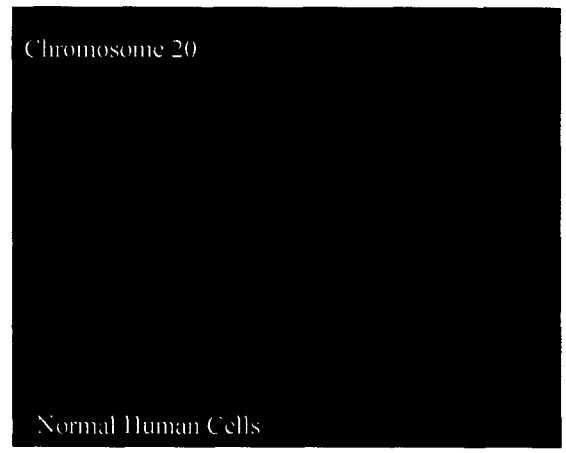
In FIG. 20, paired signals for human chromosome 20 are clearly detectable in the visible interphase nuclei and metaphase spreads.

FIG. 20: Pairs of chromosome 20 are clearly detectable in the visible interphase nuclei and metaphase spreads. The perfectly paired sets of green spots indicate that these cells come from a human having a pair of chromosome 20.

FIG. 21: Chromosome 13/21 as two pairs of spots are clearly detectable in the visible interphase nuclei and metaphase spreads. The four detectable green spots indicate that these cells come from a human having a both a pair of human chromosome 13 as well as a pair of human chromosome 21.

Example 10

Multiplex PNA-FISH Used for the Independent Detection of Human Chromosomes X, Y and 1

Cytogenetic Preparations

Figure 12:
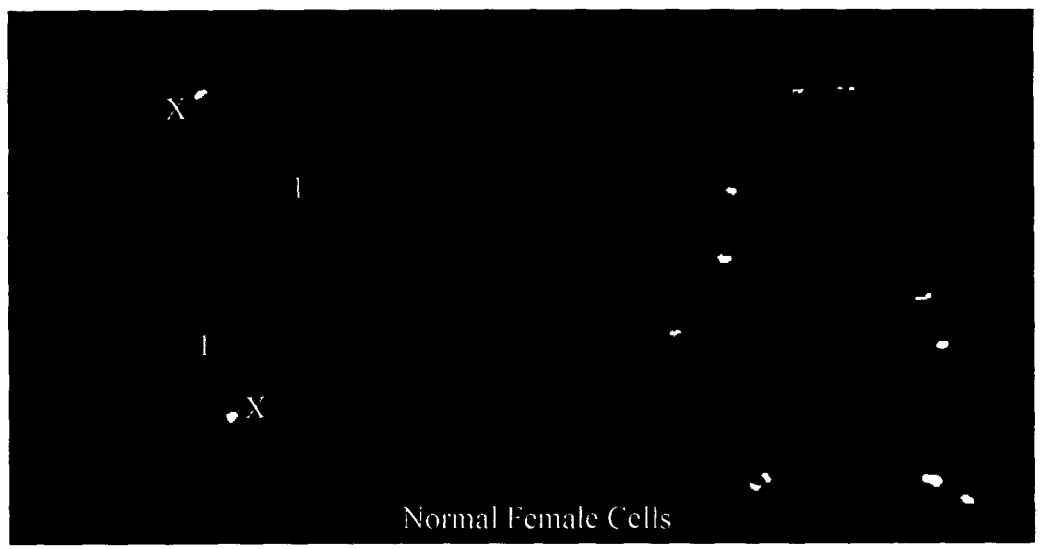
In FIGS. 12A and 12B the composite digital image was obtained with each of the blue, green, red (pseudo colored orange) and Cy5 (pseudocolored red) filters of a CCD camera attached to a microscope. Chromosomes X, Y and 1 are clearly detectable in the visible interphase nuclei and metaphase spreads. The cells observed in FIG. 12A are from a normal human female (XX,11) and the cells observed in FIG. 12B are from a normal human male (XY,11).
Figure 12:
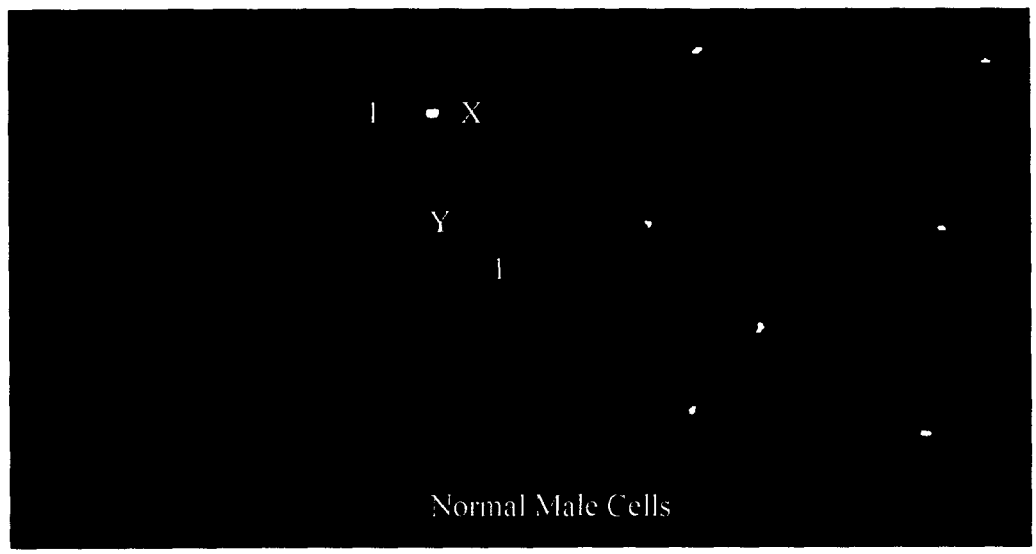

Cells were prepared essentially as described in Example 9.
Preparation of Chromosome Specific Probes:
Probe Design is essentially as described in Example 9.
Specific PNA probes used to generate FIG. 12 are listed in Tables 2 except that probes Cy5-1-I and Cy5-1-II were substituted for Rox-1-I and Rox-1-II, respectfully. Therefore, all of the PNA probes for chromosomes X, Y and 1 listed in Table 2 (except for Rox-1-I and Rox-1-II) were mixed before hybridization with the cells prepared as described under subheading "Cytogenetic Preparations".
In-Situ Hybridization:
In-Situ Hybridization, using the mixture of PNA probes was performed essentially as described in Example 9.
Digital Imaging Microscopy:
The image reproduced in FIG. 12 was obtained essentially as described in Example 9, except that light filters were as follows: The filter sets for green (XF22), red (XF34), blue (XF05) were obtained from Omega Optical. The filter set for the Cy5 dye (P/N 31023, Ex: D640/20 and Em: D680/30) was obtained from Chroma Technology Corp. However, the colors appearing in the figure have been pseudocolored (by the software) since Cy5 is not visible. The green and blue filter sets still yields a green and blue signal, respectfully. However, the red filter set has been fixed to appear as pseudocolor orange (identifies the rhodamine labeled X chromosome probe) in the Figure and the Cy5 filter set has been fixed to appear as pseudocolor red in the Figure.

Results:

General:

The composite digital image obtained, all covering the same section of the slide, are presented in FIGS. 12A and 12B. With reference to the Figures, the blue Dapi stain was used to visualize chromosomes of the metaphase spreads and interphase nuclei. The signal from the CCD camera for each filter set was colored or pseudocolored using the software. Colors presented in the Figure are pseudocolor orange (chromosomes X), green (chromosomes Y) and pseudocolor red Cy5 (Chromosomes 1). Because the multicolor analysis provides a means to identify the sex chromosomes (X and Y) as well as a reference chromosome (chromosome 1), it is possible to detect chromosome abnormalities associated with both aneuploidy and polyploidy conditions.

Specific Figures:

FIG. 12A: Chromosomes X and 1 are clearly detectable in the visible interphase nuclei and metaphase spreads. In the Figure, each individual X, Y and 1 chromosome can be detected and counted (scored) since three independently detectable fluorophores were used, one for each chromosome type. The data indicates that these cells come from normal human female (XX).

FIG. 12B: Chromosomes X, Y and 1 are clearly detectable in the visible interphase nuclei and metaphase spreads. In the Figure, each individual X, Y and 1 chromosome can be detected and counted (scored) since three independently detectable fluorophores were used, one for each chromosome type. The data indicates that these cells come from a normal human male.

EQUIVALENTS

While this invention has been particularly shown and described with references to preferred embodiments thereof, it will be understood by those of ordinary skill in the art that various changes in form and details may be made therein without departing from the spirit and scope of the invention as defined by the appended claims. Those skilled in the art will be able to ascertain, using no more than routine experimentation, many equivalents to the specific embodiments of the invention described herein. Such equivalents are intended to be encompassed in the scope of the claims.

The invention claimed is:

1. A PNA probe of up to 30 subunits in length comprising a probing nucleobase sequence selected from the group consisting of SEQ ID NOS 10-16 or the complement thereof.

2. The probe of claim 1, wherein the probe is unlabeled.

3. The probe of claim 1, wherein the probe is labeled with at least one detectable moiety.

4. The probe of claim 3, wherein the detectable moiety or moieties are selected from the group consisting of: a dextran conjugate, a branched nucleic acid detection system, a chromophore, a fluorophore, a spin label, a radioisotope, an enzyme, a hapten, an acridinium ester and a chemiluminescent compound.

5. The probe of claim 1, wherein the probe is labeled with at least two independently detectable moieties.

6. The probe of claim 5, wherein the two or more independently detectable moieties are independently detectable fluorophores.

7. The probe of claim 1, wherein the probe is support bound.

8. A probe set comprising at least one PNA probe of up to 30 subunits in length wherein one or more of the PNA probes of the set is specific for detecting human chromosome Y and comprises a probing nucleobase sequence selected from the group consisting of SEQ ID NOS 10-16 or the complement thereof.

9. The probe set of claim 8, wherein the probe set comprises at least two probes and wherein two or more probes of the set are independently detectable.

10. The probe set of claim 9, wherein one or more of the independently detectable probes are labeled with two or more independently detectable moieties.

11. The probe set of claim 9, wherein the independently detectable probes are used to distinguish between human chromosomes X, Y, 1, 2, 3, 4, 6, 7, 8, 9, 10, 11, 12, 16, 17, 18 and 20, as well as 13/21 as a pair.

12. A method comprising:
a) contacting a sample with a PNA probe set, wherein the PNA probe set comprises one or more PNA probes of up to 30 subunits in length wherein one or more of the PNA probes of the set is specific for detecting human chromosome Y and comprises a probing nucleobase sequence selected from the group consisting of SEQ ID NOS 10-16 or the complement thereof; and
b) detecting, identifying or quantitating hybridization of the probing nucleobase sequence of the PNA probe or probes to the target sequences of the chromosomes and correlating the result with the presence, absence or number of the chromosomes in the sample.

13. The method of claim 12, wherein in-situ hybridization is used to detect, identify or enumerate human chromosomes X, Y, 1, 2, 3, 4, 6, 7, 8, 9, 10, 11, 12, 16, 17, 18 and 20, as well as 13/21 as a pair, in the sample.

14. The method of claim 12, wherein the method is used to detect or identify chromosome related abnormalities.

15. The method of claim 12, wherein the method is used to detect abnormalities in cells, tissues (including bone marrow), spermatozoa, ova, blastomeres, oocysts, buccal cells and chorinic vile.

16. The method of claim 15, wherein the chromosome related abnormality is aneuploidy or polyploidy.

17. The method of claim 15, wherein the method is used in preimplantation diagnosis or in prenatal screening.

18. A set of at least four PNA probes of up to 30 subunits in length wherein:
a) one or more of the PNA probes of the set is specific for detecting human chromosome X and comprises a probing nucleobase sequence selected from the group consisting of SEQ ID NOS 1-9 or the complement thereof; and
b) one or more of the PNA probes of the set is specific for detecting human chromosome Y and comprises a probing nucleobase sequence selected from the group consisting of SEQ ID NOS 10-16 or the complement thereof; and
c) one or more of the PNA probes of the set is specific for detecting human chromosome 18 and comprises a probing nucleobase sequence selected from the group consisting of SEQ ID NOS 112-118 or the complement thereof; and
d) one or more of the PNA probes of the set is specific for detecting human chromosome 13/21 and comprises a probing nucleobase sequence selected from the group consisting of SEQ ID NOS 153-159 or the complement thereof.

19. A kit for performing an assay comprising:
a) one or more PNA probes of up to 30 subunits in length wherein at least one probe comprises a probing nucleobase sequence selected from the group consisting of SEQ ID NOS 10-16 or the complement thereof; and
b) other reagents or compositions necessary to perform the assay.

20. The kit of claim 19, wherein the probe or probes are unlabeled.

21. The kit of claim 20, wherein the kit further comprises an antibody or antibody fragment, wherein the antibody or antibody fragment specifically binds, under antibody binding conditions, to the PNA/nucleic acid complex which forms under suitable hybridization conditions.

22. The kit of claim 21, comprising an antibody labeled with a detectable moiety.

23. The kit of claim 22, wherein the detectable moiety is selected from the group consisting of a dextran conjugate, a branched nucleic acid detection system, a chromophore, a fluorophore, a spin label, a radioisotope, an enzyme, a hapten, an acridinium ester and a chemiluminescent compound.

24. The kit of claim 19, wherein at least one PNA probe is labeled with a detectable moiety.

25. The kit of claim 24, wherein the detectable moiety or moieties are selected from the group consisting of: a dextran conjugate, a branched nucleic acid detection system, a chromophore, a fluorophore, a spin label, a radioisotope, an enzyme, a hapten, an acridinium ester and a chemiluminescent compound.

26. A prenatal kit for the multiplex analysis of human chromosomes X, Y, 1, 2, 3, 4, 6, 7, 8, 9, 10, 11, 12, 16, 17, 18, and 13/21 as a pair, wherein the kit comprises:

a) at least one independently detectable PNA probe of up to 30 subunits in length selected from the group consisting of SEQ ID NOS 1-159 or the complement thereof, wherein at least one probe comprises one of SEQ ID NOS 10-16 or the complement thereof; and b) other reagents or components suitable to perform the assay.

27. The PNA probe set of claim 8 wherein the set further comprises at least one PNA probe of up to 30 subunits comprising a probing nucleobase sequence selected from the group consisting of SEQ ID NOS 1-9, 17-159, and the complement to any of the foregoing sequences.

28. The method of claim 12 wherein the PNA probe set further comprises at least one PNA probe of up to 30 subunits comprising a probing nucleobase sequence selected from the group consisting of SEQ ID NOS 1-9, 17-159, and the complement to any of the foregoing sequences.

* * * * *